(12) United States Patent
Ricciardi

(10) Patent No.: US 9,211,296 B2
(45) Date of Patent: Dec. 15, 2015

(54) THERAPEUTIC COMPOUNDS FOR BLOCKING DNA SYNTHESIS OF POX VIRUSES

(71) Applicant: The Trustees of the University of Pennsylvania, Philadelphia, PA (US)

(72) Inventor: Robert P. Ricciardi, East Marlborough, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 42 days.

(21) Appl. No.: 14/011,378

(22) Filed: Aug. 27, 2013

(65) Prior Publication Data

US 2013/0338117 A1 Dec. 19, 2013

Related U.S. Application Data

(60) Division of application No. 13/590,667, filed on Aug. 21, 2012, now Pat. No. 8,524,719, which is a division of application No. 12/537,083, filed on Aug. 6, 2009, now Pat. No. 8,278,342, which is a continuation-in-part of application No. PCT/US2008/001553, filed on Feb. 6, 2008.

(60) Provisional application No. 60/899,633, filed on Feb. 6, 2007, provisional application No. 60/929,673, filed on Jul. 9, 2007.

(51) Int. Cl.
| | |
|---|---|
| A61K 31/65 | (2006.01) |
| A61K 31/095 | (2006.01) |
| A61K 31/166 | (2006.01) |
| A61K 31/198 | (2006.01) |
| A61K 31/426 | (2006.01) |
| A61K 31/10 | (2006.01) |

(Continued)

(52) U.S. Cl.
CPC .............. *A61K 31/65* (2013.01); *A61K 31/095* (2013.01); *A61K 31/10* (2013.01); *A61K 31/166* (2013.01); *A61K 31/198* (2013.01); *A61K 31/341* (2013.01); *A61K 31/351* (2013.01); *A61K 31/352* (2013.01); *A61K 31/357* (2013.01); *A61K 31/42* (2013.01); *A61K 31/426* (2013.01); *A61K 31/427* (2013.01); *A61K 31/429* (2013.01); *A61K 31/473* (2013.01); *A61K 31/496* (2013.01); *A61K 31/519* (2013.01)

(58) Field of Classification Search
CPC ..................................................... A61K 31/65
USPC ....................................................... 514/152
See application file for complete search history.

(56) References Cited

U.S. PATENT DOCUMENTS

| | | |
|---|---|---|
| 5,527,819 A | 6/1996 | Williams et al. |
| 2002/0068014 A1 | 6/2002 | Haught et al. |

(Continued)

OTHER PUBLICATIONS

Mirocha et al., "Fungus metabolites toxic to animals", Annual review of phytopathology, 1974, vol. 12, pp. 303-330.

(Continued)

*Primary Examiner* — Shengjun Wang
(74) *Attorney, Agent, or Firm* — Mark S. Cohen; Pearl Cohen Zedek Latzer Baratz LLP

(57) ABSTRACT

This invention provides methods of inhibiting replication of a poxvirus by contacting a poxvirus with a compound having formula I, formula XXI, formula XXXII, or formula XLI which in turn reduce, inhibit, or abrogate poxvirus DNA polymerase activity and/or its interaction with its processivity factor. Formula I, formula XXI, formula XXXII, or formula XLI can be utilized to treat humans and animals suffering from a poxvirus infection. Pharmaceutical compositions for treating poxvirus infected subjects are also provided.

12 Claims, 15 Drawing Sheets

Figure 1:
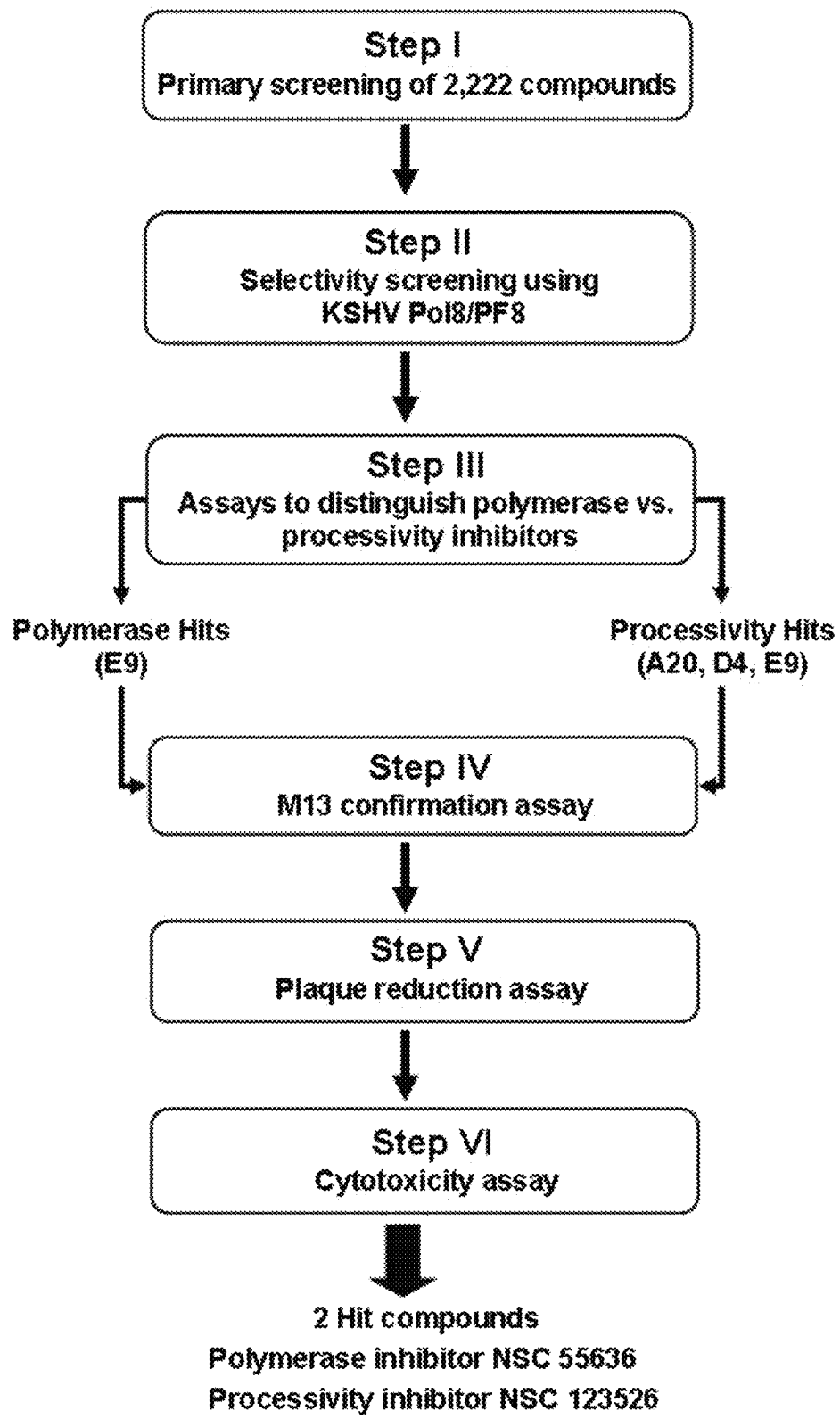

(51) Int. Cl.
| | |
|---|---|
| A61K 31/341 | (2006.01) |
| A61K 31/351 | (2006.01) |
| A61K 31/352 | (2006.01) |
| A61K 31/357 | (2006.01) |
| A61K 31/42 | (2006.01) |
| A61K 31/427 | (2006.01) |
| A61K 31/429 | (2006.01) |
| A61K 31/473 | (2006.01) |
| A61K 31/496 | (2006.01) |
| A61K 31/519 | (2006.01) |

(56) References Cited

U.S. PATENT DOCUMENTS

| | | |
|---|---|---|
| 2006/0052418 A1 | 3/2006 | Beaulieu et al. |
| 2007/0021442 A1 | 1/2007 | Saggar et al. |

OTHER PUBLICATIONS

Okazaki et al., "Antiviral activity of macrocyclic trichothecene mycotoxins and related compounds baccharinoids B-4 and B-5 against Herpes", Agric. Biol. Chem., 1989, vol. 53 (5), pp. 1141-1143.

Ragno et al., "Docking and 3D-QSAR studies in indolyl aryl sulfones, binding mode exploration at the HIV reverse transcriptase non-nucleoside binding site and design of highly active N-(2-hydroxyethyl)carboxamide and N-(2-hydroxyethyl)carbohydrazide derivatives", J. Med. Chem. 2005, vol. 48, pp. 218-223.

Abad-Zapatero et al. "Ligand efficiency indices as guideposts for drug discovery", Drug Discov Today, Apr. 1, 2005;10(7):464-9.

Abagyan et al. "ICM—a new method for protein modeling and design. Applications to docking and structure prediction from the distorted native conformation", J. Comp. Chem., (1994), 15, 488-506.

Abuchowski et al. "Alteration of the circulating life and antigenic properties of bovine adenosine deaminase in mice by attachment of polyethylene glycol", Clin Exp Immunol. Dec. 1981;46(3):649-52.

Bonneau et al. "De novo prediction of three-dimensional structures for major protein families", J. Mol. Biol. 2002, 322, 65-78.

Berge et al. "Pharmaceutical salts", Journal of Pharmaceutical Science, 66, 1-19 (1977).

Brenke et al. "Fragment-based identification of druggable 'hot spots' of proteins using Fourier domain correlation techniques", Bioinformatics 2009, 25, 621-627.

Buchwald et al., "Long-term, continuous heparin administration by an implantable infusion pump in ambulatory patients with recurrent venous thrombosis", Surgery, 88 (1980), pp. 507-516.

Chang et al. "The E3L gene of vaccinia virus encodes an inhibitor of the interferon-induced, double-stranded RNA-dependent protein kinase", Proc. Natl. Acad. Sci. USA, vol. 89, pp. 4825-4829, Jun. 1992.

Goodson, in Medical Applications of Controlled Release, vol. 2, pp. 115-138 (1984).

Ishii et al. "Mapping Interaction Sites of the A20R Protein Component of the Vaccinia Virus DNA Replication Complex", Virology 2002, 303, 232-239.

Katre et al. "Chemical modification of recombinant interleukin 2 by polyethylene glycol increases its potency in the murine Meth A sarcoma model", Proc. Natl. Acad. Sci. USA, vol. 84, pp. 1487-1491, Mar. 1987.

Klemperer et al. "The A20R Protein is a Stoichiometric Component of the Processive Form of Vaccinia Virus DNA Polymerase", J. Virol. 2001, 75, 12298-12307.

Langer "New methods of drug delivery", Science, 249 (1990), pp. 1527-1533.

Longini et al. "Containing a large bioterrorist smallpox attack: a computer simulation approach", Int. J. Infec. Dis. 2007, 11, 98-108.

Lopez-Berestein IJ Fidler (eds.) Liposomes in Therapy of Infectious Diseases and Cancer. Alan R. Liss, New York (1989), p. 317.

Maa et al. "Structural and Functional Studies of a 39,000-Mr Immunodominant Protein of Vaccinia Virus", J. Virol. 1987, 61, 3910-3919.

Newmark et al. "Tuberous sclerosis evaluated by computerized tomography", vol. 6, Issue 5, Sep.-Oct. 1982, pp. 287-293.

Nuth et al. " Identification of Inhibitors that Block Vaccinia Virus Infection by Targeting the DNA Synthesis Processivity Factor D4", J. Med. Chem. 2011, 54, 3260-7.

"Poxviruses", retrieved online on Jan. 12, 2015 at: http://emedicine.medscape.com/article/226239-overview, last updated Sep. 30, 2013.

"Poxviruses Treatment and Management", retrieved online on Jan. 12, 2015 at: http://emedicine.medscape.com/article/226239-treatment, last updated Sep. 30, 2013.

Risco et al. "The Vaccinia Virus 39-kDa Protein Forms a Stable Complex with the p4a/4a Major Core Protein Early in Morphogenesis", Virology 1999, 265, 375-386.

Saudek et al. "A Preliminary Trial of the Programmable Implantable Medication System for Insulin Delivery", N. Engl. J. Med. 321:574 (1989).

Schormann et al. "Crystal structure of vaccinia virus uracil-DNA glycosylase reveals dimeric assembly", BMC Struct. Biol., 2007, 7:45.

Sefton "Implantable Pumps", CRC Press, Boca Raton, FL, Etats-Unis (1981) (Revue) 1987, vol. 14, No. 3, pp. 201-240.

Shudofsky et al. "Vaccinia Virus D4 Mutants Defective in Processive DNA Synthesis Retain Binding to A20 and DNA", J. Virol. 2010, 84, 12325-12335.

Simons et al. "Improved Recognition of Native-Like Protein Structures Using a Combination of Sequence-Dependent and Sequence-Independent Features of Proteins", Proteins: Structure, Function, and Genetics 34:82-95 (1999).

Stanitsa et al. "Vaccinia Virus Uracil DNA Glycosylase Interacts with the A20 Protein to Form a Heterodimeric Processivity Factor for the Viral DNA Polymerase", J. Biol. Chem. 2006, 281, 3439-3451.

Treat et al., in Liposomes in the Therapy of Infectious Disease and Cancer, Lopez-Berestein and Fidler (eds.), Liss, New York, pp. 353-365 (1989).

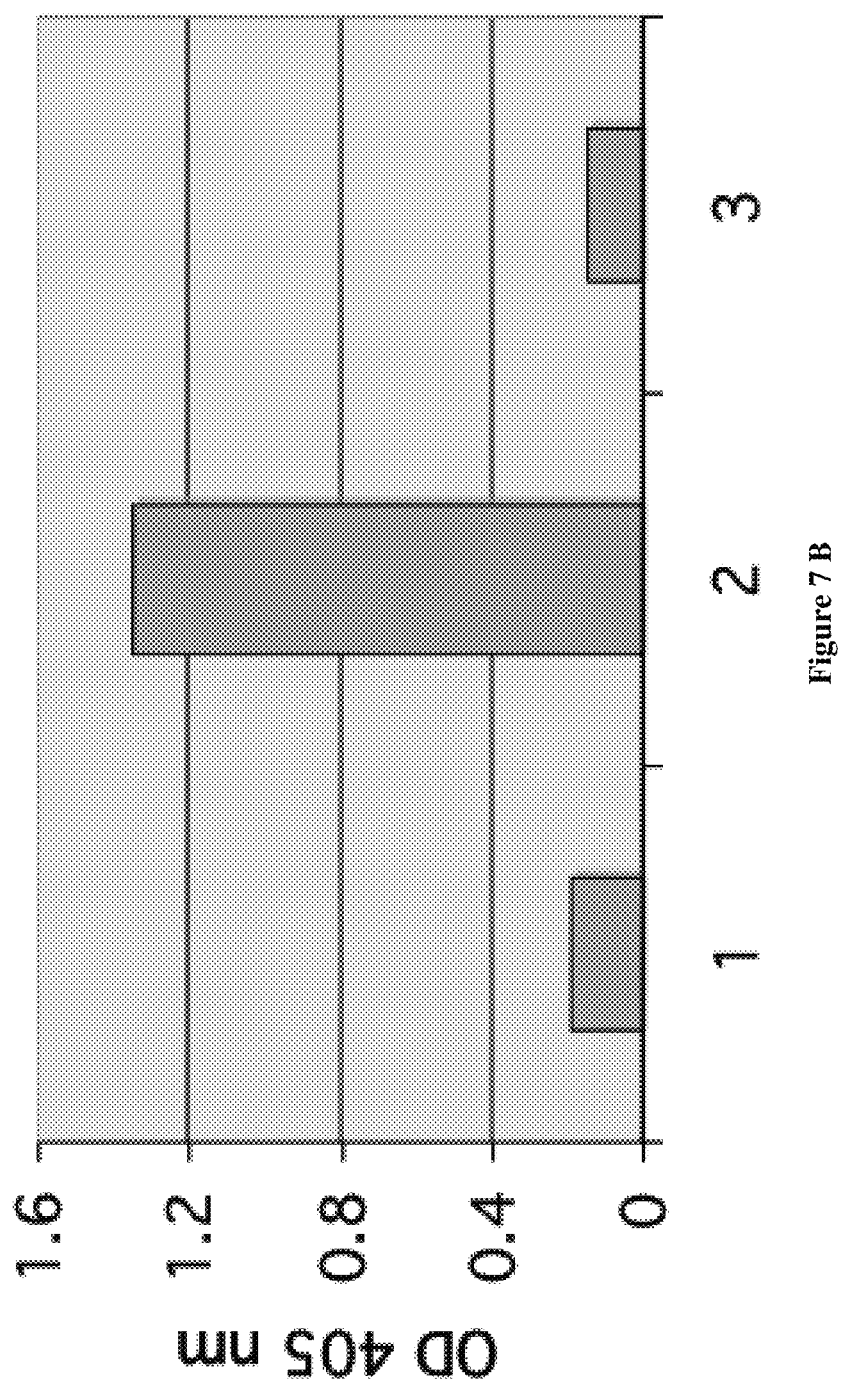

Figure 11

A

B

THERAPEUTIC COMPOUNDS FOR BLOCKING DNA SYNTHESIS OF POX VIRUSES

CROSS REFERENCE TO RELATED APPLICATIONS

This application is a divisional application of Ser. No. 13/590,667, filed Aug. 21, 2012, which is a divisional application of Ser. No. 12/537,083, filed Aug. 6, 2009, which is a continuation-in part of international patent application PCT/US08/01553, filed Feb. 6, 2008, which claims priority to U.S. provisional patent applications 60/899,633 and 60/929,673, filed Feb. 6, 2007 and Jul. 9, 2007, respectively, all of which are incorporated herein by reference in their entirety.

GOVERNMENT INTEREST STATEMENT

This invention was made in whole or in part with government support under Grant Number U54 AI 57168, awarded by the National Institutes of Health. The government may have certain rights in the invention.

FIELD OF THE INVENTION

The invention relates to methods and compositions of preventing infection by PDX virus using compounds that interfere viral DNA replication.

BACKGROUND OF THE INVENTION

Poxviruses are the largest known animal viruses. They are DNA viruses that replicate entirely in the cytoplasm. The 191-kbp genome is a double-stranded DNA molecule whose ends are covalently connected by single-stranded hairpin loops of 101 nucleotides. The sequences that form the hairpins are AT-rich and lie at the ends of 12-kbp inverted terminal repetition elements that contain short direct repeats and several open reading frames.

Poxviruses infect most vertebrates and invertebrates, causing a variety of diseases of veterinary and medical importance. The one large family (Poxyiridae) has two main subfamilies, the chordopoxyirinae, which infect vertebrates, and the entomopoxyirinae, which infect insects. Humans are the sole hosts of two poxviruses, variola virus (smallpox virus) and molluscum contagiosum virus, although many members of Orthopoxvirus, Parapoxvirus, and Yatapoxvirus can infect both animals and humans. Vaccinia virus is the virus used in the variola virus vaccine, and it is widely used as a model poxvirus.

At least two variants of variola virus are known, and they cause two forms of smallpox: variola major, with a case fatality rate of 30-40%, and variola minor, with a much reduced fatality rate of about 1%. At the genome level, the two variants are very similar. Thus, essentially all of the encoded proteins are nearly identical.

Essential viral enzymes have frequently proven to be good targets for antiviral drugs (for example, HIV reverse transcriptase and protease).

The E9 DNA polymerase, required for DNA replication, acts in concert with accessory proteins to attain efficient processive synthesis. Accessory proteins include the A20 protein, D4R, and others. The viral DNA polymerase is an established drug target, as exemplified by azidothymidine (AZT), which inhibits the HIV reverse transcriptase, and acyclovir, which is efficiently phosphorylated by the herpes simplex virus viral thymidine kinase, resulting in a triphosphate that preferentially inhibits viral DNA polymerase.

Naturally occurring variola virus has been eradicated from the planet. Given the virulence of this virus and its ability to spread in a population, the consequences of an intentional release of variola virus could be devastating. Official stocks of the virus are closely held, but it is not known whether undeclared stocks exist, so it is difficult to assess the current degree of risk. Safer vaccines and therapeutics that can mitigate the consequences of infection would together provide a strong deterrent to any intentional release.

SUMMARY OF THE INVENTION

In one embodiment, this invention provides a method of inhibiting replication of a poxvirus, comprising contacting a poxvirus with viridicatumtoxin (formula (XLIV), NSC 55636, NSC 123526, or a combination thereof whereby viridicatumtoxin, NSC 55636, NSC 123526, or a combination thereof reduces, inhibits, or abrogates activity of a poxvirus DNA polymerase.

In one embodiment, this invention provides a method of inhibiting replication of a poxvirus, comprising contacting a poxvirus with a compound having the formula I:

$$A-X-B \qquad \qquad I$$

wherein A is:

Q is $NCH_2CH_2R$ or O;

R is OH, $N(CH_3)_2$ or $CH_3$;

$R_1$ and $R_2$ are independently, hydrogen, $CH_3$, OH or Cl;

$R_4$, $R_4'$ and $R_4''$ are independently, hydrogen, COOH, OH, $CF_3$, Cl, Br, COOMe, OMe, $N(CH_3)_2$ or $NO_2$;

$W_1$ is alkyl, alky-isothiourea or substituted alkyl;

B is 1 of the following structures:
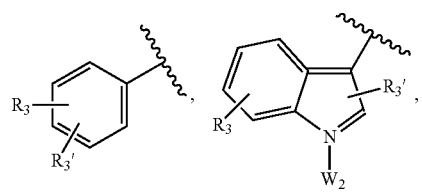
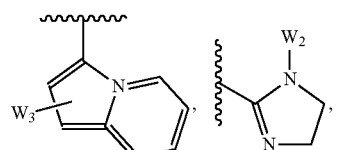
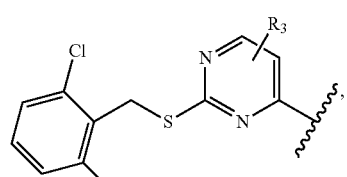
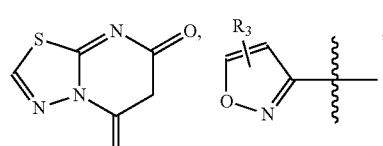
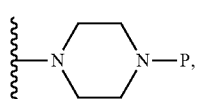
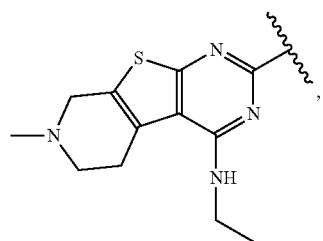
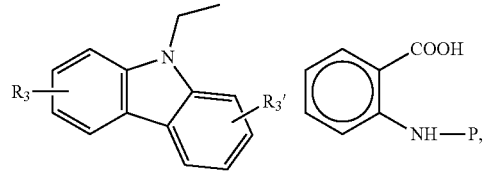
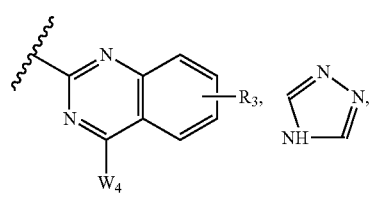
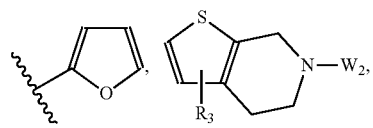
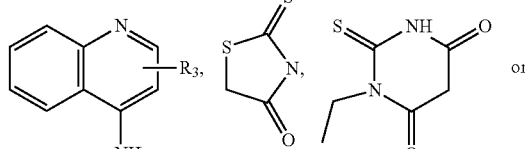
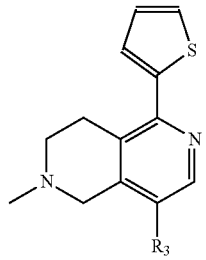
$R_3$ and $R_3'$ are hydrogen, COOH, OH, COOMe, Cl, $CF_3$, $CH_3$, $OCH_3$, $N(CH_3)_2$ or CN;
$W_2$ is alkyl, alky-isothiourea or substituted alkyl, —SO2Et, H or isopropyl;
$W_3$ is 2,4 dimethoxy phenyl;
$W_4$ is $CH_3$ or NH—$W_3$; and
P is hydrogen, Fmoc, or Boc;
X is nothing, $SO_2$, —TeCH$_2$CH$_2$NHCH$_2$CH$_2$Te—, NH, S,
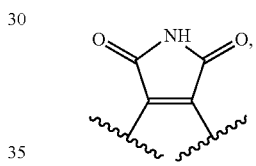
—CO—, —CH$_2$S—, —N=CH—, —COO—, —OCO—,
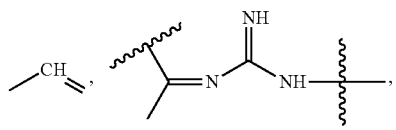
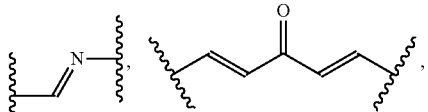
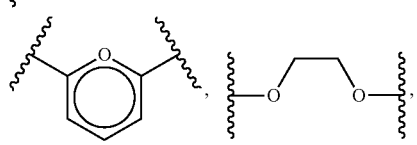
—CONH—, —NHCO—,
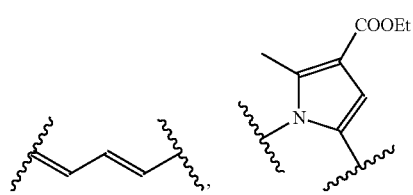
or or A-X—B are fused rings, wherein X is a 5-membered substituted or non-substituted heterocyclic or carbocyclic, optionally aromatic ring represented by 1 of the following structures:

A is and
B is whereby the compound reduces, inhibits, or abrogates activity of a poxvirus DNA polymerase.

In one embodiment, this invention provides a method of inhibiting replication of a poxvirus, comprising contacting a poxvirus with a compound having the formula XXI, whereby the compound reduces, inhibits, or abrogates activity of a poxvirus DNA polymerase.

In one embodiment, this invention provides a method of inhibiting replication of a poxvirus, comprising contacting a poxvirus with a compound having the formula XXXII, whereby the compound reduces, inhibits, or abrogates activity of a poxvirus DNA polymerase.

In one embodiment, this invention provides a method of inhibiting replication of a poxvirus, comprising contacting a poxvirus with a compound having the formula XLI, whereby the compound reduces, inhibits, or abrogates activity of a poxvirus DNA polymerase.

In one embodiment, this invention provides a method of inhibiting replication of a poxvirus, comprising contacting a poxvirus with a mixture comprising compounds having the formula XXI, XXXII, XLI, whereby the compound reduces, inhibits, or abrogates activity of a poxvirus DNA polymerase.

In another embodiment, this invention provides a method of inhibiting, treating, or abrogating a poxvirus infection in a subject, comprising administering to a subject viridicatumtoxin, NSC 55636, NSC 123526, or a combination thereof whereby viridicatumtoxin, NSC 55636, NSC 123526, or a combination thereof reduces, inhibits, or abrogates activity of a poxvirus DNA polymerase.

In another embodiment, this invention provides a method of inhibiting, treating, or abrogating a poxvirus infection in a subject, comprising administering to the subject a compound having the formula I:

$$A\text{-}X\text{—}B \qquad \qquad I$$

wherein A is 1 of the following structures:

Q is $NCH_2CH_2R$ or O;
R is OH, $N(CH_3)_2$ or $CH_3$;
$R_1$ and R2 are independently, hydrogen, $CH_3$, OH, Cl;
$R_4$, $R_4'$ and $R_4''$ are independently, hydrogen, COOH, OH, $CF_3$, Cl, Br, COOMe, OMe, $N(CH_3)_2$ or $NO_2$;
W1 is alkyl, alky-isothiourea or substituted alkyl B is
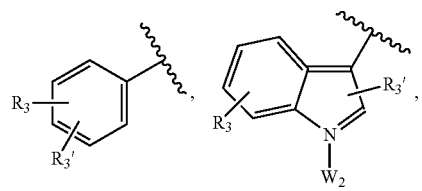
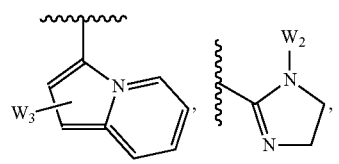
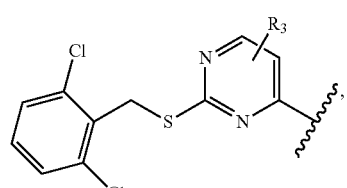
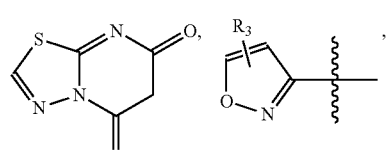
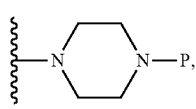
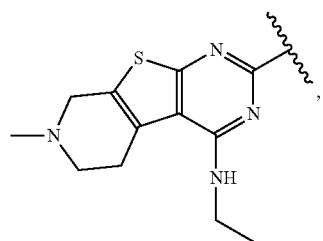
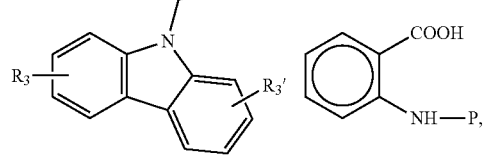
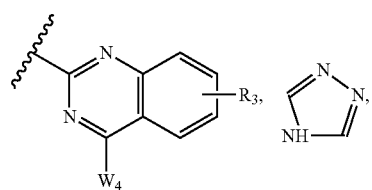
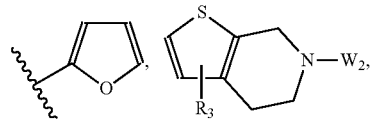
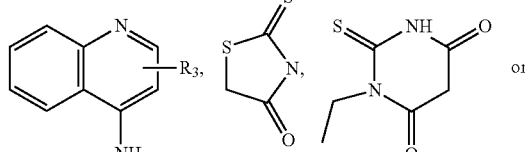
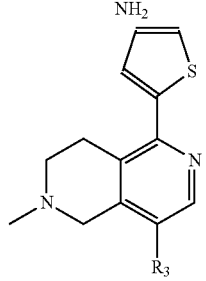
R$_3$ and R$_3$' are hydrogen, COOH, OH, COOMe, C$_1$, CF$_3$, CH$_3$, OCH$_3$, N(CH$_3$)$_2$ or CN;
W$_2$ is alkyl, alky-isothiourea or substituted alkyl, —SO2Et, H or isopropyl;
W$_3$ is 2,4 dimethoxy phenyl;
W$_4$ is CH$_3$ or NH—W$_3$; and
P is hydrogen, Fmoc, or Boc;
X is nothing, NH, S,
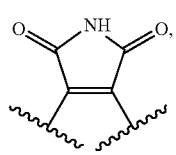 [SMILES: *C1=C(*)C(=O)NC1=O]
—CO—, —CH$_2$S—, —N═CH— —COO—, —OCO—,
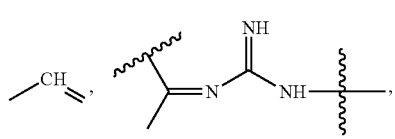
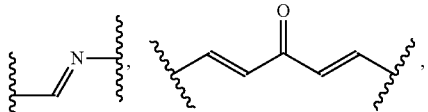
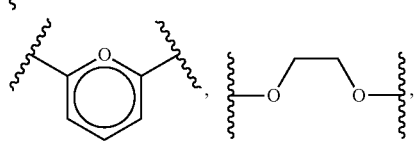
—CONH—, —NHCO—,
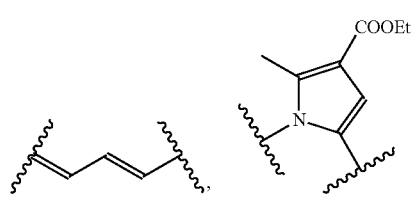

-continued
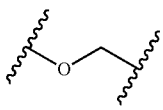
or A-X—B are fused rings, wherein X is a 5-membered substituted or not substituted heterocyclic or carbocyclic, optionally aromatic ring represented by the following structures:
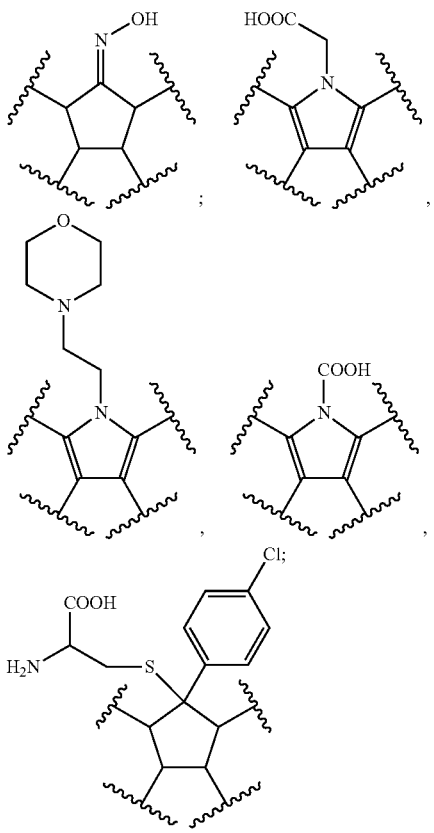
;

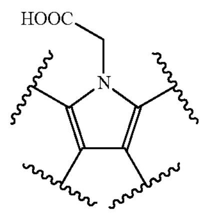

,

,

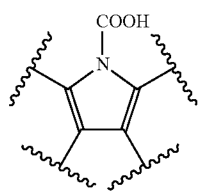

,

A is 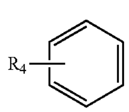 or
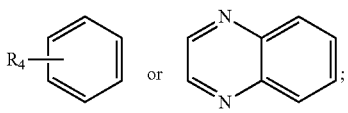
;

and
B is
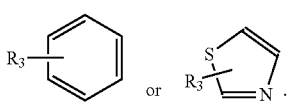
or

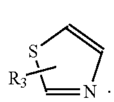

.

whereby the compound reduces, inhibits, or abrogates activity of a poxvirus DNA polymerase.

In another embodiment, this invention provides a method of inhibiting, treating, or abrogating a poxvirus infection in a subject, comprising contacting a poxvirus with a compound having the formula XXI, whereby the compound reduces, inhibits, or abrogates activity of a poxvirus DNA polymerase.

In another embodiment, this invention provides a method of inhibiting, treating, or abrogating a poxvirus infection in a subject, comprising contacting a poxvirus with a compound having the formula XXXII, whereby the compound reduces, inhibits, or abrogates activity of a poxvirus DNA polymerase.

In another embodiment, this invention provides a method of inhibiting, treating, or abrogating a poxvirus infection in a subject, comprising contacting a poxvirus with a compound having the formula XLI, whereby the compound reduces, inhibits, or abrogates activity of a poxvirus DNA polymerase.

In another embodiment, this invention provides a method of inhibiting, treating, or abrogating a poxvirus infection in a subject, comprising contacting a poxvirus with a mixture comprising compounds having the formula XXI, XXXII, XLI, whereby the compound reduces, inhibits, or abrogates activity of a poxvirus DNA polymerase.

In another embodiment, this invention provides a method of inhibiting, treating, or abrogating a poxvirus infection in a subject, comprising contacting a poxvirus with a compound having the formula XLIV, whereby the compound reduces, inhibits, or abrogates activity of a poxvirus DNA polymerase.

In another embodiment, the present invention provides a method of inhibiting replication of a poxvirus, comprising contacting a poxvirus with a compound of the formula:

Compound XLIV

In another embodiment, the present invention provides a method of inhibiting replication of a poxvirus, comprising contacting a poxvirus with a compound of formula XLIV.

In another embodiment, the present invention provides a method of inhibiting replication of a poxvirus, comprising contacting a poxvirus with a compound of the formula:

Compound XLV

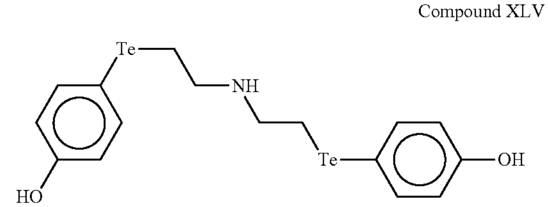

BRIEF DESCRIPTION OF THE DRAWINGS

The invention will be better understood from a reading of the following detailed description taken in conjunction with the drawings in which like reference designators are used to designate like elements, and in which:

FIG. 1. Flow-chart of stepwise screening protocol. In Step I, the NCI Diversity and Training Sets were screened using a lysate from vaccinia-infected cells. In Step II, the primary hits were screened to eliminate general and irrelevant inhibitors using the KSHV Pol8/PF8 DNA synthesis plate assay. In Step III, compounds were then tested on two distinct plate assays to differentiate polymerase from processive inhibitors. DNA synthesis inhibition by the hits was confirmed using an M13 assay (Step IV). The final four hits were tested for viral plaque reduction (Step V) and cellular cytotoxicity (Step VI). The screen yielded a polymerase and a processivity inhibitor of vaccinia virus DNA synthesis.

Figure 2:
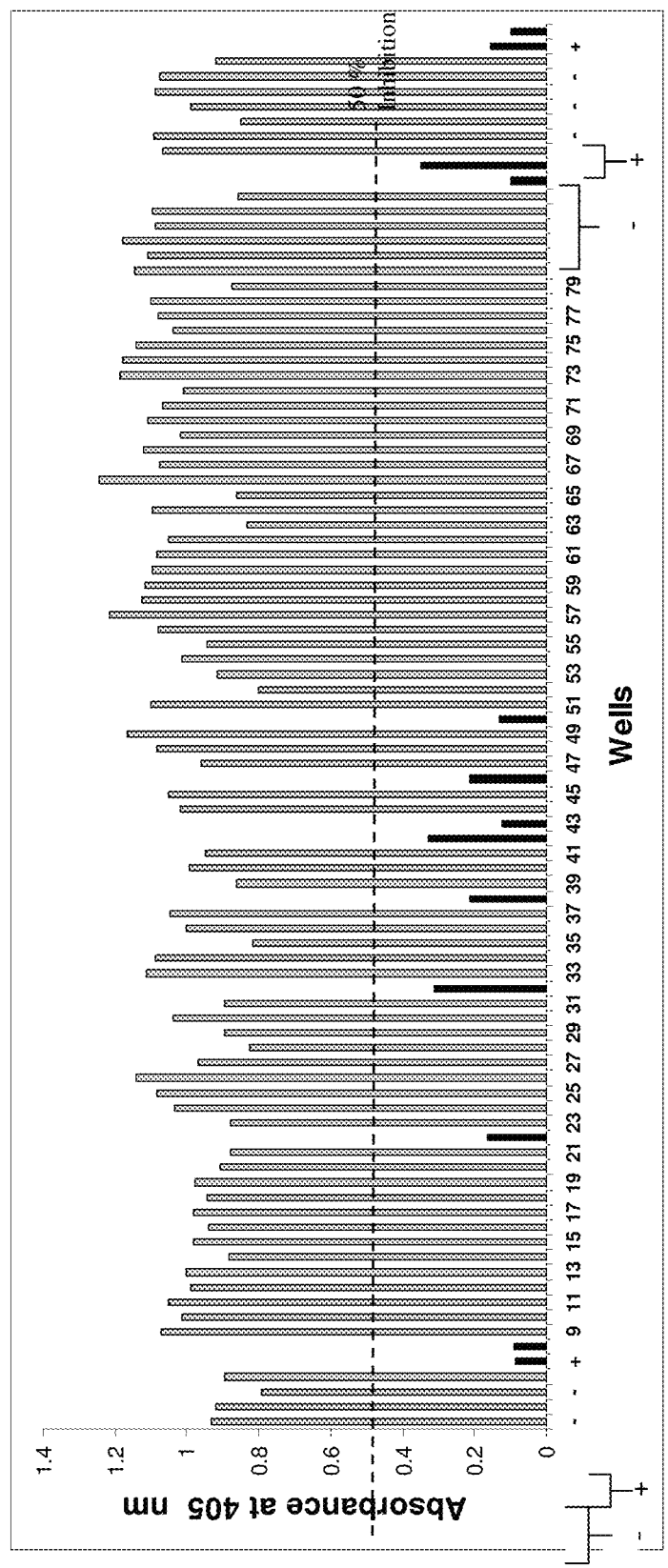

FIG. 2. A typical example of primary rapid plate assay result. Compounds that inhibited DNA synthesis by more than 50% are indicated by solid bars, and those that inhibit DNA synthesis by less than 50% are indicated by shaded bars. The (+) symbols indicate positive control inhibitor EDTA and the (−) symbol indicate negative control inhibitors unphosphorylated AZT, unphosphorylated acyclovir, DMSO alone and no compound added.

Figure 3:
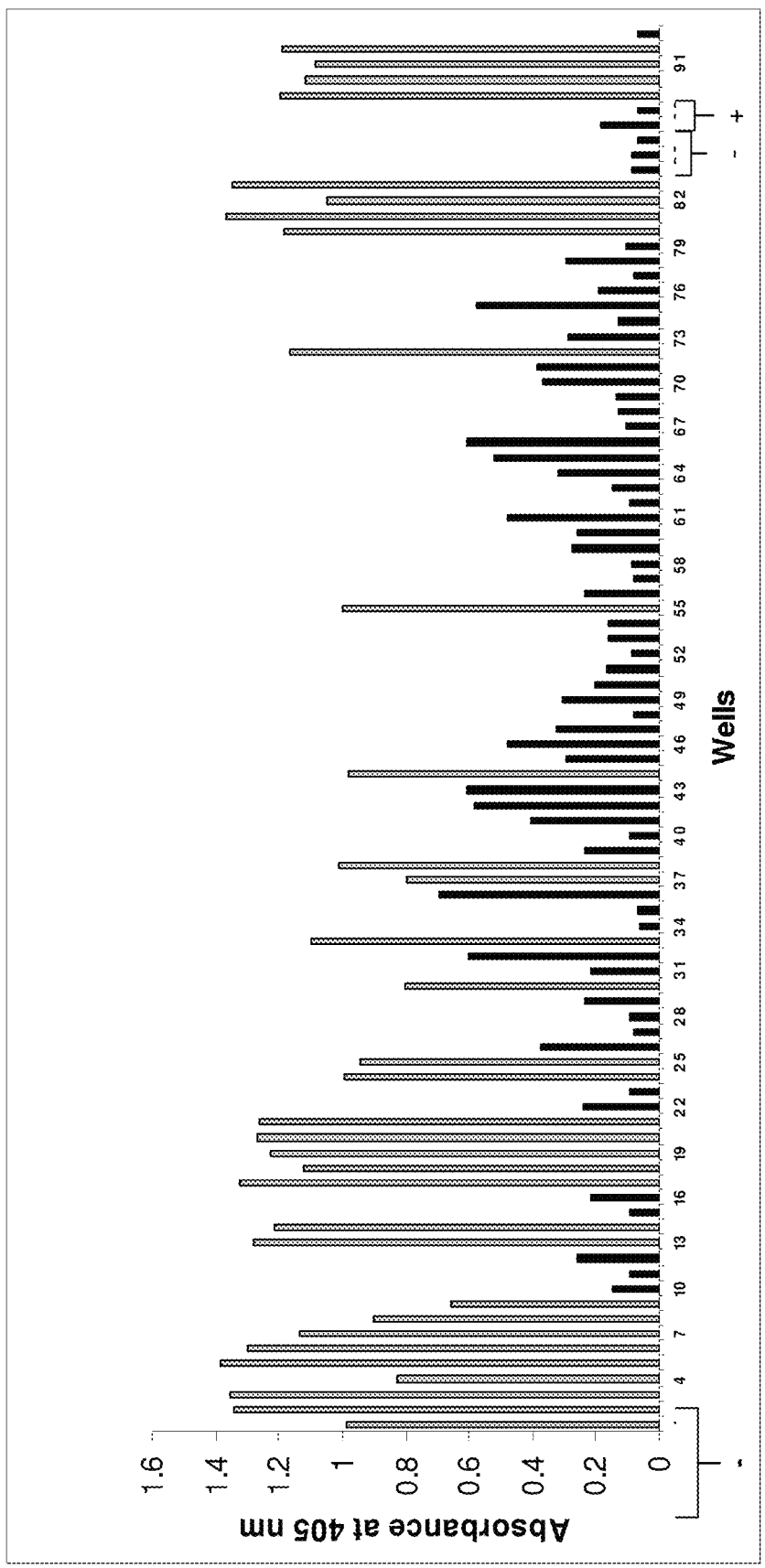

FIG. 3. Assay to eliminate general and irrelevant inhibitors. Hit compounds from the primary screen using vaccinia lysates were further tested in a KSHV rapid plate assay for their abilities to inhibit DNA synthesis directed by Pol8/PF8. Compounds that inhibited Pol8/PF8 DNA synthesis (solid bars) were categorized as general or irrelevant inhibitors. Compounds that failed to inhibit Pol8/PF8 DNA synthesis (shaded bars) were considered to be bonafide inhibitors of vaccinia DNA synthesis. The (+) symbol indicates positive control inhibitor EDTA and the (−) symbol indicates DMSO alone and no compound added.

FIG. 4. Assay to distinguish polymerase and processive inhibitors of vaccinia DNA synthesis. (A) The model depicts the uniform incorporation of the DIG-dUTP on a template by E9 polymerase under low salt conditions. Under low salt conditions, E9 incorporates dNTPs onto the DNA template to completion. (B) NCI hit compounds were analyzed on the uniform template in the presence of E9 alone under low salt conditions to identify polymerase inhibitors. Compounds 69343 and 55636 blocked polymerase activity whereas 123526 and 124808 had minimal effects. (C) The model depicts incorporation of the label DIG-dUTP on the distal end of the template by the triad (A20, D4, E9) under high salt conditions. Under high salt conditions, E9 requires A20 and D4 to accomplish processive DNA synthesis. (D) NCI hit compounds were analyzed on the distal template in the presence of the triad under high salt conditions to identify processivity inhibitors. Compounds 124808 and 123526 failed to block dNTP incorporation on the uniform template but blocked incorporation on the distal template. Compounds that block E9 polymerase activity also blocked processivity. For both A and C, the template 5' end is biotinylated for attachment to the streptavidin-coated plates.

Figure 5:
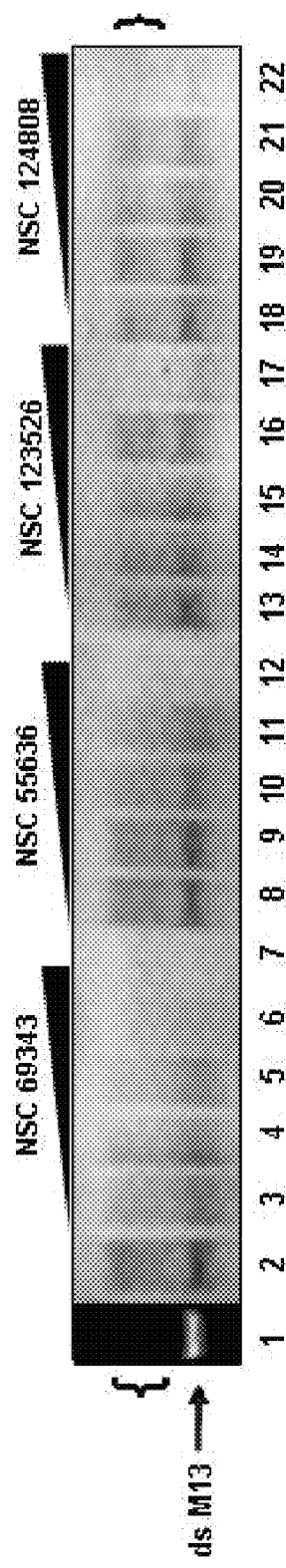

FIG. 5. Confirmation of inhibitors using the M13 DNA synthesis assay. Full-length ds DNA products labeled with [α-$^{32}$P]dCTP were synthesized from the M13 DNA primer/template in the presence of the vaccinia triad (A20, D4, E9) and examined on a non-denaturing gel. The ability of each polymerase and processivity inhibitor to block the M13 DNA synthesis was examined by adding increasing concentrations (100 nM, 1 µM, 10 µM, 100 µM and 1 mM) of each compound: NSC 69343, lanes 3-7; NSC 55636, lanes 8-12; NSC 123526, lanes 13-17; NSC 124808, lanes 18-22. Lane 1 shows the position of the full-length ds M13 DNA marker (arrow) as detected by cybergold. Lane 2 is the control reaction containing DMSO, the solvent for each of the compounds. The position of greater than unit length products are indicated by brackets.

Figure 6:
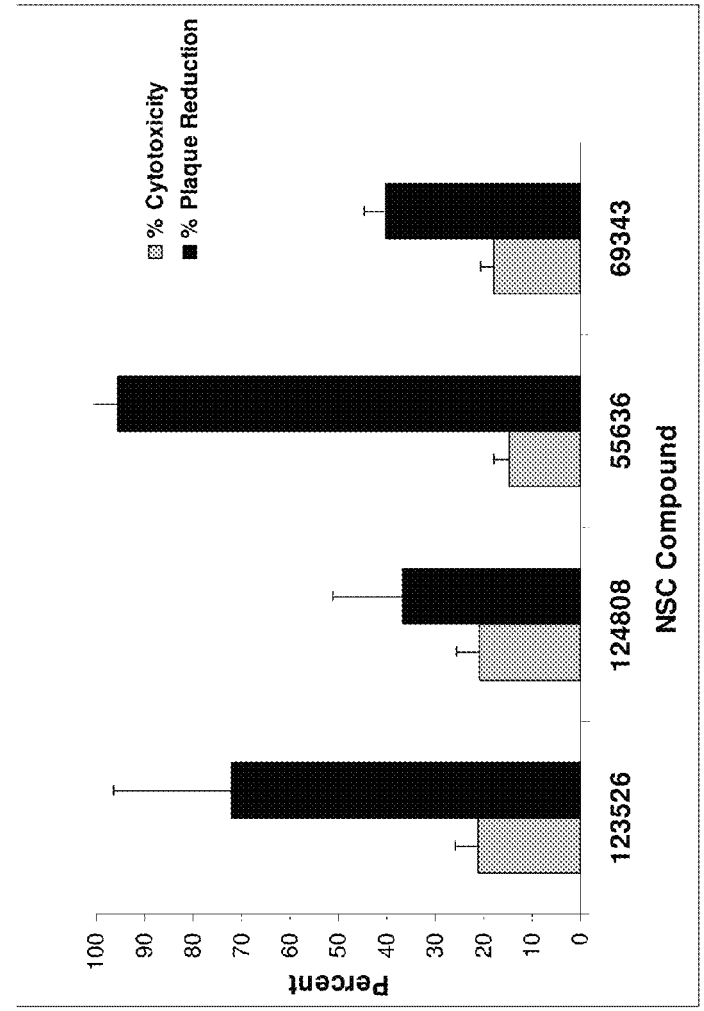

FIG. 6. Analysis of vaccinia DNA synthesis inhibitors by plaque reduction and cell cytotoxicity assays. The solid bars represent the reduction of plaques in the presence of inhibitors (100 µM) relative to no inhibitor. The shaded bars represent the percent cell cytotoxicity in the presence of inhibitors (100 µM) relative to no inhibitor. A minimum of six repetitions were performed for the cytotoxicity and the plaque reduction assays.

Figure 7:
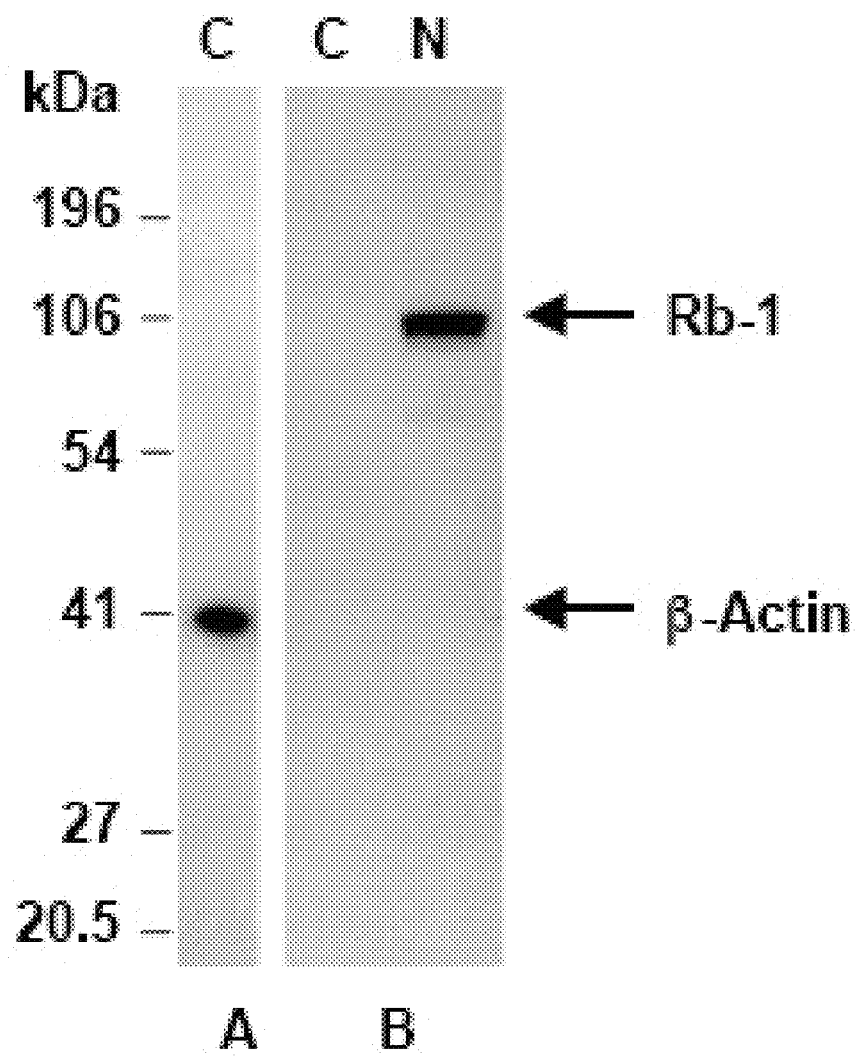

FIG. 7. Purity of the cytoplasmic extract of vaccinia virus-infected cells. (A) Western blot. Cytoplasmic and nuclear extracts of BSC-1 cells infected with vaccinia virus were analyzed by Western blot with monoclonal antibodies against the cytoplasmic marker β-Actin and the nuclear marker Rb-1. (B) DNA synthesis activities of cytoplasmic extracts in rapid plate assay. Lane 1: Reaction catalyzed by uninfected cytoplasmic extract. Lane 2: Reaction catalyzed by vaccinia-infected cytoplasmic extract. Lane 3: Reaction catalyzed by vaccinia-infected cytoplasmic extract that was completely inhibited with EDTA.

Figure 8:
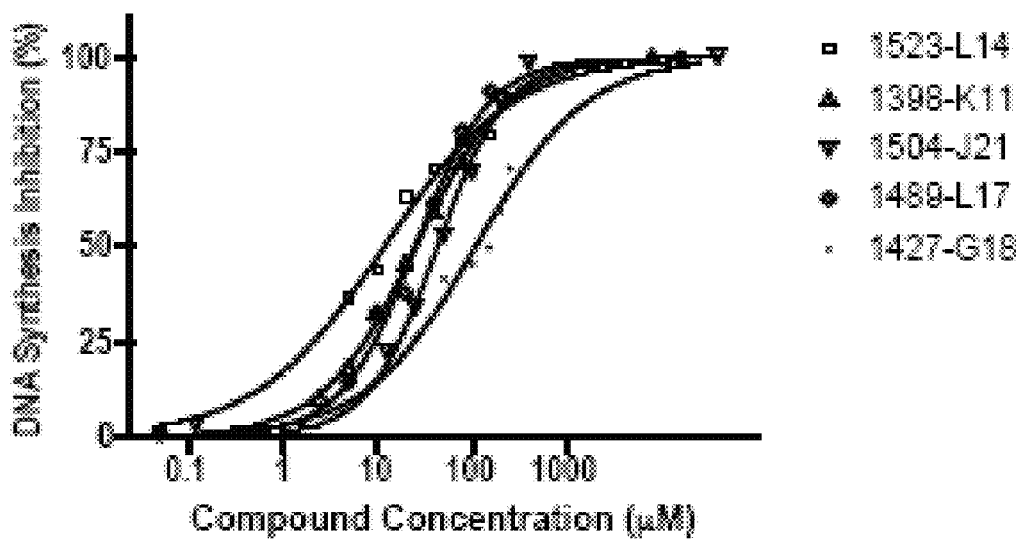
Figure 8:
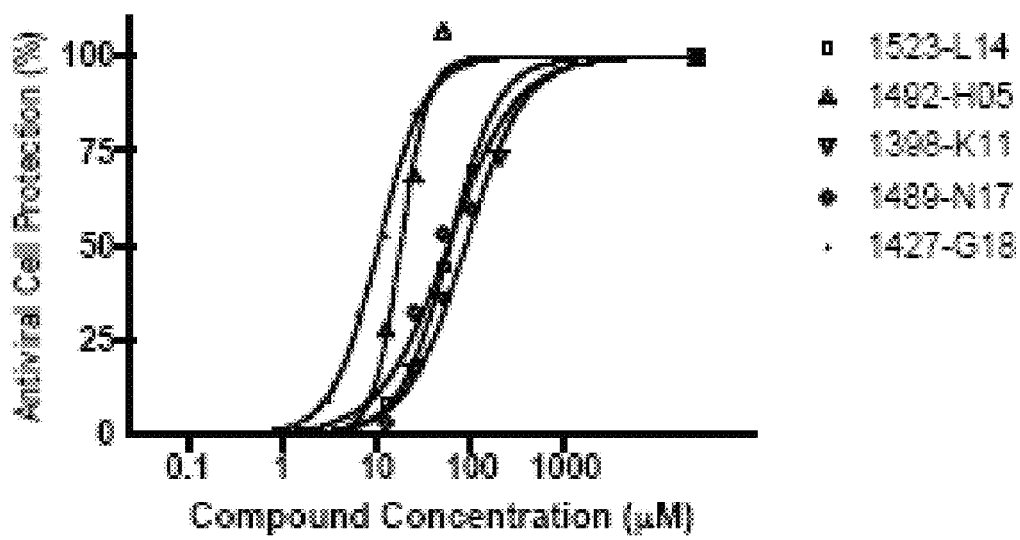

FIG. 8. Dose-dependent inhibition of vaccinia virus DNA synthesis by selected compounds. (IC50's in legend next to compound name.)

Figure 9:
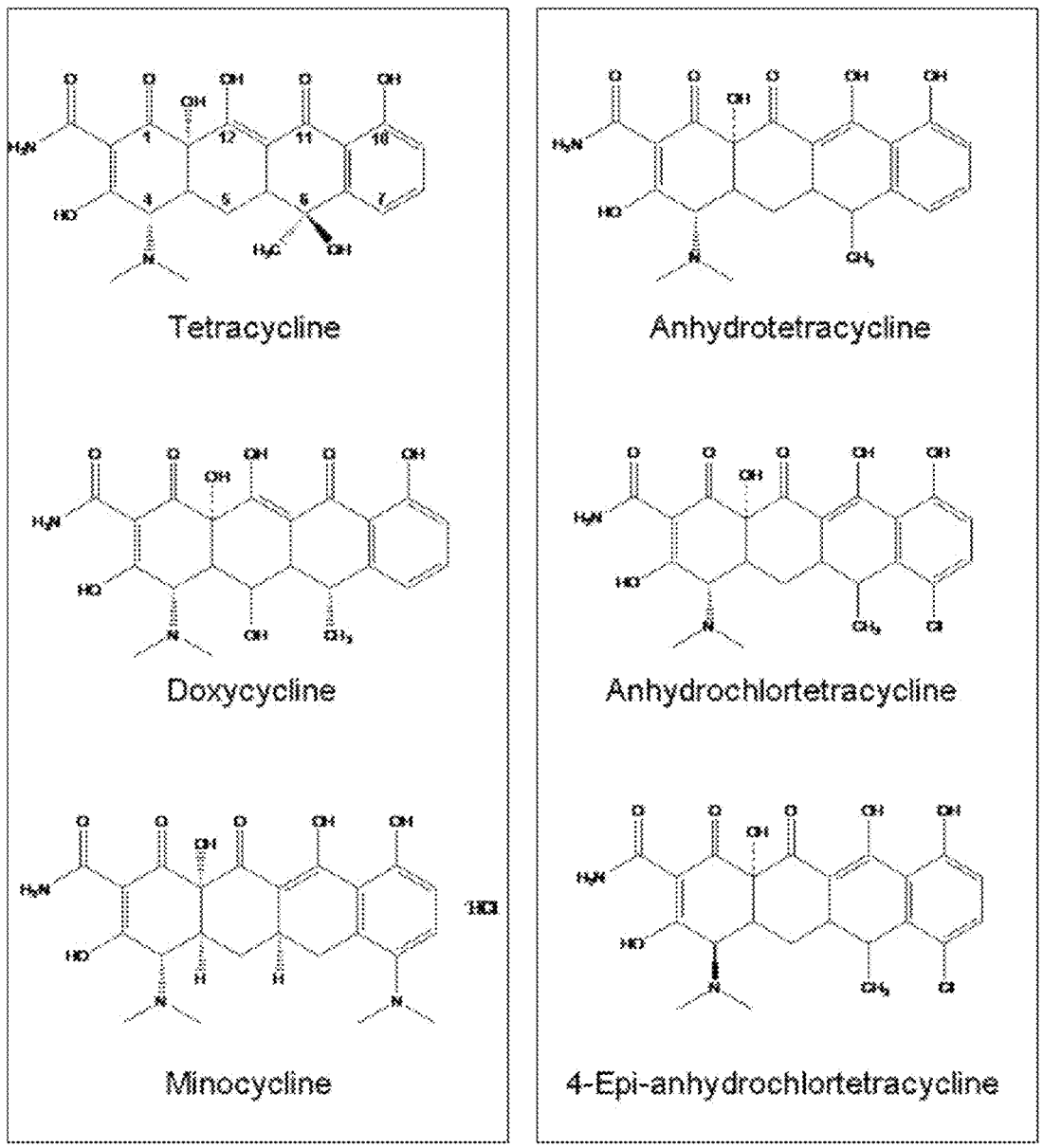

FIG. 9. Representative Class I and Class I tetracycline molecules.

Figure 10:
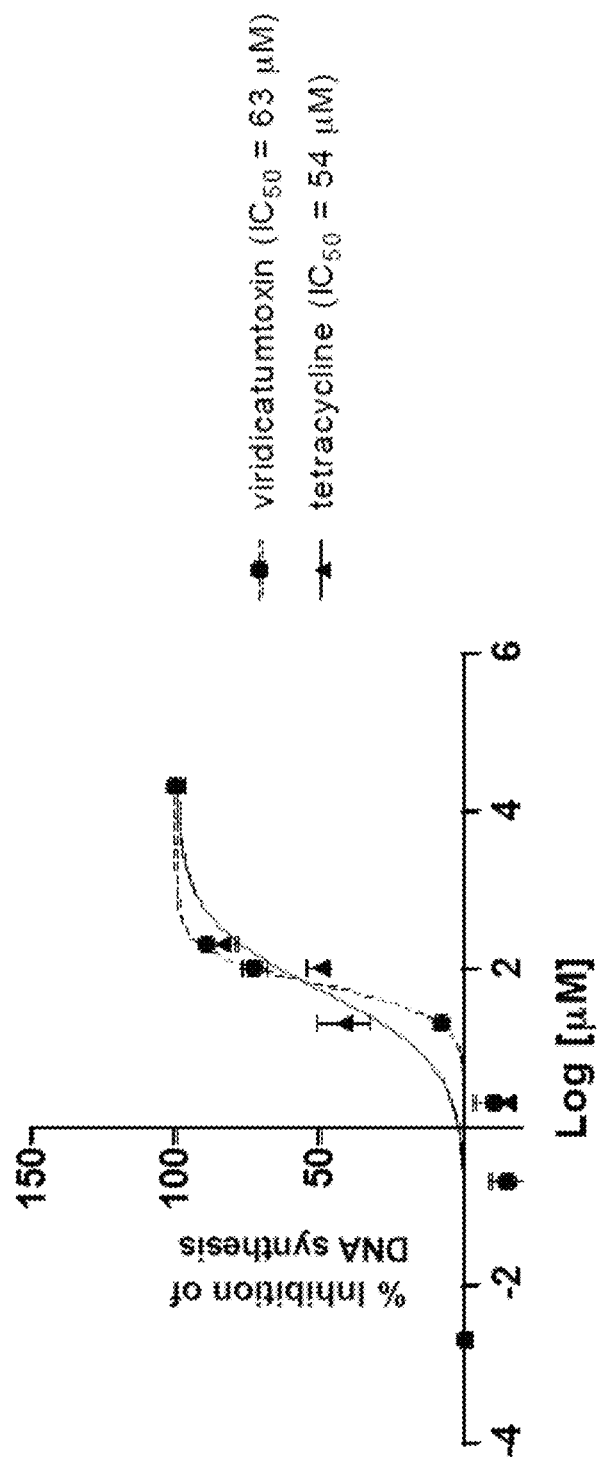

FIG. 10. Inhibition of vaccinia E9 polymerase-directed DNA synthesis by viridicatumtoxin and tetracycline. DNA synthesis was conducted in the rapid plate assay using low-salt conditions that favor extended strand synthesis of vaccinia E9 polymerase produced by in vitro translation. DNA synthesis activity was measured by the incorporation of DIG-dUTP into the newly synthesized strand. Increasing amounts of viridicatumtoxin (●) and tetracycline (▲) were added to the reactions, from which the (IC50) of each compound was determined.

Figure 11:
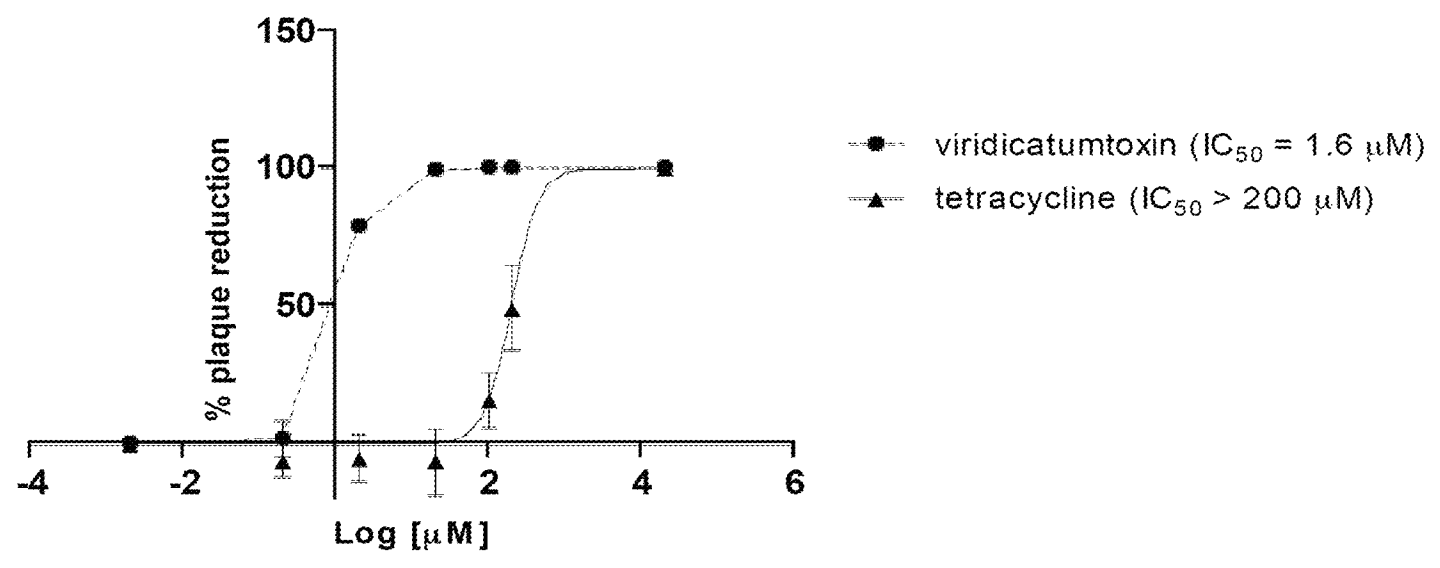

FIG. 11. Reduction of vaccinia virus plaques by viridicatumtoxin and tetracycline. Vaccinia virus infected BSC-1 cells were treated with increasing concentrations of viridicatumtoxin (♦) and tetracycline (▲) at one hour post infection. The cells were fixed, stained and the number of plaques were determined. The concentration of each compound required to reduce plaques by 50% ($IC_{50}$) was determined.

Figure 12:
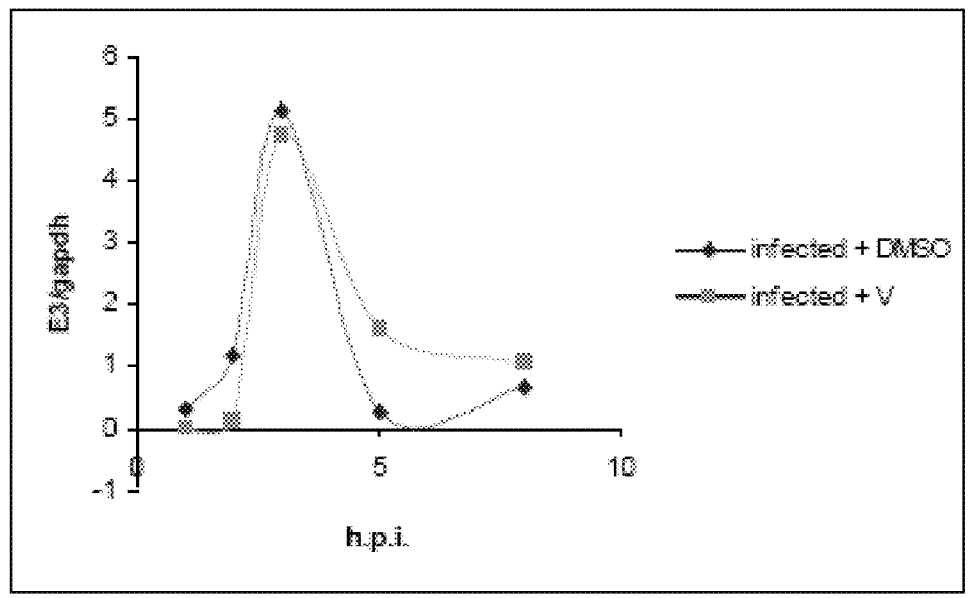
Figure 12:
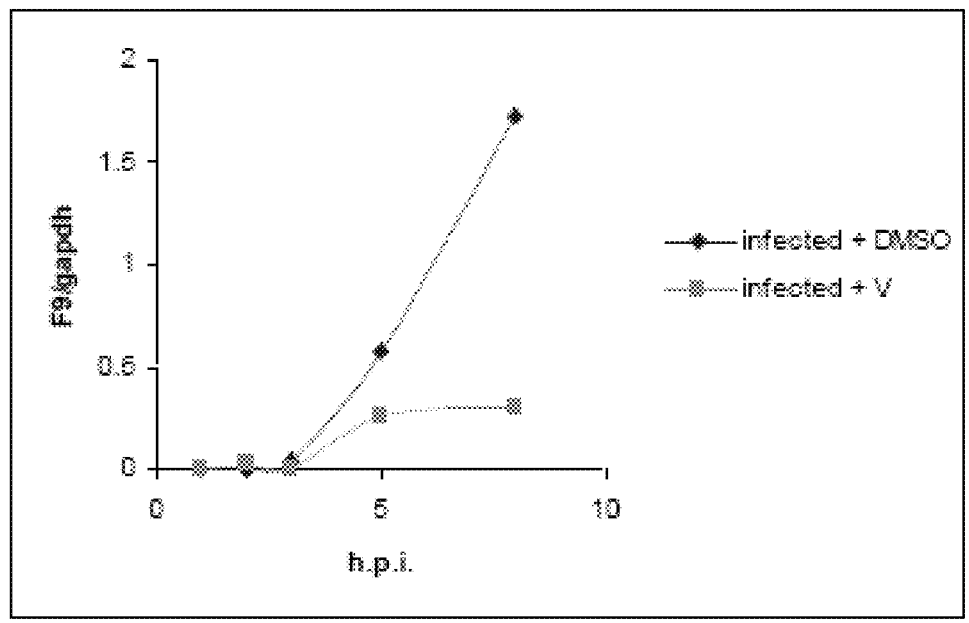

FIG. 12. Effect of viridicatumtoxin and tetracycline on vaccinia early and late viral mRNA expression. Total RNA was isolated from BSC-1 cells that were infected for 8 hr with vaccinia virus in the presence of 20 µM viridicatumtoxin or tetracycline. Vaccinia early gene E3 (A) and late gene F9 (B) were quantitated by RT-PCR and normalized to the levels of cellular gapdh. The data represents the average of duplicate experiments.

Figure 13:
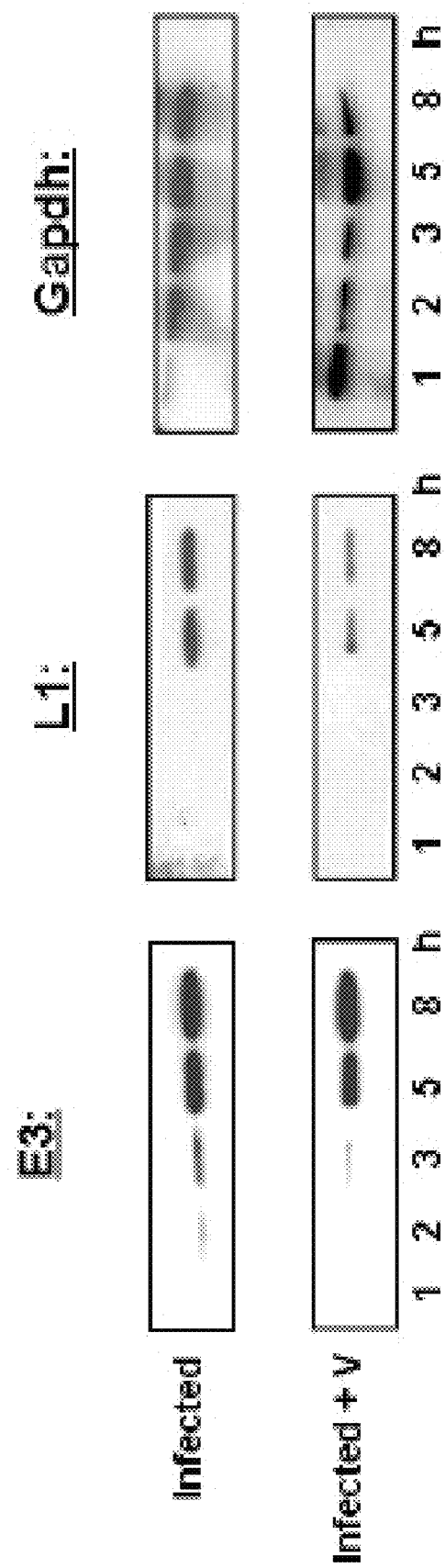

FIG. 13. Effect of viridicatumtoxin and tetracycline on vaccinia early and late viral protein expression. Lysates were prepared at different time points from BSC-1 cells that were infected with vaccinia virus in the presence of 20 µM viridicatumtoxin or tetracycline. The lysates were analyzed by western blot using vaccinia early E3 or late L1 protein antibodies as probes. The signal obtained with the GAPDH antibody served as an internal standard. Cells infected with DMSO alone served as a negative control.

Figure 14:
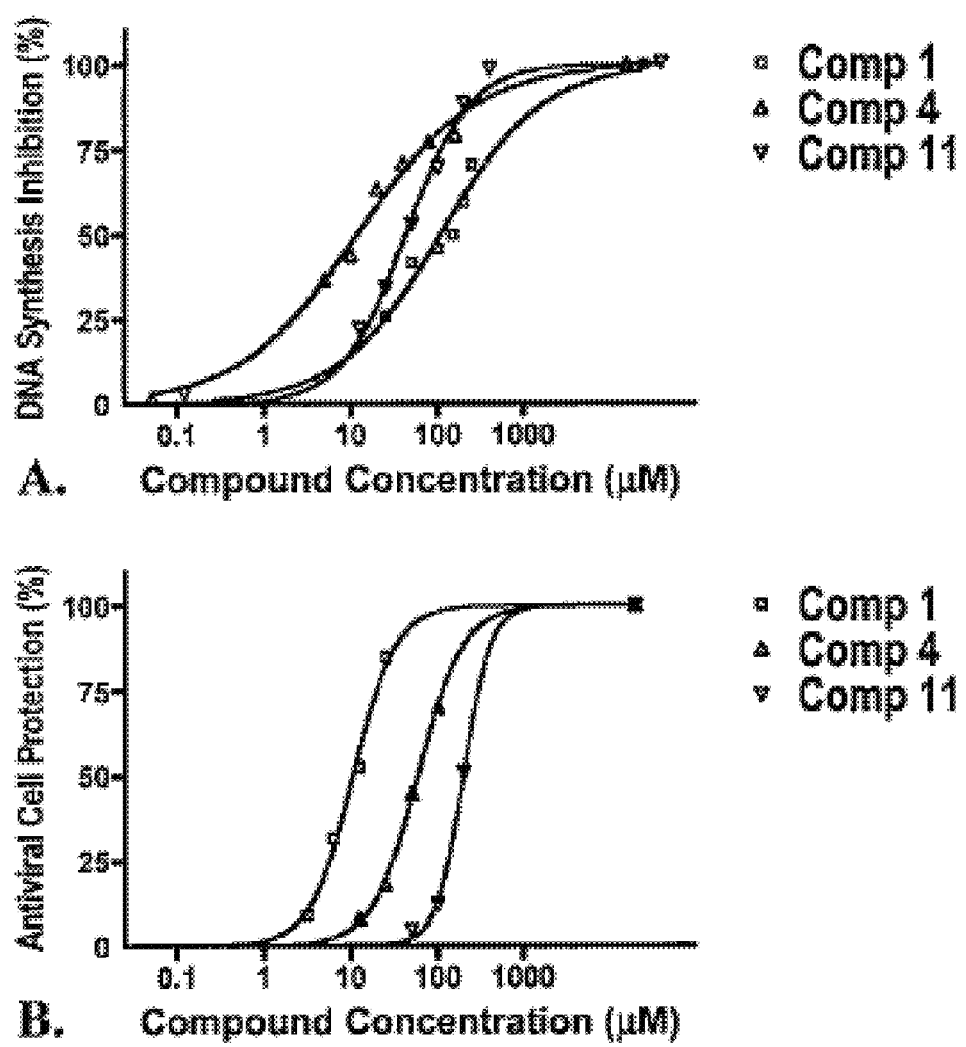

FIG. 14. Inhibition of vaccinia virus DNA synthesis and antiviral activity of 3 typical hit compounds. (A) Inhibition of vaccinia virus DNA synthesis by each compound was tested in triplicate over a range of concentrations in the DNA synthesis rapid plate assay. Percent inhibition was calculated relative to the uninhibited negative control (DMSO) and the completely inhibited positive control (EDTA). The Prism software was used to plot the inhibitory dose-response and to calculate the IC50 values. (B) Antiviral activity measured in the cell protection assay. The ability of compounds to block vaccinia virus infection in BS-C-1 cells was measured over a wide range of concentrations. Twenty hours after infection, cells were fixed with formaldehyde, stained with crystal violet, and the extent of antiviral protection was quantified by measuring absorbance at 570 nm. Every compound was tested in triplicate and the percent protection was calculated relative to the DMSO and uninfected controls. The Prism software was used to plot the protection dose-response and to calculate the EC50 values.

DETAILED DESCRIPTION OF THE INVENTION

The present invention provides methods of inhibiting, treating, or abrogating a poxvirus infection in a subject; inhibiting replication of a poxvirus; inhibiting activity of a poxvirus DNA polymerase; and decreasing processivity of a poxvirus DNA polymerase, comprising contacting a poxvirus with a compound of the present invention.

In another embodiment, the compound described herein is viridicatumtoxin. In another embodiment, viridicatumtoxin of the present invention has the following formula:

(Formula XLIV). In another embodiment, viridicatumtoxin reduces, inhibits, or abrogates activity of a poxvirus DNA polymerase. In In another embodiment, viridicatumtoxin reduces, inhibits, or abrogates interaction of a poxvirus DNA polymerase with its processivity factor.

In another embodiment, the compound as described herein is NSC 55636. In another embodiment, the compound NSC 55636 has the following formula:

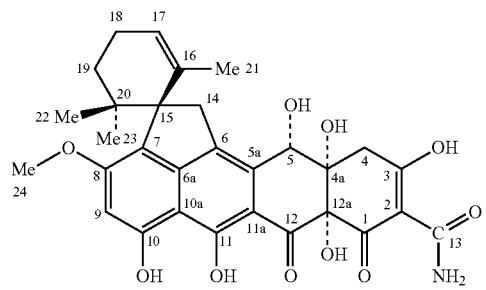

In another embodiment, NSC 55636 reduces, inhibits, or abrogates interaction of a poxvirus DNA polymerase with its processivity factor.

In another embodiment, the compound as described herein is NSC 123526. In another embodiment, the compound NSC 123526 has the following formula:

In another embodiment, NSC 123526 reduces, inhibits, or abrogates interaction of a poxvirus DNA polymerase with its processivity factor.

In certain embodiments, the compound as described herein has the structure of formula I:

$$A-X-B \qquad I$$

wherein A is:

or nothing

Q is $NCH_2CH_2R$ or O;

R is OH, $N(CH_3)_2$ or $CH_3$;

R1 and R2 are independently, hydrogen, $CH_3$, OH, Cl;

R4, R4' and R4" are independently hydrogen, COOH, OH, $CF_3$, Cl, Br, COOMe, OMe, $N(CH_3)_2$ or $NO_2$;

W1 is alkyl, alky-isothiourea or substituted alkyl;

B is
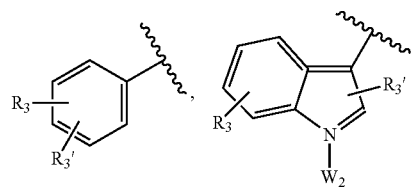
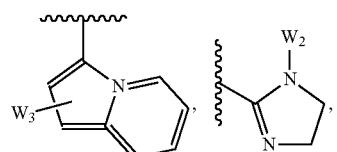
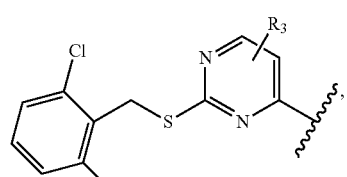
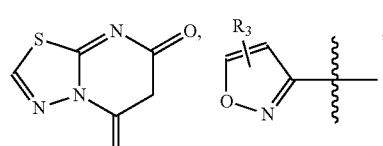
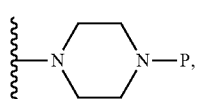
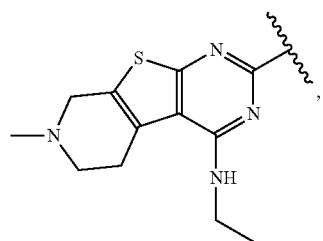
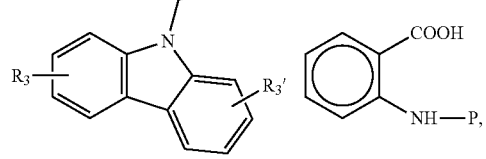
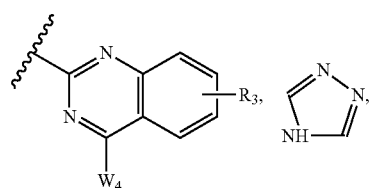
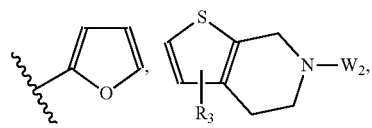
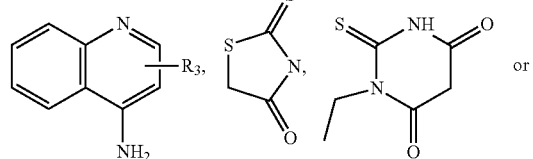
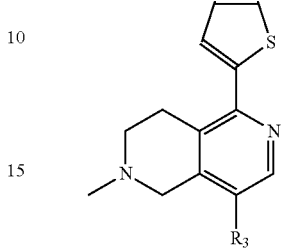
$R_3$ and $R_3'$ are hydrogen, COOH, OH, COOMe, $C_1$, $CF_3$, $CH_3$, $OCH_3$, $N(CH_3)_2$ or CN;
W2 is alkyl, alky-isothiourea or substituted alkyl, —SO2Et, H or isopropyl;
W3 is 2,4 dimethoxy phenyl;
W4 is $CH_3$ or NH—W3; and
P is hydrogen, Fmoc, or Boc;
X is nothing, $SO_2$, —$TeCH_2CH_2NHCH_2CH_2Te$—, NH, S,
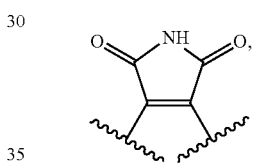
—CO—, —$CH_2S$—, —N=CH—, —COO—, —OCO—,
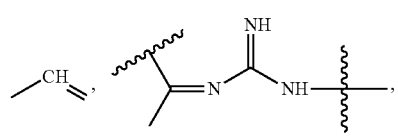
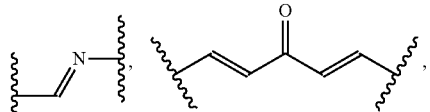
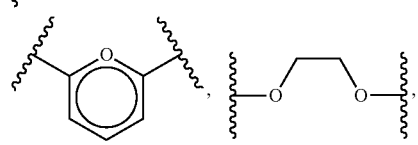
—CONH—, —NHCO—,
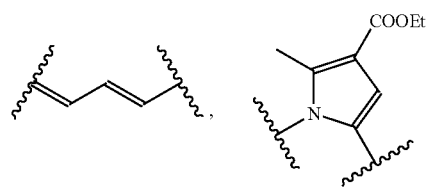

-continued
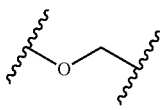
or A-X—B are fused rings, wherein X is a 5-membered substituted or not substituted heterocyclic or carbocyclic, optionally aromatic ring represented by one of the following structures:
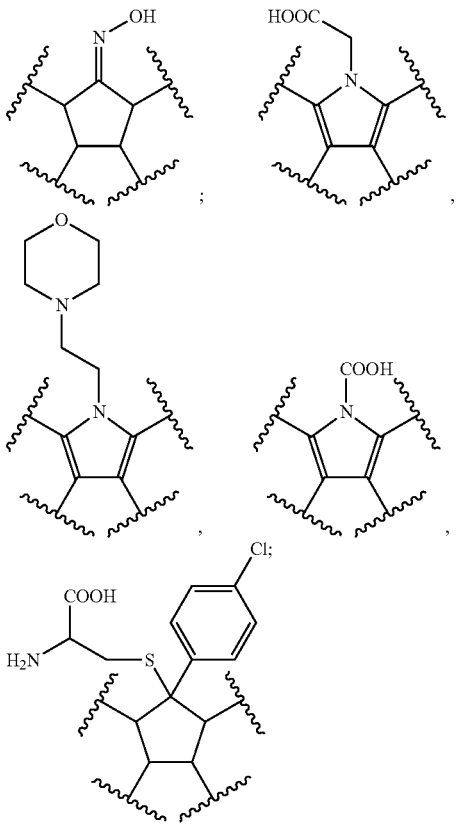
;

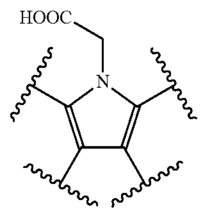

,

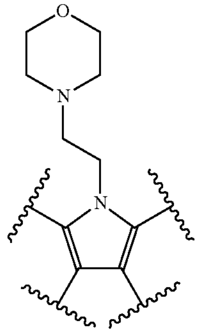

,

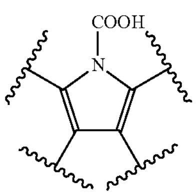

,

A 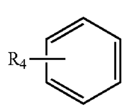 or
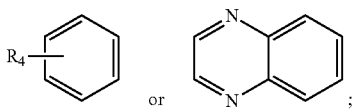
;

and
B is
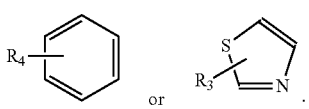
or

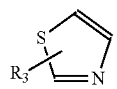

.

whereby the compound reduces, inhibits, or abrogates activity of a poxvirus DNA polymerase. In another embodiment, the compound reduces, inhibits, or abrogates interaction of a poxvirus DNA polymerase with its processivity factor.

In another embodiment, the present invention provides a method of inhibiting replication of a poxvirus, comprising contacting a poxvirus with a compound of the formula:

II 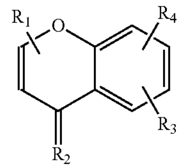 wherein R1 is phenyl substituted or non substituted by OH or CH=(heterocyclic 5-10 membered ring);

$R_2$ is O, NH, NR, wherein R is CH2CH2X;

X is OH, $CH_3$, $N(CH_3)_2$; and $R_3$ and R4 are independently H, Cl, $CH_3$ or OH.

In another embodiment, the present invention provides a method of inhibiting replication of a poxvirus, comprising contacting a poxvirus with viridicatumtoxin of the present invention.

In another embodiment, the present invention provides a method of inhibiting replication of a poxvirus, comprising contacting a poxvirus with NSC 55636 of the present invention.

In another embodiment, the present invention provides a method of inhibiting replication of a poxvirus, comprising contacting a poxvirus with NSC 123526 of the present invention.

In another embodiment, the present invention provides a method of inhibiting replication of a poxvirus, comprising contacting a poxvirus with a compound of the formula:

compound IV

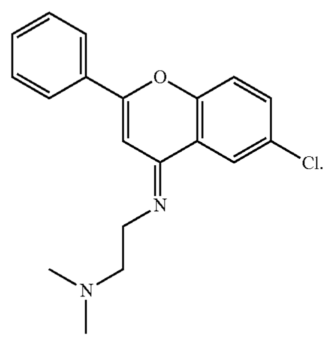

In another embodiment, the present invention provides a method of inhibiting replication of a poxvirus, comprising contacting a poxvirus with a compound of the formula:

compound V

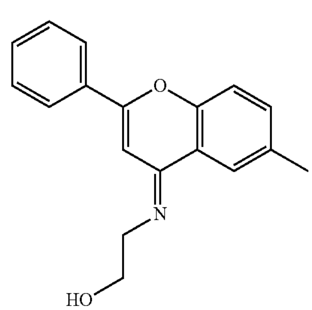

.

In another embodiment, the present invention provides a method of inhibiting replication of a poxvirus, comprising contacting a poxvirus with a compound of the formula:

compound VI

In another embodiment, the present invention provides a method of inhibiting replication of a poxvirus, comprising contacting a poxvirus with a compound of the formula:

compound VIII

In another embodiment, the heterocyclic 5-10 membered ring of formula II is:

In another embodiment, the present invention provides a method of inhibiting replication of a poxvirus, comprising contacting a poxvirus with a compound of the formula:

compound XVI

In another embodiment, the present invention provides a method of inhibiting replication of a poxvirus, comprising contacting a poxvirus with a compound of the formula:

III wherein A and B are independently hydrogen or they form a bond;
X is NH, Net, C=NOH, $CR_3R_4$;
R1' and R1 are independently $CF_3$, COOH, $COOCH_3$, $CH_3$, Cl, $OCH_3$, OH or CH=N-triazole;
R2' and R2 are independently $CF_3$, COOH, $COOCH_3$, $CH_3$, Cl, $OCH_3$, OH or CH=N-triazole; and
R3 and R4 are independently chlorobenzene or $SCH_2C(COOH)NH_2$.

In another embodiment, the present invention provides a method of inhibiting replication of a poxvirus, comprising contacting a poxvirus with a compound of the formula:

compound VII

In another embodiment, the present invention provides a method of inhibiting replication of a poxvirus, comprising contacting a poxvirus with a compound of the formula:

compound XI

In another embodiment, the present invention provides a method of inhibiting replication of a poxvirus, comprising contacting a poxvirus with a compound of the formula:

compound XXVII

In another embodiment, the present invention provides a method of inhibiting replication of a poxvirus, comprising contacting a poxvirus with a compound of the formula:

compound XXXIX

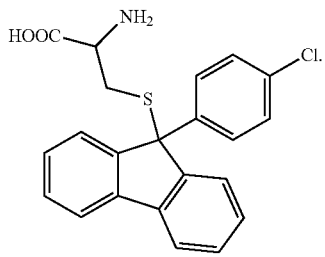

In another embodiment, the present invention provides a method of inhibiting replication of a poxvirus, comprising contacting a poxvirus with a compound of the formula:

compound XLIII

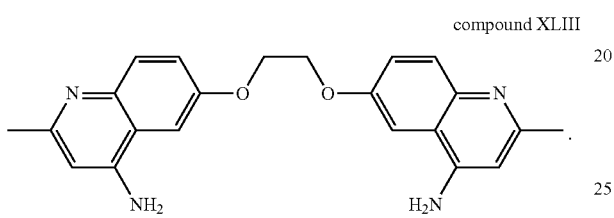

In another embodiment, the present invention provides a method of inhibiting replication of a poxvirus, comprising contacting a poxvirus with a compound of the formula:

compound XXXX

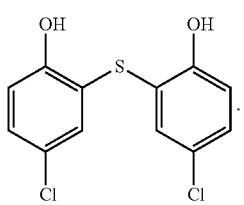 [SMILES: Oc1ccc(Cl)cc1Sc1cc(Cl)ccc1O]

In another embodiment, the present invention provides a method of inhibiting replication of a poxvirus, comprising contacting a poxvirus with a compound of the formula:

compound IX

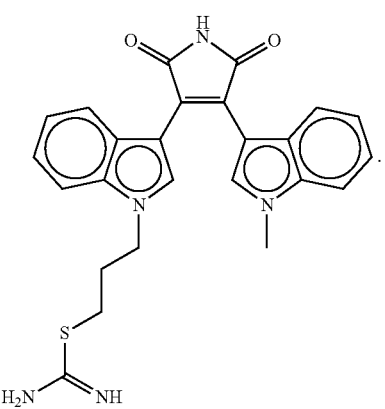

In another embodiment, the present invention provides a method of inhibiting replication of a poxvirus, comprising contacting a poxvirus with a compound of the formula:

compound X

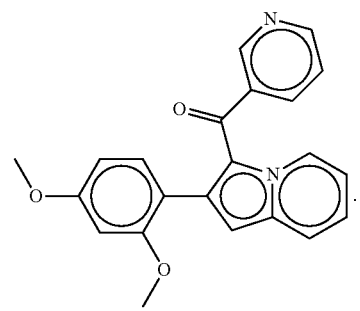

In another embodiment, the present invention provides a method of inhibiting replication of a poxvirus, comprising contacting a poxvirus with a compound of the formula:

compound XII

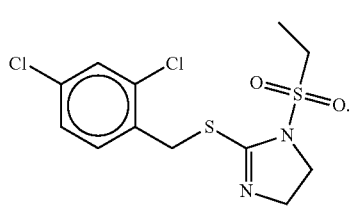

In another embodiment, the present invention provides a method of inhibiting replication of a poxvirus, comprising contacting a poxvirus with a compound of the formula:

compound XIII

In another embodiment, the present invention provides a method of inhibiting replication of a poxvirus, comprising contacting a poxvirus with a compound of the formula:

compound XIV

In another embodiment, the present invention provides a method of inhibiting replication of a poxvirus, comprising contacting a poxvirus with a compound of the formula:

compound XV

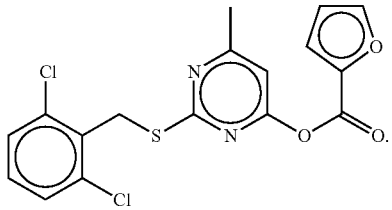

In another embodiment, the present invention provides a method of inhibiting replication of a poxvirus, comprising contacting a poxvirus with a compound of the formula:

compound XVII

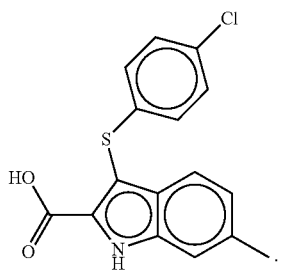

In another embodiment, the present invention provides a method of inhibiting replication of a poxvirus, comprising contacting a poxvirus with a compound of the formula:

compound XVIII

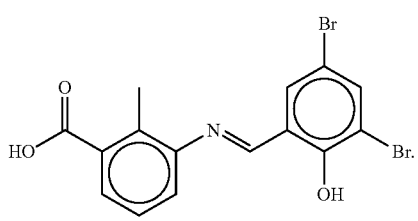

In another embodiment, the present invention provides a method of inhibiting replication of a poxvirus, comprising contacting a poxvirus with a compound of the formula:

compound XIX

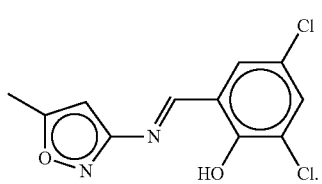

In another embodiment, the present invention provides a method of inhibiting replication of a poxvirus, comprising contacting a poxvirus with a compound of the formula:

compound XX

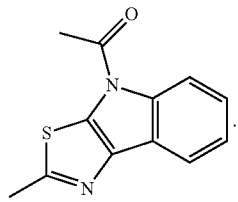

In another embodiment, the present invention provides a method of inhibiting replication of a poxvirus, comprising contacting a poxvirus with a compound of the formula:

compound XXII

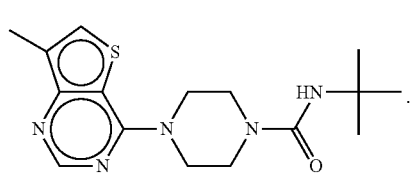

In another embodiment, the present invention provides a method of inhibiting replication of a poxvirus, comprising contacting a poxvirus with a compound of the formula:

compound XXIII

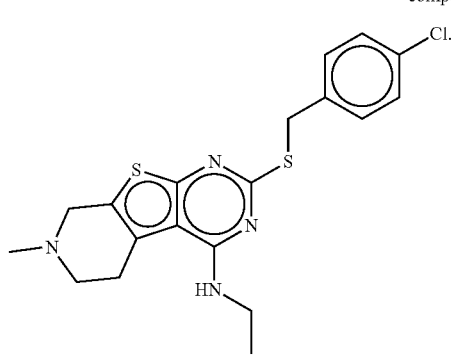

In another embodiment, the present invention provides a method of inhibiting replication of a poxvirus, comprising contacting a poxvirus with a compound of the formula:

compound XXIV

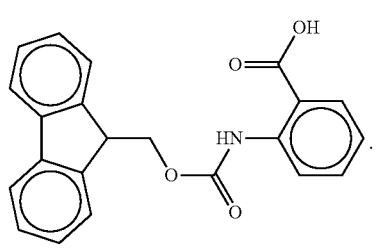

In another embodiment, the present invention provides a method of inhibiting replication of a poxvirus, comprising contacting a poxvirus with a compound of the formula:

compound XXV

In another embodiment, the present invention provides a method of inhibiting replication of a poxvirus, comprising contacting a poxvirus with a compound of the formula:

compound XXVI

In another embodiment, the present invention provides a method of inhibiting replication of a poxvirus, comprising contacting a poxvirus with a compound of the formula:

compound XXVIII

In another embodiment, the present invention provides a method of inhibiting replication of a poxvirus, comprising contacting a poxvirus with a compound of the formula:

compound XXIX

In another embodiment, the present invention provides a method of inhibiting replication of a poxvirus, comprising contacting a poxvirus with a compound of the formula:

compound XXX

In another embodiment, the present invention provides a method of inhibiting replication of a poxvirus, comprising contacting a poxvirus with a compound of the formula:

compound XXXI

In another embodiment, the present invention provides a method of inhibiting replication of a poxvirus, comprising contacting a poxvirus with a compound of the formula:

compound XXXIII

In another embodiment, the present invention provides a method of inhibiting replication of a poxvirus, comprising contacting a poxvirus with a compound of the formula:

compound XXXIV

In another embodiment, the present invention provides a method of inhibiting replication of a poxvirus, comprising contacting a poxvirus with a compound of the formula:

compound XXXV

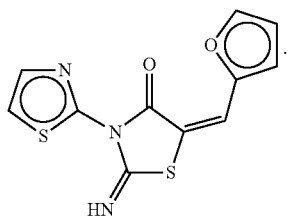

In another embodiment, the present invention provides a method of inhibiting replication of a poxvirus, comprising contacting a poxvirus with a compound of the formula:

compound XXXVI

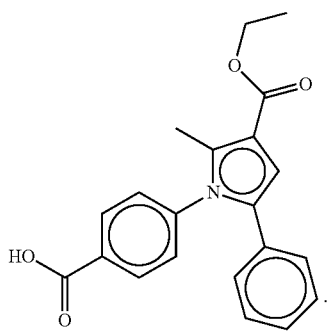

In another embodiment, the present invention provides a method of inhibiting replication of a poxvirus, comprising contacting a poxvirus with a compound of the formula:

compound XXXVII

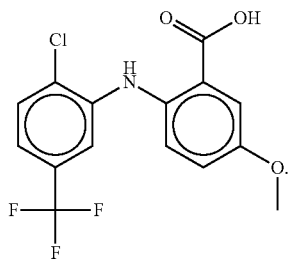

In another embodiment, the present invention provides a method of inhibiting replication of a poxvirus, comprising contacting a poxvirus with a compound of the formula:

Compound XXXVIII

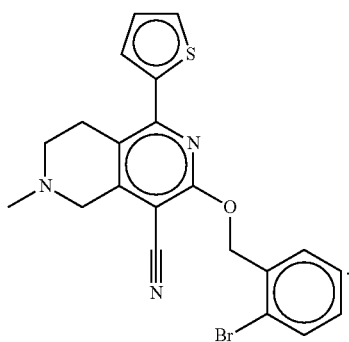

In another embodiment, the present invention provides a method of inhibiting replication of a poxvirus, comprising contacting a poxvirus with a compound of the formula:

Compound XLII

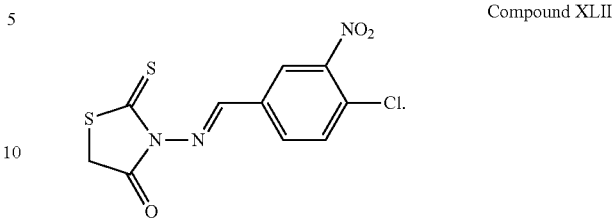

In another embodiment, the present invention provides a method of inhibiting replication of a poxvirus, comprising contacting a poxvirus with a compound of one of the following formulas:

Compound XXI

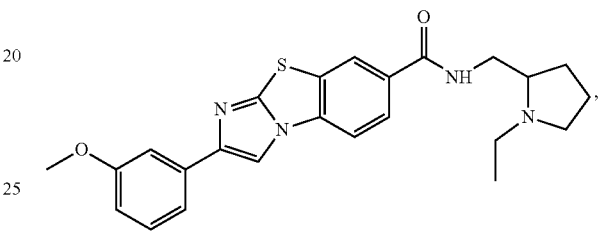

compound XXXII

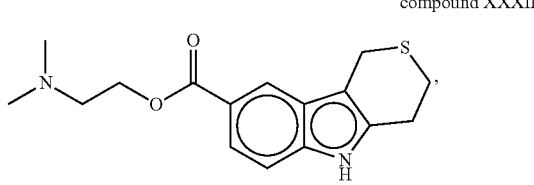

compound XLI

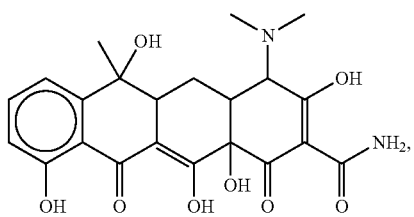

or a mixture thereof.

In another embodiment, the present invention provides a method of inhibiting replication of a poxvirus, comprising contacting a poxvirus with a compound of the formula:

Compound XLIV

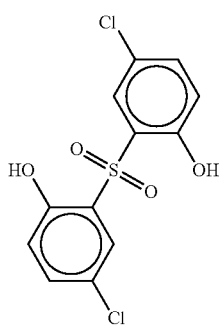

In another embodiment, the present invention provides a method of inhibiting replication of a poxvirus, comprising contacting a poxvirus with a compound of the formula:

Compound XLV

In another embodiment, viridicatumtoxin as described herein is synthesized by *P. viridicatum*. In another embodiment, viridicatumtoxin as described herein is synthesized by methods known to one skilled in the art.

In another embodiment, viridicatumtoxin as described herein has a poxvirus plaque IC50 of 400-1000 nM. In another embodiment, viridicatumtoxin as described herein has a poxvirus plaque IC50 of 400-500 nM. In another embodiment, viridicatumtoxin as described herein has a poxvirus plaque IC50 of 450-600 nM. In another embodiment, viridicatumtoxin as described herein has a poxvirus plaque IC50 of 500-750 nM. In another embodiment, viridicatumtoxin as described herein has a poxvirus plaque IC50 of 680-780 nM. In another embodiment, viridicatumtoxin as described herein has a poxvirus plaque IC50 of 780-1000 nM. In another embodiment, viridicatumtoxin as described herein has a poxvirus plaque IC50 of 750 nM. Each possibility represents a separate embodiment of the present invention.

In another embodiment, NSC 55636 as described herein has a poxvirus plaque IC50 of 400-1000 nM. In another embodiment, NSC 55636 as described herein has a poxvirus plaque IC50 of 400-500 nM. In another embodiment, NSC 55636 as described herein has a poxvirus plaque IC50 of 450-600 nM. In another embodiment, NSC 55636 as described herein has a poxvirus plaque IC50 of 500-750 nM. In another embodiment, NSC 55636 as described herein has a poxvirus plaque IC50 of 680-780 nM. In another embodiment, NSC 55636 as described herein has a poxvirus plaque IC50 of 780-1000 nM.

In another embodiment, NSC 123526 as described herein has a poxvirus plaque IC50 of 400-1000 nM. In another embodiment, NSC 123526 as described herein has a poxvirus plaque IC50 of 400-500 nM. In another embodiment, NSC 123526 as described herein has a poxvirus plaque IC50 of 450-600 nM. In another embodiment, NSC 123526 as described herein has a poxvirus plaque IC50 of 500-750 nM. In another embodiment, NSC 123526 as described herein has a poxvirus plaque IC50 of 680-780 nM. In another embodiment, NSC 55636 as described herein has a poxvirus plaque IC50 of 780-1000 nM.

In another embodiment, viridicatumtoxin as described herein has a poxvirus cell cytotoxicity-50 value (CC50) that is greater than 130 μM. In another embodiment, viridicatumtoxin as described herein has a poxvirus cell cytotoxicity-50 value (CC50) that is greater than 200 μM. In another embodiment, viridicatumtoxin as described herein has a poxvirus cell cytotoxicity-50 value (CC50) that is greater than 150 μM. In another embodiment, viridicatumtoxin as described herein has a poxvirus cell cytotoxicity-50 value (CC50) that is greater than 170 μM. In another embodiment, viridicatumtoxin as described herein has a poxvirus cell cytotoxicity-50 value (CC50) that is greater than 190 μM. In another embodiment, viridicatumtoxin as described herein has a poxvirus cell cytotoxicity-50 value (CC50) that is greater than 210 μM. In another embodiment, viridicatumtoxin as described herein has a poxvirus cell cytotoxicity-50 value (CC50) that is greater than 230 μM.

In one embodiment, viridicatumtoxin, is an effective inhibitor of vaccinia virus. In another embodiment, viridicatumtoxin interferes with vaccinia E9 DNA polymerase activity. In yet another embodiment, viridicatumtoxin reduces plaques at near nanomolar concentrations ($IC_{50}$ of 1.6 μM).

In one Viridicatumtoxin is not cytotoxic even when cells are exposed to 200 μM. In another embodiment, as described hereinbelow, the therapeutic index of viridicatumtoxin is greater than 125. In another embodiment, the therapeutic index of viridicatumtoxin is significantly higher than the therapeutic index of the DNA synthesis inhibitor cidofovir.

In one embodiment viridicatumtoxin prevents viral gene expression without affecting early viral genes. In another embodiment, viridicatumtoxin is nonteratogenic when orally administered to pregnant mice during mid-gestation.

In one embodiment, viridicatumtoxin, but not tetracycline, contains a spirocyclohexene moiety that imparts specificity through its bulk and stereochemistry. In another embodiment, viridicatumtoxin inhibits nucleotide incorporation in vivo In one embodiment, viridicatumtoxin is a novel non-nucleoside inhibitor of vaccinia virus DNA synthesis that is capable of blocking infection at concentrations that are not toxic to cells. In another embodiment, viridicatumtoxin is a used as a substrate for generating new and more potent poxvirus inhibitors.

In another embodiment, NSC 123526 as described herein has a poxvirus cell cytotoxicity-50 value ($CC_{50}$) that is greater than 130 μM. In another embodiment, NSC 123526 as described herein has a poxvirus cell cytotoxicity-50 value ($CC_{50}$) that is greater than 150 μM. In another embodiment, NSC 123526 as described herein has a poxvirus cell cytotoxicity-50 value ($CC_{50}$) that is greater than 170 μM. In another embodiment, NSC 123526 as described herein has a poxvirus cell cytotoxicity-50 value ($CC_{50}$) that is greater than 190 μM. In another embodiment, NSC 123526 as described herein has a poxvirus cell cytotoxicity-50 value ($CC_{50}$) that is greater than 210 μM. In another embodiment, NSC 123526 as described herein has a poxvirus cell cytotoxicity-50 value ($CC_{50}$) that is greater than 230 μM.

In another embodiment, NSC 55636 as described herein has a poxvirus cell cytotoxicity-50 value ($CC_{50}$) that is greater than 130 μM. In another embodiment, NSC 55636 as described herein has a poxvirus cell cytotoxicity-50 value ($CC_{50}$) that is greater than 150 μM. In another embodiment, NSC 55636 as described herein has a poxvirus cell cytotoxicity-50 value ($CC_{50}$) that is greater than 170 μM. In another embodiment, NSC 55636 as described herein has a poxvirus cell cytotoxicity-50 value ($CC_{50}$) that is greater than 190 μM. In another embodiment, NSC 55636 as described herein has a poxvirus cell cytotoxicity-50 value ($CC_{50}$) that is greater than 210 μM. In another embodiment, NSC 55636 as described herein has a poxvirus cell cytotoxicity-50 value ($CC_{50}$) that is greater than 230 μM.

In another embodiment, viridicatumtoxin as described herein has a poxvirus therapeutic index greater than 180. In another embodiment, viridicatumtoxin as described herein has a poxvirus therapeutic index greater than 200. In another embodiment, viridicatumtoxin as described herein has a poxvirus therapeutic index greater than 215. In another embodiment, viridicatumtoxin as described herein has a poxvirus therapeutic index greater than 240. In another embodiment, viridicatumtoxin as described herein has a poxvirus therapeutic index greater than 250. In another embodiment, viridicatumtoxin as described herein has a poxvirus therapeutic index greater than 270. In another embodiment, viridicatumtoxin as described herein has a poxvirus therapeutic index greater than 280.

In another embodiment, NSC 55636 as described herein has a poxvirus therapeutic index greater than 180. In another embodiment, NSC 55636 as described herein has a poxvirus therapeutic index greater than 200. In another embodiment, NSC 55636 as described herein has a poxvirus therapeutic index greater than 215. In another embodiment, NSC 55636 as described herein has a poxvirus therapeutic index greater than 240. In another embodiment, NSC 55636 as described herein has a poxvirus therapeutic index greater than 250. In another embodiment, NSC 55636 as described herein has a poxvirus therapeutic index greater than 270. In another embodiment, NSC 55636 as described herein has a poxvirus therapeutic index greater than 280.

In another embodiment, NSC 123526 as described herein has a poxvirus therapeutic index greater than 180. In another embodiment, NSC 123526 as described herein has a poxvirus therapeutic index greater than 200. In another embodiment, NSC 123526 as described herein has a poxvirus therapeutic index greater than 215. In another embodiment, NSC 123526 as described herein has a poxvirus therapeutic index greater than 240. In another embodiment, NSC 123526 as described herein has a poxvirus therapeutic index greater than 250. In another embodiment, NSC 123526 as described herein has a poxvirus therapeutic index greater than 270. In another embodiment, NSC 123526 as described herein has a poxvirus therapeutic index greater than 280.

In another embodiment, viridicatumtoxin is administered orally. In another embodiment, viridicatumtoxin is administered intraperitoneally (i.p.). In another embodiment, viridicatumtoxin is administered subcutaneously (s.c.) routes.

In another embodiment, NSC 123526 is administered orally. In another embodiment, NSC 123526 is administered intraperitoneally (i.p.). In another embodiment, NSC 123526 is administered subcutaneously (s.c.).

In another embodiment, NSC 55636 is administered orally. In another embodiment, NSC 55636 is administered intraperitoneally (i.p.). In another embodiment, NSC 55636 is administered subcutaneously (s.c.).

In another embodiment, the mice s.c. $LD_{50}$ of a compound as described herein are at least 100 mg/kg body weight. In another embodiment, the mice s.c. $LD_{50}$ of a compound as described herein are at least 150 mg/kg body weight. In another embodiment, the mice s.c. $LD_{50}$ of a compound as described herein are at least 200 mg/kg body weight. In another embodiment, the mice s.c. $LD_{50}$ of a compound as described herein are at least 250 mg/kg body weight. In another embodiment, the mice s.c. $LD_{50}$ of a compound as described herein are at least 300 mg/kg body weight. In another embodiment, the mice s.c. $LD_{50}$ of a compound as described herein are at least 350 mg/kg body weight. In another embodiment, the mice s.c. $LD_{50}$ of a compound as described herein are at least 380 mg/kg body weight. In another embodiment, the mice s.c. $LD_{50}$ of a compound as described herein are at least 400 mg/kg body weight. In another embodiment, the mice s.c. $LD_{50}$ of a compound as described herein are at least 450 mg/kg body weight.

In certain embodiments, the poxvirus as described herein infects vertebrates. In certain embodiments, the poxvirus as described herein infects invertebrates. In certain embodiments, the poxvirus of the present causes a variety of diseases of veterinary and medical importance. In certain embodiments, the poxvirus as described herein belongs to the chordopoxyirinae subfamily. In another embodiment, the poxvirus as described herein is variola virus (smallpox virus). In another embodiment, the poxvirus is vaccinia virus. In another embodiment, the poxvirus is molluscum contagiosum virus. In other embodiments, the poxvirus is any known orthopoxvirus, parapoxvirus, or yatapoxvirus.

In another embodiment, the poxvirus is a cowpox virus. In another embodiment, the poxvirus is a monkeypox virus. In another embodiment, the poxvirus is a raccoonpox virus. In another embodiment, the poxvirus is a camelpox virus. In another embodiment, the poxvirus is a skunkpox virus. In another embodiment, the poxvirus is a volepox virus. In another embodiment, the poxvirus is an ectromelia virus. In another embodiment, the poxvirus is a taterapox virus.

In another embodiment, the poxvirus is a parapoxvirus. In another embodiment, the poxvirus is an orf virus. In another embodiment, the poxvirus is a pseudocowpox virus. In another embodiment, the poxvirus is any other type of parapoxvirus known in the art.

In another embodiment, the poxvirus is an avipoxvirus. In another embodiment, the poxvirus is a canarypox virus. In another embodiment, the poxvirus is a fowlpox virus. In another embodiment, the poxvirus is any other type of avipoxvirus known in the art.

In another embodiment, the poxvirus is a capripoxvirus. In another embodiment, the poxvirus is a goatpox virus. In another embodiment, the poxvirus is a lumpy skin disease virus. In another embodiment, the poxvirus is any other type of capripoxvirus known in the art.

In another embodiment, the poxvirus is a leporipoxvirus. In another embodiment, the poxvirus is a myxoma virus. In another embodiment, the poxvirus is a fibroma virus. In another embodiment, the poxvirus is any other type of leporipoxvirus known in the art.

In another embodiment, the poxvirus is a molluscipoxvirus. In another embodiment, the poxvirus is a molluscum contagiosum virus. In another embodiment, the poxvirus is any other type of molluscipoxvirus known in the art.

In another embodiment, the poxvirus is a yatapoxvirus. In another embodiment, the poxvirus is a tanapox virus. In another embodiment, the poxvirus is a Yaba monkey tumor virus. In another embodiment, the poxvirus is any other type of yatapoxvirus known in the art.

In another embodiment, the poxvirus is any other type of poxvirus known in the art. In another embodiment, each of the above poxviruses and types of poxviruses represents a separate embodiment of the present invention.

In certain embodiments, methods of inhibiting replication of a poxvirus comprise methods of inhibiting the DNA thereof. In certain embodiments, inhibiting the DNA replication is achieved by inhibiting activity of a DNA polymerase protein. In certain embodiments, inhibiting a DNA polymerase protein activity comprises reducing the processivity of a DNA polymerase. Each possibility represents a separate embodiment of the present invention.

In another embodiment, the DNA polymerase that is inhibited is an E9 protein. In another embodiment, the DNA polymerase is a variola DNA polymerase. In another embodiment, the DNA polymerase has a sequence set forth in 1 of the following GenBank Accession Numbers: DQ437580; DQ437581; DQ437582; DQ437583-92, inclusive; DQ441416-48, inclusive.

In certain embodiments, DNA polymerase protein processive activity is inhibited in the presence of an accessory protein. In another embodiment, interaction of a DNA polymerase with an accessory protein is inhibited or reduced. In another embodiment, interaction of a DNA polymerase with a processivity factor is inhibited or reduced. In another embodiment, an E9 DNA polymerase processivity accessory protein or processivity factor is a stoichiometric component of the processive form of poxvirus DNA polymerase. In another embodiment, the accessory protein is an A20 protein. In another embodiment, the accessory protein is a D4R (D4; UDG). In another embodiment, the accessory protein is a D5 gene product. In another embodiment, the accessory protein is an H5 gene product. In another embodiment, the accessory protein is a homologue of A20 from another species. In another embodiment, the accessory protein is a homologue of D4 from another species. In another embodiment, the accessory protein is a homologue of D5 from another species. In another embodiment, the accessory protein is a homologue of H5 from another species. In another embodiment, the accessory protein is any other poxvirus DNA polymerase accessory protein known in the art. Each possibility represents a separate embodiment of the present invention.

In certain embodiments, the poxvirus E9 DNA polymerase protein is at least 70% homologous to a vaccinia virus E9 DNA polymerase protein sequence. In another embodiment, the homology is at least 75%. In another embodiment, the homology is at least 80%. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In another embodiment, the E9 DNA polymerase protein is a variola virus E9 DNA polymerase protein. In another embodiment, the E9 DNA polymerase protein is at least 80% homologous to variola virus E9 DNA polymerase protein. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In certain embodiments, the poxvirus E9 DNA polymerase processivity accessory protein is at least 70% homologous to vaccinia virus A20 protein sequence. In another embodiment, the homology is at least 75%. In another embodiment, the homology is at least 80%. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In another embodiment, the poxvirus E9 DNA polymerase processivity accessory protein is an A20 variola virus processivity accessory protein. In another embodiment, the poxvirus E9 DNA polymerase processivity accessory protein is at least 80% homologous to variola virus A20 protein sequence. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In certain embodiments, the poxvirus E9 DNA polymerase processivity accessory protein is at least 70% homologous to vaccinia virus D4R protein sequence. In another embodiment, the homology is at least 75%. In another embodiment, the homology is at least 80%. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In another embodiment, the poxvirus E9 DNA polymerase processivity accessory protein is a D4R variola virus processivity accessory protein. In another embodiment, the poxvirus E9 DNA polymerase processivity accessory protein is at least 80% homologous to a variola virus D4R protein sequence. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In certain embodiments, contacting a poxvirus with a compound as described herein comprises the step of adding the compound to a petri dish comprising cells infected with a poxvirus. In certain embodiments, contacting a poxvirus with a compound as described herein comprises adding the compound to a petri dish comprising an organ culture infected with a poxvirus. In certain embodiments, contacting a poxvirus with a compound as described herein comprises administering the compound to an animal and/or subject infected with a poxvirus.

In certain embodiments, a compound as described herein is solubilized in a buffer compatible with the media comprising cells or a tissue culture. In another embodiment, a compound as described herein is solubilized in the media comprising cells or a tissue culture. In certain embodiments, a compound as described herein is suspended or otherwise emulsified by methods known to one skilled in the art.

In certain embodiments, the present invention provides methods of inhibiting, a poxvirus infection in an animal and/or subject comprising administering to an animal and/or subject a compound of the present invention. In certain embodiments, the term inhibiting comprises restraining, holding back, repressing, or preventing.

In another embodiment, a compound utilized in methods as described herein has an $EC_{50}$ for a poxvirus of 4.8 μM. In another embodiment, the $EC_{50}$ is 0.05 μM. In another embodiment, the $EC_{50}$ is 0.1 μM. In another embodiment, the $EC_{50}$ is 0.15 μM. In another embodiment, the $EC_{50}$ is 0.2 μM. In another embodiment, the $EC_{50}$ is 0.3 μM. In another embodiment, the EC50 is 0.4 μM. In another embodiment, the $EC_{50}$ is 0.5 μM. In another embodiment, the $EC_{50}$ is 0.7 μM. In another embodiment, the EC50 is 1 μM. In another embodiment, the $EC_{50}$ is 1.5 μM. In another embodiment, the $EC_{50}$ is 2 μM. In another embodiment, the $EC_{50}$ is 3 μM. In another embodiment, the $EC_{50}$ is 5 μM. In another embodiment, the $EC_{50}$ is 7 μM. In another embodiment, the $EC_{50}$ is 10 μM. In another embodiment, the $EC_{50}$ is 15 μM. In another embodiment, the $EC_{50}$ is 16.1 μM. In another embodiment, the $EC_{50}$ is 20 μM. In another embodiment, the $EC_{50}$ is 30 μM. In another embodiment, the $EC_{50}$ is 50 μM. In another embodiment, the $EC_{50}$ is 70 μM.

In another embodiment, the $EC_{50}$ is 0.1-30 μM. In another embodiment, the $EC_{50}$ is 0.1-1 μM. In another embodiment, the $EC_{50}$ is 0.1-2 μM. In another embodiment, the $EC_{50}$ is 0.1-3 μM. In another embodiment, the $EC_{50}$ is 0.1-5 μM. In another embodiment, the $EC_{50}$ is 0.1-7 μM. In another embodiment, the $EC_{50}$ is 0.1-10 μM. In another embodiment, the $EC_{50}$ is 0.1-15 μM. In another embodiment, the $EC_{50}$ is 0.1-20 µM. In another embodiment, the $EC_{50}$ is 0.2-1 µM. In another embodiment, the $EC_{50}$ is 0.2-2 µM. In another embodiment, the $EC_{50}$ is 0.2-3 µM. In another embodiment, the $EC_{50}$ is 0.2-5 µM. In another embodiment, the $EC_{50}$ is 0.2-7 µM. In another embodiment, the $EC_{50}$ is 0.2-10 µM. In another embodiment, the $EC_{50}$ is 0.2-15 µM. In another embodiment, the $EC_{50}$ is 0.2-20 µM. In another embodiment, the $EC_{50}$ is 0.3-1 µM. In another embodiment, the $EC_{50}$ is 0.3-2 µM. In another embodiment, the $EC_{50}$ is 0.3-3 µM. In another embodiment, the $EC_{50}$ is 0.3-5 µM. In another embodiment, the $EC_{50}$ is 0.3-7 µM. In another embodiment, the $EC_{50}$ is 0.3-10 µM. In another embodiment, the $EC_{50}$ is 0.3-15 µM. In another embodiment, the $EC_{50}$ is 0.3-20 µM. In another embodiment, the $EC_{50}$ is 0.5-1 µM. In another embodiment, the $EC_{50}$ is 0.5-2 µM. In another embodiment, the $EC_{50}$ is 0.5-3 µM. In another embodiment, the $EC_{50}$ is 0.5-5 µM. In another embodiment, the $EC_{50}$ is 0.5-7 µM. In another embodiment, the $EC_{50}$ is 0.5-10 µM. In another embodiment, the $EC_{50}$ is 0.5-15 µM. In another embodiment, the $EC_{50}$ is 0.5-20 µM. In another embodiment, the $EC_{50}$ is 1-2 µM. In another embodiment, the $EC_{50}$ is 1-3 µM. In another embodiment, the $EC_{50}$ is 1-5 µM. In another embodiment, the $EC_{50}$ is 1-7 µM. In another embodiment, the $EC_{50}$ is 1-10 µM. In another embodiment, the $EC_{50}$ is 1-15 µM. In another embodiment, the $EC_{50}$ is 1-20 µM. In another embodiment, the $EC_{50}$ is 2-3 µM. In another embodiment, the $EC_{50}$ is 2-5 µM. In another embodiment, $EC_{50}$ EC50 is 2-7 µM. In another embodiment, the $EC_{50}$ is 2-10 µM. In another embodiment, the $EC_{50}$ is 2-15 µM. In another embodiment, the $EC_{50}$ is 2-20 µM. In another embodiment, the $EC_{50}$ is 2-30 µM. In another embodiment, the EC50 is 2-50 µM. In another embodiment, the $EC_{50}$ is 3-5 µM. In another embodiment, the $EC_{50}$ is 3-7 µM. In another embodiment, the $EC_{50}$ is 3-10 µM. In another embodiment, the $EC_{50}$ is 3-15 µM. In another embodiment, the $EC_{50}$ is 3-20 µM. In another embodiment, the $EC_{50}$ is 3-30 µM. In another embodiment, the $EC_{50}$ is 3-50 µM. In another embodiment, the $EC_{50}$ is 5-7 µM. In another embodiment, the $EC_{50}$ is 5-10 µM. In another embodiment, the $EC_{50}$ is 5-15 µM. In another embodiment, the $EC_{50}$ is 5-20 µM. In another embodiment, the $EC_{50}$ is 5-30 µM. In another embodiment, the $EC_{50}$ is 5-50 µM. In another embodiment, the $EC_{50}$ is 7-10 µM. In another embodiment, the $EC_{50}$ is 7-15 µM. In another embodiment, the $EC_{50}$ is 7-20 µM. In another embodiment, the $EC_{50}$ is 7-30 µM. In another embodiment, the $EC_{50}$ is 7-50 µM. In another embodiment, the $EC_{50}$ is 10-12 µM. In another embodiment, the $EC_{50}$ is 10-15 µM. In another embodiment, the $EC_{50}$ is 10-20 µM. In another embodiment, the $EC_{50}$ is 10-30 µM. In another embodiment, the $EC_{50}$ is 10-50 µM. In another embodiment, the $EC_{50}$ is 15-20 µM. In another embodiment, the $EC_{50}$ is 15-30 µM. In another embodiment, the $EC_{50}$ is 15-40 µM. In another embodiment, the $EC_{50}$ is 15-50 µM.

Each of the above values for $EC_{50}$ represents a separate embodiment of the present invention.

In certain embodiments, the present invention provides methods of treating a poxvirus infection in an animal and/or subject comprising administering to an animal and/or subject a compound of the present invention.

In certain embodiments, the present invention provides methods of abrogating a poxvirus infection in an animal and/or subject comprising administering to an animal and/or subject a compound of the present invention. In certain embodiments, the term abrogating comprises abolishing or terminating.

In certain embodiments, the compounds of this invention are formulated into a pharmaceutical dosage form. In certain embodiments, the pharmaceutical dosage form further comprises pharmaceutically acceptable carriers, excipients, emollients, stabilizers, etc., as are known in the pharmaceutical industry. In some embodiments the pharmaceutical dosage will include other active agents such immune system modifiers. In another embodiment, other compounds for stabilizing, preserving, the formulation and the like, but are not involved directly in the therapeutic effect of the indicated active ingredient, are included.

In certain embodiments, the pharmaceutical compositions containing the compounds as described herein are administered to a subject by any method known to a person skilled in the art, such as parenterally, paracancerally, transmucosally, transdermally, intramuscularly, intravenously, intradermally, subcutaneously, intraperitonealy, intraventricularly, intracranially, intravaginally or intratumorally.

Various embodiments of dosage ranges are contemplated by this invention. In one embodiment, the dosage of the compounds as described herein is in the range of 0.1-100 mg/day. In another embodiment, the dosage is in the range of 0.1-50 mg/day. In another embodiment, the dosage is in the range of 0.1-20 mg/day. In another embodiment, the dosage is in the range of 0.1-10 mg/day. In another embodiment, the dosage is in the range of 0.1-5 mg/day. In another embodiment, the dosage is in the range of 0.5-5 mg/day.

If the preferred mode is administered orally, in another embodiment, a unit dosage form comprises tablets, capsules, lozenges, chewable tablets, suspensions, emulsions and the like. In certain embodiments, such unit dosage forms comprise a safe and effective amount of the desired compound, or compounds, each of which is in another embodiment, from about 0.5 or 10 mg to about 300 mg/70 kg, or in another embodiment, about 0.5 or 10 mg to about 210 mg/70 kg. In certain embodiments, the pharmaceutically-acceptable carrier suitable for the preparation of unit dosage forms for peroral administration is well-known in the art. In certain embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In certain embodiments, glidants such as silicon dioxide can be used to improve flow characteristics of the powder-mixture. In certain embodiments, coloring agents, such as the FD&C dyes, can be added for appearance. In certain embodiments, sweeteners and flavoring agents, such as aspartame, saccharin, menthol, peppermint, and fruit flavors, are useful adjuvants for chewable tablets. In certain embodiments, capsules typically comprise one or more solid diluents disclosed above. In certain embodiments, the selection of carrier components depends on secondary considerations like taste, cost, and shelf stability, which are not critical for the purposes of this invention, and can be readily made by a person skilled in the art.

In certain embodiments, peroral compositions comprise liquid solutions, emulsions, suspensions, and the like. In certain embodiments, the pharmaceutically-acceptable carriers suitable for preparation of such compositions are well known in the art. In certain embodiments, liquid oral compositions comprise, in certain embodiments, from about 0.012% to about 0.933% of the desired compound or compounds, or in another embodiment, from about 0.033% to about 0.7%.

In another embodiment, the dosage is 10-20 µg/tablet. In another embodiment, the dosage is 20-30 µg/tablet. In another embodiment, the dosage is 20-40 µg/tablet. In another embodiment, the dosage is 30-60 µg/tablet. In another embodiment, the dosage is 40-80 µg/tablet. In another embodiment, the dosage is 50-100 μg/tablet. In another embodiment, the dosage is 50-150 μg/tablet. In another embodiment, the dosage is 100-200 μg/tablet. In another embodiment, the dosage is 200-300 μg/tablet. In another embodiment, the dosage is 300-400 μg/tablet. In another embodiment, the dosage is 400-600 μg/tablet. In another embodiment, the dosage is 500-800 μg/tablet. In another embodiment, the dosage is 800-1000 μg/tablet. In another embodiment, the dosage is 1000-1500 μg/tablet. In another embodiment, the dosage is 1500-2000 μg/tablet. In another embodiment, the dosage is 2-3 mg/tablet. In another embodiment, the dosage is 2-5 mg/tablet. In another embodiment, the dosage is 2-10 mg/tablet. In another embodiment, the dosage is 2-20 mg/tablet. In another embodiment, the dosage is 2-30 mg/tablet. In another embodiment, the dosage is 2-50 mg/tablet. In another embodiment, the dosage is 2-80 mg/tablet. In another embodiment, the dosage is 2-100 mg/tablet. In another embodiment, the dosage is 3-10 mg/tablet. In another embodiment, the dosage is 3-20 mg/tablet. In another embodiment, the dosage is 3-30 mg/tablet. In another embodiment, the dosage is 3-50 mg/tablet. In another embodiment, the dosage is 3-80 mg/tablet. In another embodiment, the dosage is 3-100 mg/tablet. In another embodiment, the dosage is 5-10 mg/tablet. In another embodiment, the dosage is 5-20 mg/tablet. In another embodiment, the dosage is 5-30 mg/tablet. In another embodiment, the dosage is 5-50 mg/tablet. In another embodiment, the dosage is 5-80 mg/tablet. In another embodiment, the dosage is 5-100 mg/tablet. In another embodiment, the dosage is 10-20 mg/tablet. In another embodiment, the dosage is 10-30 mg/tablet. In another embodiment, the dosage is 10-50 mg/tablet. In another embodiment, the dosage is 10-80 mg/tablet. In another embodiment, the dosage is 10-100 mg/tablet.

In one embodiments, compositions for use in the methods of this invention comprise solutions or emulsions, which in another embodiment are aqueous solutions or emulsions comprising a safe and effective amount of a compound as described herein and in yet another embodiment, other compounds. In one embodiment, such compositions comprise from about 0.01% to about 10.0% w/v of a subject compound, more preferably from about 0.1% to about 5.0, which in another embodiment, is used for the systemic delivery of compounds by a route known to one skilled in the art.

In certain embodiments, the compositions comprise dry powders. In certain embodiments, compositions are formulated for atomization and/or inhalation administration. In certain embodiments, such compositions are contained in a container with attached atomizing means.

Further, in another embodiment, the pharmaceutical compositions are administered by intravenous, intra-arterial, or intramuscular injection of a liquid preparation. In certain embodiments, suitable liquid formulations include solutions, suspensions, dispersions, emulsions, oils and the like. In another embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

In another embodiment, the active compound can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327).

In another embodiment, the pharmaceutical composition delivered in a controlled release system is formulated for intravenous infusion, implantable osmotic pump, transdermal patch, liposomes, or other modes of administration. In another embodiment, a pump may be used (see Langer, supra; Sefton, CRC Crit. Ref. *Biomed. Eng.* 14:201 (1987); Buchwald et al., Surgery 88:507 (1980); Saudek et al., *N. Engl. J. Med.* 321:574 (1989). In another embodiment, polymeric materials can be used. In yet one embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (*Science* 249:1527-1533 (1990).

In certain embodiments, the preparation of pharmaceutical compositions which contain active components is well understood in the art, for example by mixing, granulating, or tablet-forming processes. In certain embodiments, the active therapeutic ingredients are mixed with excipients which are pharmaceutically acceptable and compatible with the active ingredient. In certain embodiments, for oral administration, the compounds as described herein or their physiologically tolerated derivatives such as salts, esters, N-oxides, and the like and additional therapeutic agent or agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

In certain embodiments, an active component as described herein is formulated into the composition as neutralized pharmaceutically acceptable salt forms. In certain embodiments, pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. In certain embodiments, salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In certain embodiments, for use in medicine, the salts of the compounds as described herein will be pharmaceutically acceptable salts. In certain embodiments, other salts may, however, be useful in the preparation of the compounds used in the methods described herein, or of their pharmaceutically acceptable salts. In certain embodiments, suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In certain embodiments, the compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents;

viscosity adjustors, such as polymers, including cellulose and derivatives thereof; and polyvinyl alcohol and acids and bases to adjust the pH of these aqueous compositions as needed. In certain embodiments, the compositions may also comprise local anesthetics or other actives. In certain embodiments, the compositions can be used as sprays, mists, drops, and the like.

In certain embodiments, substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. In certain embodiments, the choice of a pharmaceutically-acceptable carrier to be used in conjunction with the compound is basically determined by the way the compound is to be administered. In certain embodiments, wherein the subject compound is to be injected, the preferred pharmaceutically-acceptable carrier is sterile, physiological saline, with a blood-compatible suspending agent, the pH of which has been adjusted to about 7.4.

In certain embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In certain embodiments, typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. AVICEL™, RC-591), tragacanth and sodium alginate; typical wetting agents include lecithin and polyethylene oxide sorbitan (e.g. polysorbate 80). In certain embodiments, typical preservatives include methyl paraben and sodium benzoate. In certain embodiments, peroral liquid compositions also contain one or more components such as sweeteners, flavoring agents and colorants disclosed above.

In certain embodiments, dry powder compositions may comprise propellants such as chlorofluorocarbons 12/11 and 12/114, or, in another embodiment, other fluorocarbons, non-toxic volatiles; solvents such as water, glycerol and ethanol, these include co-solvents as needed to solvate or suspend the active; stabilizers such as ascorbic acid, sodium metabisulfite; preservatives such as cetylpyridinium chloride and benzalkonium chloride; tonicity adjustors such as sodium chloride; buffers; and flavoring agents such as sodium saccharin.

In certain embodiments, the compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

In certain embodiments, also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In certain embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). In certain embodiments, such modifications may also increase the compound's solubility in aqueous solution, eliminate aggregation, enhance the physical and chemical stability of the compound, and greatly reduce the immunogenicity and reactivity of the compound. In certain embodiments, the desired in vivo biological activity may be achieved by the administration of such polymer-compound abducts less frequently or in lower doses than with the unmodified compound.

In certain embodiments, the compounds of the invention can be administered as the sole active pharmaceutical agent, they can also be used in combination with one or more other compound as described herein, and/or in combination with other agents used in the treatment and/or prevention of diseases, disorders and/or conditions, associated with a poxvirus infection, as will be understood by one skilled in the art. In another embodiment, the compounds as described herein can be administered sequentially with one or more such agents to provide sustained therapeutic and prophylactic effects. In another embodiment, the compounds may be administered via different routes, at different times, or a combination thereof. It is to be understood that any means of administering combined therapies which include the compounds of this invention are to be considered as part of this invention.

In another embodiment, the additional active agents are generally employed in therapeutic amounts as indicated in the PHYSICIANS' DESK REFERENCE (PDR) 53rd Edition (1999), which is incorporated herein by reference, or such therapeutically useful amounts as would be known to one of ordinary skill in the art. In another embodiment, the compounds of the invention and the other therapeutically active agents are administered at the recommended maximum clinical dosage or at lower doses. In certain embodiments, dosage levels of the active compounds in the compositions of the invention may be varied to obtain a desired therapeutic response depending on the route of administration, severity of the disease and the response of the patient. In another embodiment, the combination is administered as separate compositions or in other embodiments as a single dosage form containing both agents. In certain embodiments, when administered as a combination, the therapeutic agents is formulated, in another embodiment, as separate compositions that are given at the same time or different times, or in other embodiments the therapeutic agents can be given as a single composition.

In certain embodiments, the compositions and methods described herein are employed in the treatment of domesticated mammals which are maintained as human companions (e.g., dogs, cats, horses), which have significant commercial value (e.g., dairy cows. beef cattle, sporting animals), which have significant scientific value (e.g., captive or free specimens of endangered species), or which otherwise have value.

The following examples are presented in order to more fully illustrate the preferred embodiments of the invention. They should in no way be construed, however, as limiting the broad scope of the invention.

EXAMPLES

Example 1

Materials and Methods

Rapid Plate Assay

The rapid mechanistic plate assay, a high-throughput screening of a chemical library of chemical compounds, was used to identify inhibitors of processive DNA synthesis. The vaccinia virus (VV) E9 DNA polymerase protein and the processive VV proteins A20 and, D4R were used as targets for the inhibitors screened.

The following materials were used:
1. Cytoplasmic extract of vaccinia infected BS-C-1 cells.
2. 20-mer Oligonucleotide primer 5'-GCCAATGAATGAC-CGCTGAC-3' (SEQ ID No. 1).
3. 5' Biotinylated 100-mer oligonucleotide template: 5' biotin-GCACTTATTGCATTCGCTAGTCCACCT-TGGATCTCAGGCTATTCGTAGCGACCTA CGCG-TACGTTAGCTTCGGTCATCCCGTCAGCG-GTCATTCATTGGC-3' (SEQ ID No. 2).
4. Streptavidin-coated, transparent, nuclease-free plates (Roche).
5. DIG-dUTP (digoxigenin-11-2'-deoxy-uridine-5'-triphosphate), alkali-stable (Roche).
6. DIG Detection ELISA (ABTS, Roche) that contains anti-digoxigenin/peroxidase, Fab fragments conjugated with peroxidase (POD). POD reacts with the substrate ABTS (2,2'-azino-bis[3-ethylbenzthiazoline-6-sulfonic acid])
7. Phosphate-buffered saline (PBS), 10× stock solution. Per liter: 80 g NaCl, 2 g KCl, 11.5 g Na2HPO4.7H2O, and 2 g KH2PO4.
8. PBS working solution, pH 7.3: 137 mM NaCl, 2.7 mM KCl, 4.3 mM Na2HPO4, and 1.4 mM KH2PO4.
9. Wash buffer: PBS and 0.1% Tween-20.
10. Blocking stock solution (10×): Dissolve blocking reagent (Roche) in maleic acid buffer by constant stifling on a heating block (65° C.) or heat in a microwave, autoclave, and store at 4° C. The solution remains opaque.
11. PBS/1% blocking solution: Dilute the blocking stock solution (10×) 1:10 in PBS to 1%, and store at 4° C.
12. Maleic acid buffer: dissolve 10.6 g maleic acid (0.1 M) and 8.76 g NaCl (0.15 M) in 900 mL dH2O, and adjust pH to 7.5 with 10 N NaOH. Add ddH2O to 1 L.
13. Preparation of premix solution for DNA synthesis according to Table 1.
14. Addition of 1 µL each of in vitro-synthesized E9, A20, and D4.

TABLE 1

Preparation of Premix Solution for DNA Synthesis[a]

| Component | Final conc. | Stock solution | Amount of stock solution (µL) per well |
|---|---|---|---|
| (NH4)2SO4 | 100 mM | 1M | 5.0 |
| Tris-HCl, pH 7.5 | 20 mM | 200 mM | 5.0 |
| MgCl2 | 3 mM | 100 mM | 1.5 |
| EDTA | 0.1 mM | 5 mM | 1.0 |
| DTT | 0.5 mM | 10 mM | 2.5 |
| Glycerol | 4% | 50% | 4.0 |
| BSA | 40 µg/mL | 10 mg/mL | 0.2 |
| dATP | 50 µM | 5 mM | 0.5 |
| dGTP | 50 µM | 5 mM | 0.5 |
| dCTP | 50 µM | 5 mM | 0.5 |
| DIG-dUTP | 10 µM | 1 mM | 0.5 |

BSA = bovine serum albumin;
DIG = digoxigenin;
DTT = dithiothreitol.

The Rapid Plate Assay Overview:

A template with biotin attached to its 5'-end and a primer annealed to its 3'-end was bound to the streptavidin-coated wells of 96-well plates. The premix solution, containing vaccinia cytoplasmic extract and dNTPs with DIG-dUTP (substituted for dTTP), was then added to the wells of the plates. This was followed by the addition of the chemical test compounds. The plates were incubated to enable the DNA synthesis reaction to proceed. Then the reaction was stopped, and the incorporation of dNTPs into synthesized DNA was detected by an ELISA reaction that employs anti-DIG antibody conjugated to peroxidase.

Annealing Primer to Template:

250 pmol (1.525 µg) of primer and 250 pmol (8.25 µg) of biotinylated template were mixed in 0.25 mL PBS (pH 7.3), and annealed by heating to 90° C. for 5 minutes, followed by cooling to room temperature. Then the annealed primer/template (P/T) was diluted to 0.1 µM with cold PBS, and stored at −20° C.

Binding Primed Template to 96-Well Plates:

0.2 pmol of P/T (1.22 ng of primer and 6.6 ng of template) in 100 µL were added to each well of the streptavidin-coated plates, followed by incubation of the foil-covered wells for 90 min at 37° C. or overnight at 4° C.

DNA Synthesis Reaction:

The P/T binding solution was removed from the 96-well plates and 25.2 µL of the premix solution was added to each well, followed by the addition of the chemical test compound or H2O (24.8 µL) to a final reaction volume of 50 µL 2. 3. Then the reaction mixture was incubated at 37° C. for 90 min. For a negative control, a separate premix solution was used in which E9, A20, and D4R were absent. The reaction was stopped by adding 1 µL of 0.5 M EDTA.

First Plate Wash:

The reaction mixture was removed, and wells were washed six times with 200, 225, 250, 275, 300, and 325 µL of wash buffer.

Binding of Anti-DIG-POD:

100 µL anti-DIG-POD working solution (final concentration of 200 mU/mL in PBS/1% blocking reagent) was added followed by incubation at 37° C. for 1 h.

Second Plate Wash:

The anti-DIG-POD working solution was removed followed by washing six times with 200, 225, 250, 275, 300, and 325 µL of wash buffer.

POD Color Detection as a Measure of DNA Synthesis:

The ABTS substrate for POD was added to the wells. Color development generally occurred within 5-30 min to produce an OD 405 nm of 0.4-1.0.

Quantification of DNA Synthesis by ELISA:

ELISA reader at 405 nm was used to quantify absorbance proportional to the incorporated DIG-dUTP.

Compound Library

The NCI Training and Diversity Set libraries were obtained from the Drug Synthesis and Chemistry Branch, Developmental Therapeutics Program, National Cancer Institute. The Training Set contains 230 anti-cancer compounds that are frequently used to confirm the reproducibility of high throughput screening assays. The Diversity Set comprises 1,992 compounds selected from approximately 140,000 compounds using the Chem-X program (Accelrys, San Diego, Calif., USA). These compounds represent diversity in terms of three-dimensional pharmacophores.

In Vitro Translated Proteins and Vaccinia Virus-Infected Cell Lysate

Vaccinia virus polymerase (E9), putative processivity factor (A20) and UDG (D4) proteins were expressed from pcDNA3.2/v5 (Invitrogen) in vitro using Promega TNT coupled transcription/translation system. KSHV DNA polymerase-8 (Pol8) and processivity factor-8 (PF8) were translated in vitro from pTM1-Pol8 and pTM1-PF8 respectively. To confirm expression, an aliquot of the translation reactions were labeled with [$^{35}$S]-methionine, fractionated on an SDS-10% polyacrylamide gel, and visualized by autoradiography. The vaccinia virus-infected cell lysate was prepared according to previously described methods. The WR strain of vaccinia virus, a thymidine kinase deficient mutant, was used to infect monolayers of BSC-1 cells at a multiplicity of infection of 15. The vaccinia-infected cells were incubated at 37° C. for 6 h in the presence of hydroxyurea. The cells were harvested by scraping then pelleted at 500 rpm. The pellet was washed with phosphate-buffered saline (PBS) followed by hypotonic buffer (10 mM Hepes, 1.5 nM $MgCl_2$, 10 mM KCl). After resuspension in hypotonic buffer, the cells were Dounce homogenized and centrifuged at 15,000 rpm for 30 min. The suspension was passed through a 2 micron filter to remove the viral cores and nuclear particles. The vaccinia-infected lysate was stored in −80° C. in the presence of 20% glycerol.

High-Throughput Screening for Inhibitors of DNA Synthesis Using the Rapid Plate Assay A rapid plate DNA synthesis assay was performed using vaccinia-infected cell lysate. A 1.2:1 ratio of a 20-mer oligonucleotide primer (5'-GCGAATGAATGACCGCTGAC-3', SEQ ID No. 1) and a 5'-end biotinylated 100-mer oligonucleotide template (5'-Biotin-GCACTTATTGCATTCGCTAGTCCACCTT GGATCTCAGGCTATTCGTAGC-GAGCTACGCGTACGTTAGCTTCGGTCATCCCGTCAGC GGTCATTCATTGGC-3', SEQ ID No. 2) were heated at 90° C. for 5 min and annealed by gradual cooling to room temperature. The annealed primer-template (P/T) was diluted with PBS to a concentration of 10 pmol/µL. The 96-well microtiter streptavidin-coated plates (Streptawell plates, Roche Applied Science, Indianapolis, Ind., USA) were coated with 5 pmol/well of the P/T solution and incubated at 37° C. for 90 min. The wells were washed with 100 µL PBS. Control (DMSO, acyclovir prodrug, azidothymidine (AZT) prodrug and ethylenediamine tetracetic acid (EDTA)) and test compounds were individually added to the wells to a final concentration of 167 µM. The vaccinia virus used in this primary screen is a thymidine kinase deficient mutant, and therefore resistant to AZT and acyclovir, prodrugs which require phosphorylation. The 60 µL DNA synthesis reaction mixture contained 100 mM $(NH_4)_2SO_4$, 20 mM Tris-HCl pH 7.4, 3 mM $MgCl_2$, 0.1 mM EDTA, 0.5 mM DTT, 2% glycerol, 40 ug/mL BSA, 5 uM dNTPs, 1 uM digoxigenin-11-2'-deoxyuridine-5'-triphosphate (DIG-dUTP, Roche Applied Science) and 1 µL vaccinia lysate. The plates were incubated at 37° C. for 30 min. Total DNA synthesis activities were determined by measuring incorporation of DIG-dUTP. The activity was quantified by a DIG detection ELISA kit (Roche Applied Science) using anti-digoxigenin-peroxidase (anti-DIG-POD) and its substrate 2,2'-azino-bis(3-ethylbenzthiazoline)-sulfonate (ABTS), and by measuring the absorbance at 405 nm on a microplate reader (Tecan Genius Pro, Tecan US).

Selectivity Screen

The selectivity screen was used to eliminate general and irrelevant inhibitors of vaccinia DNA synthesis. The microplate assay was optimized for KSHV Pol8/PF8 DNA synthesis. P/T solution of 0.2 pmols was added to each well. Each reaction well received control or test compounds and 2 µL each of in vitro translated Pol8 and PF8. The reaction time was extended to 1 h at 37° C. The buffer, BSA and dNTP conditions used were the same as described for vaccinia, vide supra.

Polymerase vs. Processivity Inhibition

Two separate plate assays were used to distinguish polymerase versus processivity inhibitors. For the polymerase inhibition assay, a biotinylated primer/template (5'-GCGAATGAATGACCGCTGAC-3', SEQ ID No. 1)/(5'-Biotin-GCACTTATTGCATTCGCTAGTCCACCT-TGGATCTCAGGCTATTCGTA GCGAGCTACGCGTACGTTAGCTTCGGT-CATCCCGTCAGCGGTCATTCATTGGC-3' SEQ ID No. 2) was designed so that the DIG epitope would be uniformly incorporated throughout the template. The DNA synthesis reaction was performed using a low salt buffer (20 mM Tris-HCl pH 7.4, 3 mM $MgCl_2$, 0.1 mM EDTA, 0.5 mM DTT, and 2% glycerol) and 1 µL polymerase enzyme E9. For the processivity inhibition assay, a second biotinylated primer/template (5'-GCCAATGAATGACCGCTGAC-3')/(5'-Biotin-AGCACTATTGACATTACAGAGTCGCCTTGGCTCTCT-GGCTGTTCGTTGCGGGCTCCGCG TGCGTTGGCT-TCGGTCGTCCCGTCAGCGGTCATTCATTGGC-3') was designed so that the DIG epitope would be incorporated at the distal end of the template. The plate assay was conducted using a high salt buffer (100 mM $(NH_4)_2SO_4$, 20 mM Tris-HCl pH 7.4, 3 mM $MgCl_2$, 0.1 mM EDTA, 0.5 mM DTT, 2% glycerol). One microliter each of the in vitro translated proteins A20, D4, and E9 were added to each well.

M13 DNA Synthesis

In vitro DNA synthesis using an M13-primed template was performed. Briefly, the DNA synthesis reactions were performed in 25 µL volumes containing 10 mM Tris-HCl (pH 7.5), 40 mg/mL of bovine serum albumin, 4% glycerol, 0.1 mM EDTA, 5 mM dithiothreitol (DTT), 8 mM $MgCl_2$, 20 fmol of singly primed M13mp18 single-stranded (ss) DNA, 750 ng of E. coli SSB, 60 µM (each) dGTP, dTTP and dATP, and 20 µM [$\alpha$-$^{32}$P]dCTP. The mixtures were pre-incubated with the proteins and dATP, dGTP and dTTP at 30° C. for 3 min. The reactions were initiated by the addition of radiolabeled dCTP, incubated for another 30 min and stopped by the addition of an equi-volume of 1% SDS-40 mM EDTA. The reaction products were fractionated at 60V on a 0.8% denaturing agarose gel and analyzed by a PhosphorImager (Amersham Biosciences).

Plaque Reduction Assay

The cell lines used were African green monkey kidney BSC-1 cells grown in Dulbecco's modified Eagle medium (DMEM) supplemented with 10% fetal bovine serum (FBS) (Gibco BRL Life Technologies, Gaithersburg, Md.) and 0.1% gentamicin antibiotic. The cell cultures were maintained at 37° C. in a humidified 5% $CO_2$ environment. Confluent BSC-1 cells were infected with 100 µL/well of 100-150 pfu of vaccinia virus in a 48-well plate. After 1 h incubation, 400 µL/well of DNA synthesis inhibitor (100 µM) or control solutions were added and incubated at 37° C. overnight. All inhibitors and controls were dissolved in DMSO and diluted with the medium. A 5% solution of formaldehyde in PBS was used to fix the cells. After washing twice with PBS, the plate was stained with 0.2% crystal violet in 50% ethanol.

Cytotoxicity Assay

BSC-1 cells were grown to confluency in white 96-well cell culture plates at 37° C. in DMEM containing 10% FBS and 0.1% gentamicin in the presence or absence of inhibitor. Cytotoxicity was assayed using the a Cella-Tox bioluminescence cytotoxicity kit (Cell Technology Inc., Mountainview, Calif.) according to manufacturer's protocol. All inhibitors and controls were assayed at a final concentration of 100 µM. A lysing agent was used to calculate the maximum release of glyceraldehyde-3-phosphate dehydrogenase as a positive control.

Compound Confirmation

The molecular weight of the hit compounds were confirmed using low resolution liquid chromatography/mass spectrometry, electrospray ionization mode (ES+, Micromass LC, Opus software system, Department of Chemistry, University of Pennsylvania).

Primary High-Throughput Screen

The primary high-throughput screen was performed in 384-well plates coated with streptavidin SigmaScreen plates, Sigma-Aldrich cat #S8686). DNA synthesis reactions were run with 0.5 µL vaccinia virus extract in 20 mM Tris-Cl pH7.5, 100 mM ammonium sulfate, 5 mM $MgCl_2$, 0.1 mM EDTA, 0.5 mM DTT, 4% glycerol, 40 µg/mL BSA, 5 µM of each dATP, dCTP, and dGTP, 4 µM dTTP, 0.5 µM DIG-11-dUTP, in a total volume of 30 µL. Two pmoles of biotinylated primer/template dissolved in 30 µL PBS were immobilized on streptavidin coated wells. Unbound primer/template was removed, wells were washed twice with 50 µL PBS and loaded with 20 µL reaction buffer (20 mM Tris-Cl pH7.5). One hundred nL of compound or natural extract dissolved in DMSO were transferred from the library plates with 384-pin arrays. Reactions were started by loading 10 µL of a 3× reaction mixture. After quick centrifugation, plates were incubated at 37 C for 30 minutes. The DNA synthesis reactions were stopped with 30 µL of a solution containing 50 mM EDTA and 2% SDS in 10 mM Tris pH8. Incorporation of DIG-11-dUTP in the newly synthesized DNA strand was measured with peroxidase-conjugated anti-digoxigenin antibody (anti-DIGPOD). Wells were flow-washed with 400 µL PBS, 0.1% Tween-20 at the lowest dispensing speed and loaded with 4.5 mU of anti-DIG-POD in 30 µL PBS/blocking solution. After gently rocking at room temperature for 1 h, the antibody solution was removed and wells were flow-washed as above. Thirty µL of 2,2'-azino-bis(3-ethylbenzthiazoline)-sulfonate (ABTS) peroxidase substrate dissolved in citrate buffer was added and plates were gently rocked at room temperature for 1 h. Color development was stopped with 10 uL of 4% SDS and absorbance at 405 nm was measured. Readings from each well were divided by the plate median and percent inhibition was determined relative to the values of uninhibited reaction control.

Screened Libraries

The optimized assay was first trained and confirmed by screening 1,520 known bioactive chemical compounds compiled in two collections: BIOMOL ICCB Known Bioactives 1 (480 compounds) and NINDS Custom Collection (1,040 compounds). A total of 45,832 chemical compounds from the following libraries: ChemDiv 3 (16,544 compounds), MixCommercial 5 (268 compounds), Maybridge 4 (4,576 compounds), ActiMol TimTec 1 (8,518 compounds), Bionet 2 (1,700 compounds), Enamine 1 (6,004 compounds), I.F. Lab 1 (6,543 compounds), I.F. Lab 2 (292 compounds), Maybridge 2 (704 compounds), MixCommercial 4 (331 compounds), and Peakdale 2 (352 compounds) were tested in duplicate, at a single concentration of 16.7 µg/mL, which is equivalent to a molar concentration of 33 µM or higher. Natural extracts with inhibitory activity were also identified by screening the Stan Foundation Extracts 2 library (1,000 extracts from plants used in traditional Chinese medicine), and two collections of partially purified extracts from endophytic fungi: ICBG Fungal Extracts 1 (851 extracts) and ICBG Fungal Extracts 2 (460 extracts).

DNA Synthesis Assay

Selected compounds were purchased and suspended in DMSO at a final concentration of 20 mM. The compounds were tested over a range of concentrations for their ability to inhibit vaccinia virus-catalyzed DNA synthesis. Assays were run in 96-well plates in conditions similar to those used in the high-throughput screen. Each compound was tested in triplicate in two-fold serial increments and IC50 values were calculated using the Prism software for linear regression.

Antiviral Activity Assays in Cultured Cells (Plaque Reduction Assay and Cell Protection Assay)

For the plaque reduction assay, BSC-1 cells were seeded at 6×104 cells/well in 48-well plates. Next day, cells were infected with 50 plaque forming units (pfu)/well of vaccinia virus WR in DMEM with 10% FBS and 50 mg/L gentamicin sulfate. Tested compounds were diluted in growth medium and added over the virus/cell cultures. Plates were incubated overnight at 37° C. with 5% CO2. Cells were fixed with a solution of 5% formaldehyde in PBS and stained with 0.2% crystal violet dissolved in 50% ethanol. Wells were washed, let dry and plaques were counted under a microscope. The final concentration of compound-derived DMSO was 1% (v/v) in all cellbased assays. For the control samples that contained no compound, an appropriate volume of DMSO was added at a final concentration of 1%.

Cytotoxicity Assay

Reagents and Materials

Proteins

Processive DNA synthesis was catalyzed by early-expressed vaccinia proteins from cytoplasmic extracts of BS-C-1 cells infected with the vaccinia virus strain WR. harvested 6 hours after infection. The cytoplasmic extracts were filtered twice through 0.2 mm and contained no infectious particle as shown by plaque assay.

Annealed Primer/Biotinylated Template: synthesized by Integrated DNA Technologies Pimer 20 nucleotides ((5'-GCGAATGAATGACCGCTGAC-3', SEQ ID No. 1) Template 100 nucleotides 5' end biotinylated (5' Biotin-GCACTTAT-TGCATTCGCTAG TCCACCTTGG ATCTCAGGCT ATTCGTAGCG AGCTACGCGT ACGTTAGCTT CGGT-CATCCC GTCAGCGGTC ATTCATTGGC-3').

Annealing: 15 nmoles (92 mg) of primer and 15 nmoles (470 mg) of template are mixed in 1.5 mL PBS (pH 7.3), and annealed by heating to 90 C for 5 minutes, then cooled to room temperature. The final P/T concentration is 10 mM or 10 pmole/mL.

SigmaScreen Streptavidin coated plates; 384-well, clear (Sigma cat#S8686-100EA); Digoxigenin-11-2'-deoxy-uridine-5'-triphosphate (DIG-11-dUTP), alkali-stable, 1 mM (Roche cat#11 570 013 910); Deoxynucleotide Triphosphate Set, PCR Grade, Na-Salt, 100 mM (Roche cat#11969064001); Anti-Digoxigenin-POD, Fab fragments from sheep (Roche cat#11 207 733 910); 2,2'-Azino-bis-(3-ethylbenzthiazoline-6-sulfonic acid)diammonium salt (ABTS), (Roche cat#10 102 946 001) dissolved in ABTS buffer (Roche cat#11 112 597 001) at 1 mg/mL; Blocking reagent (Roche, Cat #11 096 176001) 10% (w/v) in maleic acid buffer (0.1 M maleic acid, 0.15 M NaCl, pH to 7.5) diluted 1:10 in PBS to 1% (w/v) final. Stop: 2% SDS, 50 mM EDTA, 10 mM Tris pH8 Wash: PBS+0.1% Tween-20

Analog Compounds

Analogs of tetracycline were obtained through compound mining by performing structural similarity searches using the Bit Vector Structural Map online http://spheroid.ncifcrf.gov/spheroid/ developed by the Developmental Therapeutic Program of the National Cancer Institute to aid in drug discovery. The 52 tetracycline structurally related compounds were obtained from the Drug Synthesis and Chemistry Branch, Developmental Therapeutics Program, National Cancer Institute (http://dtp.nci.nih.gov/).

Vaccinia Virus-Infected Cytoplasmic Lysate and In Vitro Translated Proteins

Throughout the study, thymidine kinase (TK) deficient strain of vaccinia virus, provided by Drs. G. Cohen and R. Eisenberg, was used to infect BSC-1 cells (34). Vaccinia virus-infected cell lysate was prepared as previously described (16). Briefly, the cells were infected at a multiplicity of infection of 15. The vaccinia-infected cells were incubated at 37° C. for 6 h in the presence of hydroxyurea, then harvested by scraping and pelleted at 500 rpm. The pellet was washed with phosphate-buffered saline (PBS) followed by hypotonic buffer (10 mM Hepes, 1.5 mM $MgCl_2$, 10 mM KCl). The cells were then Dounce homogenized and centrifuged at 15,000 rpm for 30 min. The cell suspension was passed through a 2 micron filter to remove the viral cores and nuclear particles. At this point, the vaccinia-infected cytoplasmic lysate was stored in −80° C. in the presence of 20% glycerol. Vaccinia E9, A20 and D4 proteins were translated in vitro as previously described (34). The proteins were expressed from pcDNA3.2/v5 (Invitrogen) in vitro using Promega TNT coupled transcription/translation system. The translation reactions were labeled with [$_{35}$S]-methionine, fractionated on 10% SDS-PAGE, and visualized by autoradiography.

DNA Synthesis Inhibition Assay

A rapid plate DNA synthesis assay (19) was performed using optimized conditions. Briefly, a 1.2:1 ratio of a 20-mer oligonucleotide primer (5'-GCGAATGAATGACCGCT-GAC-3', SEQ ID No. 1) and a 5'-end biotinylated 100-mer oligonucleotide template (5'-Biotin-AGCACTATTGACAT-TACAGAGTCGCCTTGGCTCTCTGGCTGT-TCGTTGCGGGCTCCGCG TGCGTTGGCTTCG-GTCGTCCCGTCAGCGGTCATTCATTGGC-3') were annealed and loaded into a 96-well microtiter streptavidin-coated plate (Streptawell plates, Roche Applied Science, Indianapolis, Ind., USA) at 5 pmol/well. The wells were incubated at 37 C for 90 min, and washed with 100 L PBS. The reaction was conducted in low salt buffer (20 mM Tris-HCl pH 7.4, 3 mM $MgCl_2$, 0.1 mM EDTA, 0.5 mM DTT, 2% glycerol, 40 ug/mL BSA, 5 uM dNTPs, 1 uM digoxigenin-11-2'-deoxyuridine-5'-triphosphate (DIG-dUTP, Roche Applied Science) with 1 μL vaccinia infected cell lysate or 1 uL of in vitro translated E9 DNA polymerase. The reaction plates were incubated at 37° C. for 30 min. Total DNA synthesis activities were determined through incorporation of DIG-dUTP using a DIG detection ELISA kit (Roche Applied Science) and its substrate 2,2'-azino-bis(3-ethylbenzthiazoline)-sulfonate (ABTS). The plates were read at an absorbance of 405 nm on a microplate reader (Tecan Genius Pro, Tecan US).

Plaque Reduction Assay

African green monkey kidney BSC-1 cells were grown in Dulbecco's modified Eagle medium (DMEM) supplemented with 10% fetal bovine serum (FBS) (Gibco BRL Life Technologies, Gaithersburg, Md.) and 0.1% gentamicin antibiotic at 37° C. in a humidified 5% $CO_2$ environment. Confluent BSC-1 cells were infected with vaccinia virus at an MOI of 0.005 in 48-well plate. One hour post infection, 400 μL of the test compounds and control were added per well at concentrations ranging from 200 nM to 200 μM and incubated at 37° C. for 16 hours. Viridicatumtoxin, tetracycline, and control cidofovir were dissolved in DMSO and diluted with the medium. A 5% solution of formaldehyde in PBS was used to fix the cells. After washing twice with PBS, the plate was stained with 0.2% crystal violet in 50% ethanol.

Cytotoxicity Assay

A cytotoxicity assay that measures the release of glyceraldehydes-3-phosphate dehydrogenase (GAPDH) was conducted using the aCella-TOX bioluminescence cytotoxicity kit (Cell Technology Inc., Mountainview, Calif.), following the manufacturer's protocol. Briefly, BSC-1 cells were grown to confluency in white 96-well cell culture plates at 37° C. in DMEM containing 10% FBS and 0.1% gentamicin in the presence or absence of inhibitor (200 nM to 200 μM). A lysing agent that produces maximum release of GAPDH served as a positive control.

Determination of Therapeutic Index

In determining the cellular therapeutic index, no tests were conducted at concentrations greater than 200 μM due to the limited availability of the compounds and solubility issues at higher stock concentrations. The concentration of inhibitor that causes half of the maximum cell cytotoxicity (CC50) and the concentration that reduces 50% of the plaques ($IC_{50}$) were used to determine the therapeutics index as follows:

$$\left\{ \text{Therapeutic Index } (TI) = \frac{\text{Cell Cytotoxicity } (CC_{50})}{\text{Inhibitory Concentration } (IC_{50})} \right\}$$

Cell Viability Assays

The cell viability at the plaque $IC_{50}$ value was performed using two independent methods, cell counting and MTT assay. For the cell counting method, cells were incubated overnight at 37° C. to sub-confluency in 48-well plates. The compounds dissolved in DMSO, were further diluted in media to a final concentration required to achieve the plaque $IC_{50}$ value. The cells were incubated with the compounds for 24 hrs. The media was removed, the cells trypsinized and stained with tryphan blue, and counted. The MTT assay was also used to confirm cell viability at the plaque $IC_{50}$. Cells were seeded at $1.5 \times 10^4$ cells/well in a 96-well plate and incubated overnight at 37° C. at 5% $CO_2$. Compounds dissolved in DMSO were mixed with media to obtain the concentration required to achieve the plaque $IC_{50}$ value, and incubated with the cells for 16 h. Each well received 20 µL of the MTT solution (5 mg MTT/mL PBS) and the plate was rocked for 5 min. The plates were incubated for an additional 5 h to metabolize MTT, after which the media was removed, and the plates were air dried. To resuspend the formazan, the end product of the MTT assay, 200 µL of DMSO was added to each well and the plates were rocked for 5-10 min. Absorbance was read at 560 nm.

Quantitative RT-PCR of Vaccinia Genes

BSC-1 cells in 48-well plates were infected with vaccinia virus at an MOI of 30. The test compounds were added to a final concentration of 20 µM and incubated at 37° C. Infection time points were obtained by removing the media, lysing and scraping the cells into pre-cooled tubes. Total RNA from the samples were isolated using RNeasy mini RNA kit from Qiagen and quantified by measuring the absorbance on Nanodrop (Nanodrop Technologies, Wilmington Del.). Equal aliquot volumes of each sample were reverse transcribed according to Superscript first strand DNA synthesis system (Invitrogen) protocol. Quantitative RT-PCR was performed using LightCycler DNA Master Sybr Green from Roche, and primers designed to probe for early E3, late F9 viral genes and host GAPDH mRNA expression. The levels of expressed viral genes were normalized according to the level of GAPDH. The primer pairs used were: F9L Fwd GGACAGTTTAAAAATTGCGCGCTCCG-F9L (SEQ ID No. 3) Rev CGTCTAGATCTATTC CTATTT CTTCAG CGATAGC (SEQ ID No. 4) B5R Fwd CTTCGGATCCAAATGCTGTCTGCG (SEQ ID No. 5) B5R Rev CGCCGTTGCAACTTAGTGT CATGGTG (SEQ ID No. 6) E3L Fwd GGAATCGAA GGAGCTACTGCTGCAC E3L (SEQ ID No. 7) Rev CTTATCCGCCTCCGTTG TCATAAACC (SEQ ID No. 8) gapdh Fwd CCATGGTGAAGGTGAAGACTGC (SEQ ID No. 9) GAPDH Rev CAGCCTTGAC AGTGC CATGG (SEQ ID No. 10). The thermal cycler conditions were 10 min at 95° C., 45 cycles of 5 s at 95° C. followed by 5 s at 60° C. and 5 s at 72° C. All of the samples were assayed in duplicate. A DNA standard calibration curve was plotted using known concentrations of standard cDNA and primers.

Western Blot Analysis

Cells were harvested and lysed at 4° C. Cells were pelleted (300×g/2 min) and 4×LDS was added to the supernatant that was heated to 95° C. and loaded onto a 10% Bis-Tris gels (Invitrogen). Proteins on the gel were transferred onto a nitrocellulose membrane and probed with primary E3, L1 and GAPDH antibodies, secondary anti-mouse or anti-rabbit peroxidase conjugated antibodies, and visualized by chemiluminescence (Pierce). The vaccinia antibodies were kindly provided by Drs. G. Cohen and R. Eisenberg.

Example 2

Screening of Chemical Libraries for Compounds that Block Vaccinia Virus DNA Synthesis Using the invented mechanistic Rapid Plate Assay (See also U.S. Pat. No. 6,204,028), a chemical library was screened for compounds that block vaccinia virus DNA synthesis. Then compounds that blocked vaccinia virus DNA synthesis in the Rapid Plate Assay were further tested for preventing vaccinia virus from infecting tissue culture cells (plaque reduction) with minimal toxicity.

The following compounds (the details of which are set forth in Table 2) were effective in blocking the replication of vaccinia virus in cells and thus can be as therapeutic compounds for blocking smallpox virus replication. Additional particularly effective compounds were found (structures XLIV and XLV).

I. (E)-N-1-(6-chloro-2-phenyl-4H-chromen-4-ylidene)-N2, N2-dimethylethane-1,2-diamine.

II. (E)-2-(6-methyl-2-phenyl-4H-chromen-4-ylideneamino) ethanol

III. (E)-N-(6-methyl-2-phenyl-4H-chromen-4-ylidene)propan-1-amine

IV. Flufenamic Acid

V. Apigenin

VI. Ro 31-8220; Bisindolylmaleimide IX; or Carbamimidothioic acid, 3-[3-[2,5-dihydro-4-(1-methyl-1H-indol-3-yl)-2,5-dioxo-1H-pyrrol-3-yl]-1H-indol-1-yl]propyl ester (9CI)

VII. (2-(2,4-dimethoxyphenyl)indolizin-3-yl)(pyridin-3-yl) methanone

VIII. (E)-methyl 9-(hydroxyimino)-9H-fluorene-4-carboxylate

IX. 6H-Indolo[2,3-b]quinoxaline-6-acetic acid, 9-chloro- (9CI)

X. 6H-Indolo[2,3-b]quinoxaline-6-(2-morpholinoethy)

XI. 1H-Imidazole, 2-[[(2,4-dichlorophenyl)methyl]thio]-1-(ethylsulfonyl)-4,5-dihydro-(9CI)

XII. 2-(2,6-dichlorobenzylthio)-6-methylpyrimidin-4-yl furan-2-carboxylate

XIII. (Z)-5-imino-6-((4-oxo-4H-chromen-3-yl)methylene)-5H-[1,3,4]thiadiazolo[3,2-a]pyrimidin-7(6H)-one XIV. 3-(4-chlorophenylthio)-6-methyl-1H-indole-2-carboxylic acid XV. Benzoic acid, 3-[[(3,5-dibromo-2-hydroxyphenyl)methylene]amino]-2-methyl-(9CI)

XVI. (E)-2,4-dichloro-6-((5-methylisoxazol-3-ylimino)methyl)phenol

XVII. 4H-Thiazolo[5,4-b]indole, 4-acetyl-2-methyl-(9CI)

XVIII. Imidazo[2,1-b]benzothiazole-7-carboxamide, N-(1-ethyl-2-pyrrolidyl)methyl-2-(3-methoxyphenyl)-(9CI)

XIX. N-tert-butyl-4-(7-methylthieno[3,2-d]pyrimidin-4-yl) piperazine-1-carboxamide XX. CA Registry Number: 874880-06-5

XXI. "N-Fmoc-anthranilic acid; Benzoic acid, 2-[[(9H-fluoren-9-ylmethoxy)carbonyl]amino]-(9CI)"

XXII. 4-Quinazolinamine, N-(2,4-dimethoxyphenyl)-2-(4-methyl-1-piperazinyl)-(9CI)

XXIII. Benzoic acid, 2-[1-[[amino[(7-methoxy-4-methyl-2-quinazolinyl)imino]methyl]imino]ethyl]-(9CI)

XXIV. (E)-N-((9-ethyl-9H-carbazol-2-yl)methylene)-4H-1, 2,4-triazol-4-amine

XXV. CA Registry Number: 902915-02-0

XXVI. 1,4-Pentadien-3-one, 1,5-di-2-furanyl-(9CI)

XXVII. Methyl 6-isopropyl-2-(4-methoxyphenylamido)-4, 5,6,7-tetrahydrothieno[2,3-c]pyridine-3-carboxylate hydrochloride XXVIII. (E)-4-(3-(ethoxycarbonyl)-5-methyl-4-phenylthiophen-2-ylamino)-4-oxobut-2-enoic acid XXIX. Tipindol; Tipindole; Typindole; Thiopyrano[4,3-b] indole-8-carboxylic acid, 1,3,4,5-tetrahydro-, 2-(dimethylamino)ethyl ester (7CI,8CI,9CI)

XXX. 2,6-bis(4-(dimethylamino)phenyl)pyrylium

XXXI. (E)-1-ethyl-5-((E)-3-(furan-2-yl)allylidene)-2-thioxodihydropyrimidine-4,6(1H,5H)-dione XXXII. (E)-5-(furan-2-ylmethylene)-2-imino-3-(thiazol-2-yl)thiazolidin-4-one XXIII. 1H-Pyrrole-3-carboxylic acid, 1-(4-carboxyphenyl)-2-methyl-5-phenyl-, 3-ethyl ester (9CI)

XXXIV. 2-(2-chloro-5-(trifluoromethyl)phenylamino)-5-methoxybenzoic acid

XXXV. 3-(2-bromobenzyloxy)-6-methyl-1-(thiophen-2-yl)-5,6,7,8-tetrahydro-2,6-naphthyridine-4-carbonitrile XXXVI. 2-amino-3-(9-(4-chlorophenyl)-9H-fluoren-9-ylthio)propanoic acid XXXVII. Fentichlor; 2,2'-thiobis(4-chlorophenol)

XXXVIII. Tetracycline; 4-(dimethylamino)-3,6,10,12,12a-pentahydroxy-6-methyl-1,11-dioxo-1,4,4a,5,5a,6,11,12a-octahydrotetracene-2-carboxamide methanesulfonate.

XXXIX. (E)-3-(4-chloro-3-nitrobenzylideneamino)-2-thioxothiazolidin-4-one.

XL. 6,6'-(ethane-1,2-diylbis(oxy))bis(2-methylquinolin-4-amine).

XLI. 2,2'-sulfonylbis(4-chlorophenol).

XLII. 4,4'-(2,2'-azanediylbis(ethane-2,1-diyl)bis(tellanediyl))diphenol.

Example 3

Identification of Polymerase and Processivity Inhibitors of Vaccinia DNA Synthesis Using a Stepwise Screening Approach Step I. Primary High-Throughput Screen For this study, the rapid plate assay was performed in a microtiter plate in which a 100-nucleotide template with biotin covalently linked to its 5' end was immobilized onto the streptavidin-coated wells. A 20-nucleotide primer was annealed to the 3' end of template. Vaccinia lysate was added to each well of the plate to allow incorporation of the four dNTPs as well as digoxigenin-dUTP. A peroxidase-conjugated anti-digoxigenin antibody that recognizes digoxigenin in the newly synthesized DNA generated a colorimetric reaction that was quantified with a plate reader at 405 nm.

The rapid plate assay was used to screen the NCI Diversity and Training Set library of 2,222 compounds. This library contains diverse three-dimensional structures representative of approximately 140,000 compounds from the NCI-DTP library. For this primary screen, all compounds were tested at a concentration 167 µM. The results of a typical plate are represented in FIG. 2. Compounds that inhibit DNA synthesis (hit compounds) were identified by a decrease in absorbance at 405 nm. A total of 169 compounds decreased DNA synthesis by 50% or greater, giving a hit rate of 7.6%.

Step II. Selectivity Screen 169 hit compounds obtained from the primary screen (Step I) were tested to determine if these vacccinia inhibitors were also able to block DNA synthesis conducted by a completely different polymerase and processivity complex. For this purpose, the unrelated KSHV DNA polymerase (Pol8) and processivity factor (PF8) were used. Compounds that block DNA synthesis of vaccinia virus but not KSHV are of greatest interest since irrelevant reasons for the inhibition (e.g. DNA intercalation and DNA groove binding) are eliminated. Moreover, these vaccinia virus selective inhibitors unlikely bind to conserved structural motifs of the KSHV and vaccinia proteins. Compounds in step II that inhibited KSHV DNA synthesis by 50% or greater were considered nonspecific. The results of this step yielded 47 compounds, giving a hit rate of 2.1% from Step I (2,222 compounds). Results of one of the selectivity plates are presented in FIG. 3. The compounds that inhibited both KSHV and vaccinia were set aside for future cytotoxicity testing since they have a general preference for viral proteins as opposed to cellular proteins.

Step III. Screen to Distinguish Polymerase vs. Processivity Inhibitors

A20, D4 and E9 proteins are necessary and sufficient for vaccinia processive DNA synthesis. Thus the assays were designed to distinguish between vaccinia inhibitors that target nucleotide incorporation by E9 alone from inhibitors that target processive incorporation of dozens to thousands of nucleotides by the triad, A20, D4 and E9.

Figure 4A:
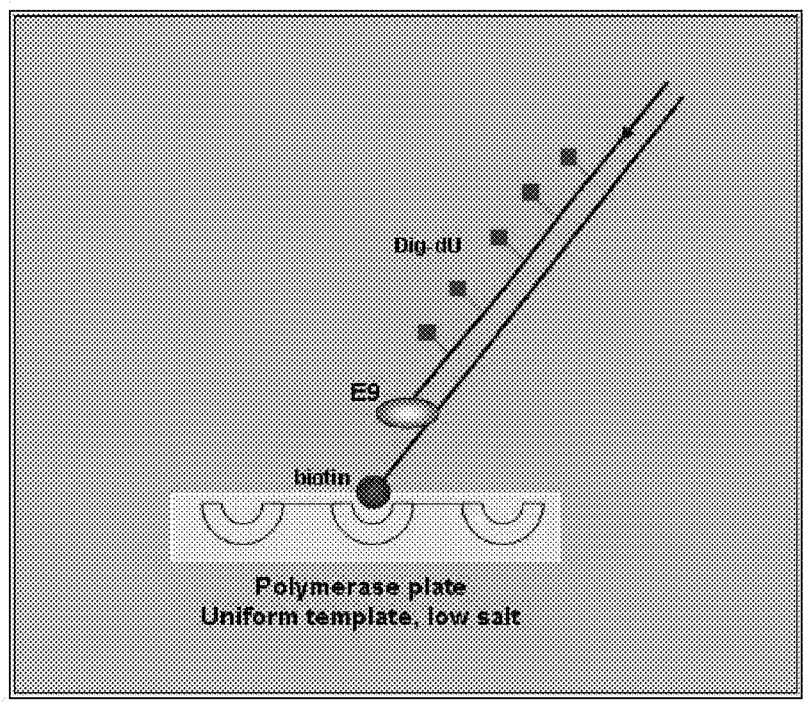
Figure 4B:
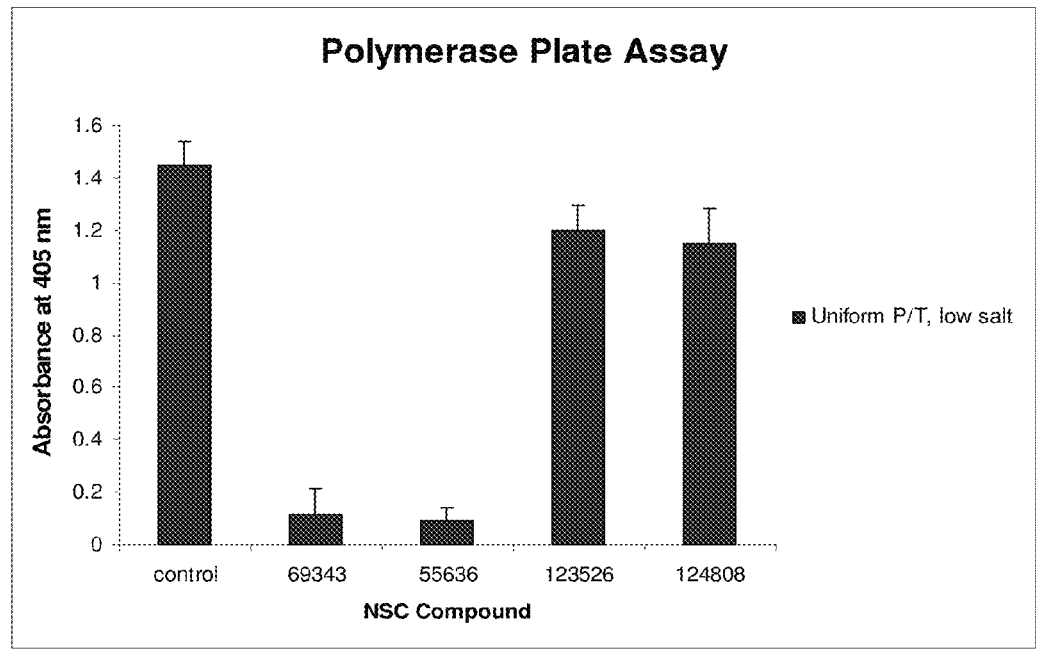
Figure 4C:
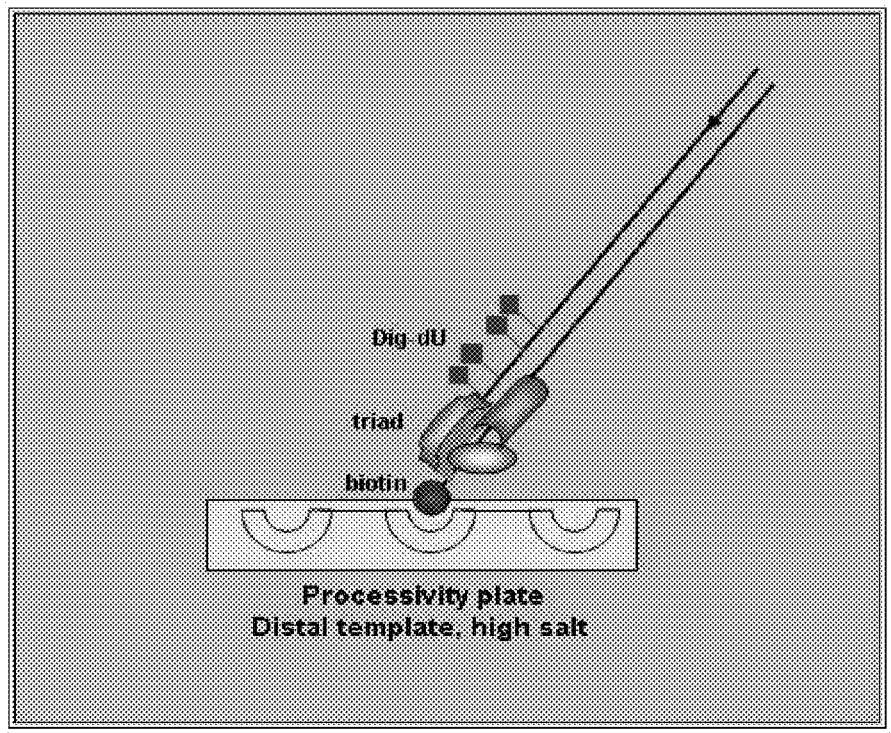
Figure 4D:
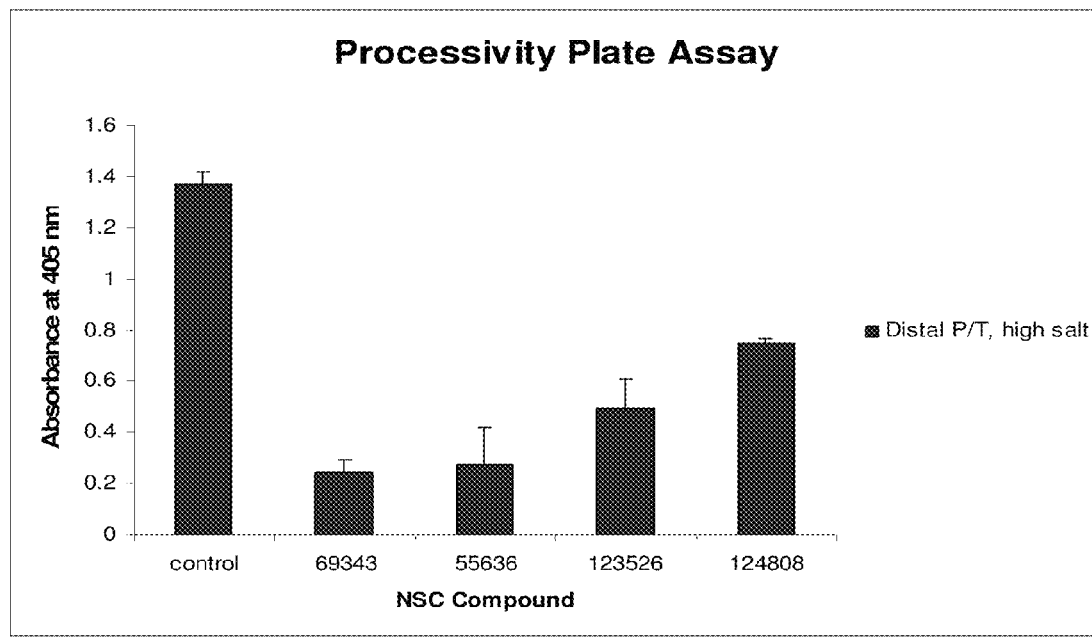

To distinguish polymerase from processivity inhibitors, altered versions of the plate assay were employed. To define polymerase inhibitors, E9 activity was examined in low salt. In low salt, DNA polymerases were able to synthesize fully extended strands in the absence of processivity factors. The uniform template, which contains evenly distributed sites for DIG-dU incorporation, was used to test for polymerase inhibitors (FIG. 4A). By contrast, to identify processivity inhibitors, the experiments were performed in high salt, in which E9 exhibits limited nucleotide incorporation whereas processive strand synthesis by the A20, D4, E9 triad is preferred. To assay for processivity, the distal template was used to allow DIG-dU to be incorporated only at the distal 3' end of the nascent DNA. Two compounds (69343 and 55636) were designated as polymerase inhibitors since they prevented E9 from incorporating nucleotides on the uniform template (FIG. 4B). As expected, these polymerase inhibitors also blocked the distal template (FIG. 4D), since vaccinia DNA synthesis is dependent on the incorporation of dNTPs by E9. In contrast, two compounds (123526 and 124808) were designated as processivity inhibitors since they prevented DNA synthesis by the triad on the distal template (FIG. 4D) but not on the uniform template (FIG. 4B).

Of the 47 compounds that passed Step II, 43 compounds did not inhibit either the polymerase or processivity assays. This result was due to the different protein sources used—infected cell lysate in Step I vs. in vitro translated proteins in Step III. Thus screening stringency can be greatly increased by switching from one protein source to another.

Step IV. M13 DNA Synthesis Assay

The ability of compounds to inhibit DNA synthesis in the rapid plate assay was confirmed using the M13 DNA synthesis assay. In the M13 assay, full-length DNA strands of 7,249 nucleotides are produced and visualized by autoradiography. Because of the length of the product, the M13 assay served as a rigorous test for processive DNA synthesis. As shown in FIG. 5, lane 2, full-length double stranded M13 DNA was successfully synthesized in the presence of the A20, D4, E9 triad. The brackets shown in FIG. 5 indicate the formation of greater than unit length products. The synthesis of M13 DNA was blocked by increasing concentrations of the two polymerase inhibitors NSC 69343 (lanes 3-7) and NSC 55636 (lanes 8-12), and the two processivity inhibitors NSC 123526 (lanes 13-17) and NSC 124808 (lanes 18-22). Most notably, the polymerase inhibitor NSC 69343 completely inhibited M13 DNA synthesis at 100 µM (lane 5). All of the other compounds inhibited at concentration between 100 µM and 1 mM.

Step V. Plaque Reduction Assay

A plaque reduction assay was used to evaluate the antiviral activity of the two polymerase inhibitors and the two processivity inhibitors that were selected from the screening assays (FIG. 6). BSC-1 cells were infected with 100-150 pfu of vaccinia virus and the inhibitors were added to the cell monolayer 1 h post-infection at a final concentration of 100 µM. This final concentration of 100 µM was based on the ability of known inhibitors to reduce plaque formation by approximately 50% following infection of BSC-1 cells by vaccinia virus. The results are summarized in Table I. Surprisingly, NSC 69343, the more potent polymerase inhibitor based on in vitro assays, was less remarkable in its ability to reduce viral plaques (40%), as compared to NSC 55636, the less potent polymerase inhibitor, which caused significant plaque reduction (95%). As for the two processivity inhibitors, NSC 123526 showed appreciable plaque reduction (72%) as compared with NSC 124808 (36%).

Step VI. Cytotoxicity Assay

Cytotoxicity of the four inhibitors of vaccinia DNA synthesis was determined using the aCella-Tox assay. This assay quantifies the cellular release of glyceraldehyde-3-phosphate dehydrogenase (G3PDH) which is essential for the production of ATP in the glycolysis pathway. G3PDH released into the cell media is used in a coupled reaction to generate ATP, which is then detected by luciferase/luciferin bioluminescence. As indicated in Table I and FIG. 6, at 100 μM, all of the inhibitors resulted in cell cytotoxicity lower than 50%. The two processivity inhibitors (NSC 123526 and 124808) exhibited the same levels of cytotoxicity (21%) whereas the polymerase inhibitors (NSC 55636 and 69343) exhibited toxicities of 14% and 17% respectively. Most interestingly, the least cytotoxic inhibitor, NSC 55636, is also the most potent plaque reducer.

Cellular Therapeutic Indices for Polymerase Inhibitor NSC 55636 and Processivity Inhibitor NSC 123526

The polymerase inhibitor NSC 55636 and processivity inhibitor NSC 123526 were considered to be the most significant compounds based on their efficacy at reducing vaccinia virus plaques with the least cytotoxicity. To establish the cellular therapeutic index $$\left\{ \text{Therapeutic Index}\,(TI) = \frac{\text{Cell Cytotoxicity}\,(CC_{50})}{\text{Effective Concentration}\,(EC_{50})} \right\}$$

for each compound, plaque reduction and cell cytotoxicity at a range of concentrations between 100 nM-200 μM was measured (Table 2). NSC 55636 gave a plaque reduction $EC_{50}$ of 5 μM and CC50 of greater than 200 μM, resulting in a cellular TI of greater than 40. NSC 123526 gave a plaque reduction $EC_{50}$ of 65 μM and CC50 of greater than 200 μM, resulting in a cellular TI of greater than 3.

These experimental settings provided: the selection of functional inhibitors that block vaccinia DNA synthesis; elimination of general and irrelevant inhibitors; distinguish whether the polymerase or the processive mechanism is targeted. The first screening step, which uses infected cell lysate, was designed for poxviruses, which are unique amongst the DNA viruses in that they replicate in the cytoplasm. This provides a great advantage since there are no competing nuclear polymerases in the cytoplasmic lysate that contribute to anomalous results. The second screening step eliminates irrelevant inhibitors such as DNA intercalators and DNA groove binders. Moreover, this step identifies antiviral compounds that were directed against viral polymerases. The third screening step, which distinguishes inhibition of the polymerase or processive mechanism, is also applicable to other viruses and eukaryotes that engage processivity complexes in their DNA synthesis. Using this stepwise approach, promising therapeutics that target the processivity complex of poxviruses were successfully found.

The stepwise screening delivered two compounds which have distinct modes of inhibiting polymerase/processive vaccinia DNA synthesis. The first compound, NSC 55636, inhibited the catalytic activity of E9 DNA polymerase (Tables 1 and 2). By contrast, the second compound, NSC 123526, inhibited the processive activity of the triad A20, D4 and E9 (Tables 1 and 2).

The polymerase inhibitor NSC 55636, also known as Fentichlor, is an antibacterial, anthelmintic and antifungal agent. This study shows that NSC 55636 is a promising poxvirus inhibitor due to its high cellular therapeutic index of greater than forty, reflecting its ability to effectively block vaccinia virus infection with minimal cytotoxicity.

The processivity inhibitor NSC 123526, is an S-fluorenylcysteine compound. The cysteine moiety renders the compound cell permeable and delivers the flourenyl group to the interaction site, inducing local conformational changes.

This study has yielded two other compounds that were effective in blocking vaccinia DNA synthesis in the in vitro rapid plate assays, while not as effective in cell-based assays. The polymerase inhibitor NSC 69343 is in fact tetracycline, an antibiotic that inhibits the prokaryotic 30S ribosome (Tables 1 and 2).

In summary, the sequential rapid plate screening provides a clear route for the identification of lead compounds with inhibitory activities towards poxvirus DNA synthesis. The stepwise design incorporated filters that (i) examined compounds that block viral DNA synthesis, (ii) selectively removed compounds that inhibited DNA synthesis in a general or irrelevant manner, and (iii) distinguish whether the inhibitors were blocking polymerase or processive mechanisms. This screening strategy yielded two candidate compounds for vaccinia, NSC 55636 and NSC 123526, representing a hit rate of 0.1%. Characterization of the A20, D4, E9 triad will provide insights into the mechanism of inhibition by these compounds and allow us to generate analogs that achieve maximum antiviral activity. The sequential screening approach can be modified to identify polymerase and processivity inhibitors of other viruses and microbial agents.

Design and Optimization of the Rapid Plate Assay for High-Throughput Screen

Infected cytoplasmic extracts were used as the source of viral proteins for the rapid plate assay. Poxviruses are unique amongst DNA viruses in that their replication occurs solely within the cell cytoplasm. This provided an advantage for preparing viral replication proteins that were free of nuclear enzymes involved in cellular DNA synthesis. Cytoplasmic extracts, prepared from vaccinia-infected BSC-1 cells, were shown to be completely separated from nuclear proteins, as verified by Western blot with the cytoplasmic marker β-Actin and the nuclear marker Rb1 (FIG. 7A). Moreover, cytoplasmic extracts of uninfected cells had little to no DNA synthesis activity, further indicating that the DNA synthesis activity of infected cell extracts was exclusively due to vaccinia cytoplasmic components and not to nuclear contaminants (FIG. 7B). Before proceeding with the major high-throughput screening (HTS), the assay was adapted to a 384-well platform. DNA synthesis reactions were performed in streptavidin-coated, 384-well plates for 30 minutes at 37 C, in a final reaction volume of 30 μL. Each well contained 100 mM ammonium sulfate, 0.5 μM digoxigenin-11-2'-2 deoxy-uridine-5'-triphosphate, 2 pmoles biotinylated primer-template and 0.2 mU vaccinia DNA polymerase (see Methods for details). The assay was evaluated for plate uniformity and signal variability by testing three plates on two different days. No drift or edge effects were observed and the calculated values for signal-to-background, signal-to-noise, coefficient of variation, and screening window coefficient (Z'-factor) validated the assay as suitable for HTS. The results were reproducible and the screening window coefficient (Z'-factor) had an excellent value of 0.95. Next, the assay was validated by robotically testing 1,520 chemical compounds with known pharmacological activities. Out of the 58 hit compounds that blocked the colorimetric reaction, 39 are known to bind DNA or inhibit DNA and RNA polymerases, which indicated that the assay is capable of detecting inhibitors of DNA synthesis. A survey of the current literature found that the remaining 19 hit compounds were never reported as inhibitors of DNA synthesis.

High-Throughput Screening for Inhibitors of Vaccinia-Dependent DNA Synthesis

The rapid plate assay was used to perform a robotic HTS to evaluate a total of 45,832 low-molecular-weight synthetic compounds (MW<500) and 2,311 natural extracts, that had been partially purified from endophytic fungi or plants used in traditional Chinese medicine (Table 3). All synthetic compounds and natural extracts, obtained as lyophilized solids, were dissolved in DMSO. The synthetic compounds from 11 independent libraries (Table 3) were each tested in duplicate, at a concentration of 16.7 µg/mL, equivalent to a molar concentration of 33-167 µM, depending on the molecular weight of the actual compound. The natural extracts, resuspended in DMSO at 15 mg/mL, were also tested in duplicate at 50 µg/mL final working concentration. From screening a total of 49,663 synthetic compounds and natural extracts, 829 inhibitors that block vaccinia virus DNA synthesis were identified, which represents a total hit rate of 1.6%. Inhibitors were classified as weak (30-50% inhibition), medium (50-70% inhibition), and strong (greater than 70% inhibition), based on the colorimetric intensity of the readout signal relative to the control signal obtained with no inhibitor (DMSO alone). Of the total number of 829 identified inhibitors, 178 were strong, 271 were medium, and 380 were weak inhibitors (Table 3). Interestingly, the percentage of natural extracts that inhibited DNA synthesis (hit rate) was much greater than that obtained with the synthetic compounds (Table 3) Likely, the DNA synthesis reaction is much more vulnerable to the plethora of chemical entities present in natural extracts than the singly purified compounds from synthetic libraries. Of note, the group of synthetic compounds with known biological activities had a greater hit rate than the synthetic compounds from combinatorial libraries, which is not surprising since many of these known compounds carry out their biological activities by modulating processes that involve DNA. 145 of the synthetic compounds that represented all of the strong and most of the intermediate inhibitors from the combinatorial synthetic libraries were retested. Of these 145 compounds, 135 were confirmed to block vaccinia DNA synthesis upon manual retesting in the rapid plate assay using 96-well plates. The 135 confirmed hit compounds were classified into 59 different chemical families based on their molecular structure. From these synthetic compounds, 93 strong and intermediate inhibitors that cover all structural families of the hit compounds were purchased and evaluated in follow-up studies. The natural extracts were not further pursued in this study, since they need to be fractionated in order to purify and identify the active components.

Dose-Dependent Inhibition of Vaccinia-Catalyzed DNA Synthesis and Determination of the $IC_{50}$ Values in the Rapid Plate Assay The 93 synthetic compounds (above) were analyzed in both enzymatic and in vitro cell-based assays. Compounds were suspended in DMSO at a final concentration of 20 mM and tested manually in the rapid plate assay for inhibition of DNA synthesis catalyzed by vaccinia proteins. The assay was performed in 96-well plates in conditions similar to those used for the primary high-throughput screen. Compounds were tested in triplicate over a range of concentrations and the percentage inhibition values were fitted to sigmoidal dose-response curves. For each compound a dose-dependent inhibition curve was generated, from which the 50% inhibitory concentration (IC50) was determined. The dose-response curves for five of the compounds is presented in FIG. 8. All chemicals inhibited vaccinia virus catalyzed DNA synthesis in the rapid plate assay. The IC50 values for 89 compounds ranged from 0.5 µM to 400 µM, while 4 compounds showed only partial inhibition at concentrations of 400 µM or higher.

Testing the DNA Synthesis Inhibitors for their Ability to Block Vaccinia Virus Infection In Vitro The 93 DNA synthesis inhibitors (above) were first tested in a plaque reduction assay to stop the formation of vaccinia virus plaques on BSC-1 cell monolayers. The plaque reduction assay uses a very low amount of vaccinia virus, just enough to give approximately 50 plaques in each well of a 48-well plate. Each compound was tested in triplicate and the results were used to estimate the compound concentrations for which the number of viral plaques was reduced to approximately half (effective concentration 50 or EC50) (Table 4). Next, the 93 compounds were tested in a cell protection assay. The cell protection assay was performed with amounts of virus capable of lysing every cell in the culture during the 20 hour incubation period. Compounds with antiviral properties preserve the monolayer's integrity and the adherent cellular mass is stained to generate the read-out signal (absorbance at 570 nm). Each compound was tested in triplicate over a range of concentrations up to 200 µM in two-fold serial increments and dose-dependent plots were generated by fitting the results on four-parameter sigmoidal response curves. These plots were used to calculate the compound concentrations at which 50% antiviral protection was observed, as compared to the unprotected DMSO control. While both these assays measure the antiviral activity, they differ by the amount of virus used to infect the cell monolayer. As it can be seen in Table 4, there is an overall concordance between the EC50 values obtained in the plaque reduction assay and the cell protection assay, which suggests that both assays are good indicators of a compound's efficacy to block viral infection.

Cytotoxicity of the Hit Compounds

The cell protection assay (above) indirectly measures the compounds' cytotoxicity, in that compounds which successfully protect against viral infection must do so without destroying the cells. Furthermore, the compounds' cytotoxicity was assessed in an assay that measures the metabolic activity of cells exposed to chemicals in the absence of virus. After culturing the cells in the presence of compounds, cell viability was determined by adding a cell-impermeable water-soluble tetrazolium salt that is reduced extracellularly to a dark-red soluble formazan and is monitored spectrophotometrically. Cytotoxicity was determined by measuring the reduction of tetrazolium salt due to metabolic activity of BSC-1 cells exposed to compounds, relative to DMSO alone. The percent cytotoxicity was fitted onto four-parameter sigmoidal dose response curves and the 50% toxic concentration values (TC50) were determined. As expected, cytotoxicity increases with the incubation time. Some compounds exhibited very little cytotoxicity in overnight cultures and their cytotoxic effects for 3 or 5-day incubation period were determined.

Compound Trapping by Extracellular DNA

The compounds identified using HTS were selected based on their ability to block vaccinia-catalyzed DNA synthesis irrespective of the mechanism of inhibition. Some of these inhibitors function by binding DNA and thus stopping DNA strand extension by polymerase. Such compounds affect indiscriminately many cellular and viral processes that involve DNA. To investigate if the hit compounds have affinity for DNA, antiviral activity was tested in the presence of large amounts of genomic double-stranded DNA added in the cell/virus culture. Since cells do not take up DNA under normal culturing conditions, this exogenous DNA remains outside the cells and traps any DNA-binding compound, resulting in (which leads to) a loss of that compound's antiviral activity.

Calculation of the Selectivity Index

The selectivity index for each compound was calculated as the ratio between the TC50 in the 20 hour cytotoxicty assay and the EC50 in the cell protection assay. Some compounds with very low toxicity had less than 50% cytotoxic effect at the highest tested concentration of 200 µM and their TC50's were estimated as greater than 200 µM in the 20 hours assay. It is noted that in order to obtain EC50 and TC50 values that can be compared to generate accurate SI's, the cell protection assay and the cytotoxicity assay need to be performed in similar conditions: fast-growing BSC-1 cells exposed to compounds or virus/compound mixtures for the same length of time.

Example 4

Inhibition of Vaccinia DNA Synthesis by Viridicatumtoxin

Viridicatumtoxin Inhibits Vaccinia DNA Synthesis In Vitro

Viridicatumtoxin and tetracycline were compared for their effectiveness in blocking DNA synthesis using the rapid plate assay. In this assay, DNA synthesis initiated from a primer annealed to a 100-nucleotide template. The primer-annealed template was tethered to a streptavidin-coated plate by a biotinylated moiety on its 5' end. DNA synthesis was conducted in low salt which enables vaccinia E9 DNA polymerase, produced by in vitro translation to perform extended strand synthesis. A failure to incorporate dNTPs in the presence of test compounds, i.e. viridicatumtoxin or tetracycline, indicates that E9 polymerase is inhibited. As seen in FIG. 10 and Table 5, the $IC_{50}$ values obtained for the inhibition of vaccinia DNA synthesis by tetracycline (54 µM) and viridicatumtoxin (63 µM) were similar.

Viridicatumtoxin Blocks Vaccinia Virus Infection

In order to evaluate the ability of viridicatumtoxin to inhibit vaccinia virus infection, a plaque reduction assay was employed. As represented in FIG. 11 and Table 5, viridicatumtoxin was able to reduce the number of plaques at near nanomolar concentrations ($IC_{50}$ of 1.6 µM). It is noted that at very high concentrations of viridicatumtoxin (≥100 µM), the cells began to detach. By contrast, tetracycline was ineffective at reducing vaccinia plaques ($IC_{50}$>200 f M).

Viridicatumtoxin Exhibits Low Cellular Cytotoxicity

To determine the cytotoxicity of viridicatumtoxin on cells, the aCella-TOX assay was used. This assay quantifies the cellular release of glyceraldehyde-3-phosphate dehydrogenase (GAPDH) which is essential for the production of ATP in the glycolysis pathway. Briefly, GAPDH that is released into the cell media is used in a coupled reaction to generate ATP, which can be detected by luciferase/luciferin bioluminescence. The $CC_{50}$ for viridicatumtoxin in the GAPDH release assay was greater than 200 µM (Table 5), indicative of low cellular cytotoxicity. The therapeutic index value for viridicatumtoxin, calculated from the cell cytotoxicity $CC_{50}$ and plaque reduction $IC_{50}$, was greater than 125.

Viridicatumtoxin does not Affect Cell Viability at the Plaque $IC_{50}$

Two different assays were used to determine the viability of the cells at the $IC_{50}$ concentration of viridicatumtoxin (1.6 µM). About 90% of the cells remained viable as determined by the cell count assay, and about 85% of the cells remained viable as measured by the MTT assay (Table 5).

Viridicatumtoxin Prevents Vaccinia Virus Late Gene Expression

Late viral gene expression is dependent upon vaccinia DNA synthesis. To test if viridicatumtoxin prevents expression of vaccinia late genes, but not early genes, representative viral marker genes were used to evaluate early and late vaccinia expression in the presence and absence viridicatumtoxin. A quantitative RT-PCR analysis to detect early and late viral mRNA production was performed first. RNAs from different time points of viridicatumtoxin-treated (20 µM) and untreated vaccinia virus infected cells were converted into cDNAs using oligo-dT. Specific primer pairs were used to amplify regions of the vaccinia early E3 vaccinia late F9 and cellular GAPDH cDNAs by quantitative real time PCR. For quantitation, GAPDH was used to normalize the levels of E3 and F9. As shown in FIG. 12A, both in the presence and absence of viridicatumtoxin, production of early E3 mRNA was maximum at 3 h.p.i. and dropped back to low levels by 5 h.p.i. By contrast, as shown in FIG. 12B, in the absence of viridicatumtoxin, the production of late F9 mRNA began to increase at 5 h.p.i. and continued to increase thereafter. However, in the presence of viridicatumtoxin, there was only a marginal increase in F9 mRNA expression by 5 h.p.i. that plateaued until the last time point (8 h.p.i.). The prevention of vaccinia late mRNA expression by viridicatumtoxin was substantiated by examining vaccinia early and late marker proteins by western blot analysis. As shown in FIG. 13, in untreated infected cells, the E3 marker protein appeared at 2 h post-infection, and continued to increase to the last time point (8 h.p.i.). In the presence of viridicatumtoxin, there was only a slight delay in appearance of E3 (3 h.p.i.). However, there is no significant difference in the levels of E3 in the presence or absence of viridicatumtoxin at 5 and 8 h.p.i. By contrast, the vaccinia late marker protein L1 which is involved in viral assembly (26, 27) (31), was significantly decreased in the presence of 20 µM viridicatumtoxin both at the time of its appearance at 5 h.p.i. as well as at 8 h.p.i. This ability of viridicatumtoxin to block late viral protein expression is in accord with its ability to inhibit late mRNA expression.

TABLE 1

| | | Targeted Activity | Inhibition of | Cell |
|---|---|---|---|---|
| NSC Inhibitor | Structure | (% Inhibition) | plaques* | Cytotoxicity* |
| 123526 | 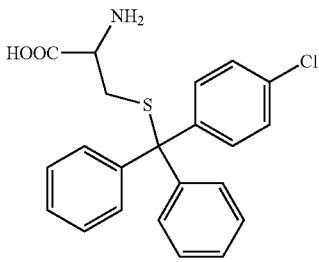 [SMILES: NC(CSC(c1ccccc1)(c1ccccc1)c1ccc(Cl)cc1)C(=O)O] | Processivity (64%) | 72% | 21% |
| 124808 | 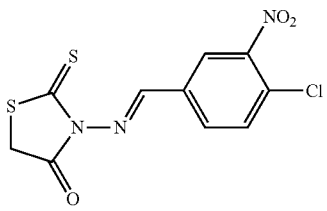 [SMILES: O=C1CSC(=S)N1/N=C/c1ccc(Cl)c([N+](=O)[O-])c1] | Processivity (62%) | 36% | 21% |
| 55636 | 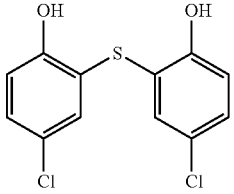 [SMILES: Oc1ccc(Cl)cc1Sc1cc(Cl)ccc1O] | Polymerase (74%) | 95% | 14% |
| 69343 | 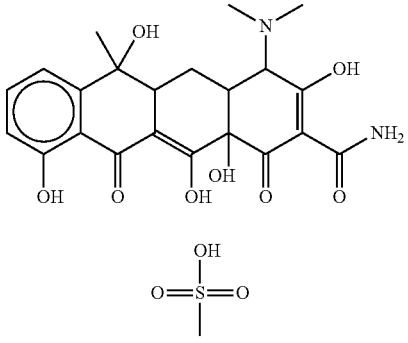 | Polymerase (92%) | 40% | 17% |

*All compounds were tested at a fixed concentration of 100 μM.

TABLE 2

The efficiency of NSC 55636 and NSC 123526 as vaccinia inhibitors

| Inhibitor compound | CC50[a] | EC$_{50}$[b] | TI[c] |
|---|---|---|---|
| NSC 55636 | >200 μM | 5 μM | >40 |
| NSC 123526 | >200 μM | 65 μM | >3 |

Table 2.
[a]Concentration at which compound is 50% cytotoxic
[b]Concentration at which compound reduced plaques by 50%
[c]Ratio of CC50 to EC$_{50}$

TABLE 3

| | | | Hit rate | | |
|---|---|---|---|---|---|
| Library Type | Library Name | Number of Compounds in Library | Strong Inhibition >70% Inhibition | Intermediate Inhibition 50%-70% Inhibition | Weak Inhibition 30%-50% Inhibition |
| Known Bioactives | Biomol IOCB Known Bioactives | 480 | 6 (1.3%) | 8 (1.7%) | 11 (2.3%) |
| | NINDS Custom Collection | 1,040 | 15 (1.4%) | 8 (0.8%) | 10 (1.0%) |
| Natural Extracts | Starr Foundation Extracts 2 | 1,000 | 43 (4.3%) | 41 (4.1%) | 57 (5.7%) |
| | ICBG Fungal Extracts 1 | 851 | 59 (6.9%) | 57 (6.7%) | 54 (6.3%) |
| | ICBG Fungal Extracts 2 | 460 | 18 (3.9%) | 30 (6.5%) | 24 (5.2%) |
| Synthetic Compounds | ChemDiv 3 | 16,544 | 21 (0.1%) | 64 (0.4%) | 89 (0.5%) |
| | MixCommercial 5 | 268 | 0 (0.0%) | 0 (0.0%) | 1 (0.4%) |
| | Maybridge 4 | 4,576 | 2 (<0.1%) | 9 (0.2%) | 28 (0.6%) |
| | ActiMol TimTec 1 | 8,518 | 6 (0.1%) | 19 (0.2%) | 25 (0.3%) |
| | Bionet 2 | 1,700 | 2 (0.1%) | 2 (0.1%) | 14 (0.8%) |
| | Enamine 1 | 6,004 | 1 (<0.1%) | 9 (0.1%) | 19 (0.3%) |
| | I.F. Lab 1 | 6,543 | 4 (0.1%) | 17 (0.3%) | 40 (0.6%) |
| | I.F. Lab 2 | 292 | 0 (0.0%) | 4 (1.4%) | 0 (0.0%) |
| | Maybridge 2 | 704 | 1 (0.1%) | 1 (0.1%) | 5 (0.7%) |
| | MixCommercial 4 | 331 | 0 (0.0%) | 1 (0.3%) | 3 (0.9%) |
| | Peakdale 2 | 352 | 0 (0.0%) | 1 (0.3%) | 0 (0.0%) |
| | Total | 49,663 | 178 (Hit Rate 0.4%) | 271 (Hit Rate 0.5%) | 380 (Hit Rate 0.8%) |

TABLE 4

Summary of activities

| Compound | DNA Synthesis Inhibition IC50 (uM) | Cell Protection 20 h EC50 (uM) | Plaque Reduction 20 h EC50 (uM) | Cytotoxicity 20 h CC50 (uM) | Cytotoxicity 72 h CC50 (uM) | Cytotoxicity 120 h CC50 (uM) | Selectivity Index SI | Effect of dsDNA |
|---|---|---|---|---|---|---|---|---|
| 1304-M19 | 42 | 23 | 25 | 100 | | | 4.3 | Yes |
| 1306-M02 | 56 | 12 | 6 | 23 | | | 1.9 | Yes |
| 1394-F14 | 131 | 50 | 50 | >200 | 36 | 3 | >4.0 | No |
| 1398-K11 | 25 | 87 | 100 | >200 | 152 | 60 | >2.3 | Yes |
| 1410-N05 | 5.6 | 25 | 10 | 20 | | | 0.8 | Yes |
| 1417-H08 | 30 | 40 | 25 | 87 | | | 2.2 | Yes |
| 1421-J18 | 374 | 30 | 25 | 159 | | | 5.3 | No |
| 1427-G18 | 108 | 9.6 | 10 | 127 | | 20 | 13.2 | No |
| 1429-L06 | 46 | 100 | 50 | >100 | 13 | 30 | >1 | No |
| 1430-M18 | 188 | 90 | 25 | 166 | | 25 | 1.8 | No |
| 1488-G10 | 25 | 14 | 25 | 133 | | | 9.5 | Yes |
| 1488-N05 | 708 | 193 | 100 | >200 | 35 | | >1 | Yes |
| 1489-L17 | 25 | 57 | 40 | >200 | | 12 | >3.5 | Yes |
| 1489-N17 | 18 | 57 | 25 | >200 | | 10 | >3.5 | Yes |
| 1492-H05 | 65 | 18 | 40 | 192 | | | 10.7 | Yes |
| 1501-M18 | 39 | 98 | 100 | 135 | | | 1.4 | Yes |
| 1502-N02 | 75 | 188 | 150 | >200 | >200 | 50 | >1 | No |
| 1502-O21 | 46 | 41 | 25 | 143 | | | 3.5 | Yes |
| 1504-J21 | 43 | 130 | 75 | >200 | 174 | 120 | >1.5 | No |
| 1508-M17 | 26 | 100 | 75 | >200 | 38 | 20 | >2 | No |
| 1513-N12 | 111 | 236 | 100 | >200 | >200 | 75 | >1 | No |
| 1522-I19 | 25 | 23 | 10 | 29 | | | 1.3 | Yes |
| 1523-L14 | 12 | 50 | 15 | 157 | | 40 | 3.1 | No |
| 1526-J08 | 26 | 104 | 75 | >200 | 30-50 | 20 | >1.9 | No |
| 1526-P05 | 129 | 45 | 15 | 115 | | 5 | 2.6 | No |
| 1530-J10 | 52 | 100 | 75 | >200 | | Pp at 100 | >2 | No |
| 1531-O02 | 30 | 95 | 75 | >200 | ~50 | 20 | >2.1 | No |
| 1537-L02 | 32 | 80 | 75 | >100 | >50 | | >1.2 | No |
| 1538-E21 | 239 | 100 | 50 | >100 | | | >1 | No |
| Cidofovir | | 132 | 50 | >2,500 | >500 | 300 | >18.9 | No |
| Ara-C | | 0.24 | 0.5 | 16 | | | 66.7 | Yes |
| Ethidium | | 100 | | | | | | Yes |
| Quinacrine | | 17 | | | | | | Yes |
| Aphidicolin | | 18 | | | | | | No |

TABLE 5

Summary of viridicatumtoxin inhibition of vaccinia virus DNA synthesis and infection.

| | E9 activity IC$_{50}$ (μM) | Plaque IC$_{50}$ (μM) | CC$_{50}$ | TI | % cell viability on plaque IC$_{50}$ | |
|---|---|---|---|---|---|---|
| | | | | | Cell count | MTT |
| Viridicatumtoxin | 63 ± 2.8 | 1.6 ± 2.4 | >200 | >125 | 92 ± 23 | 83 ± 16 |
| Tetracycline | 54 ± 2.1 | >200 | >200 | ND | ND | ND |

Example 5

Identification of Non-Nucleoside DNA Synthesis Inhibitors of Vaccinia Virus by High Throughput Screening Experimental Details Primary High-Throughput Screen For HTS, the rapid plate assay was adapted to a robotic platform. The DNA synthesis reactions were performed in 384-well plates coated with streptavidin (SigmaScreen plates, Sigma-Aldrich cat. no. S8686). In each well, reactions were conducted with 0.5 μL of vaccinia virus to extract containing 0.2 mU DNA polymerase activity in 20 mM Tris-Cl pH7.5, 100 mM ammonium sulfate, 5 mM MgCl$_2$, 0.1 mM EDTA, 0.5 mM DTT, 4% glycerol, 40 μg/mL BSA, 5 μM each of dATP, dCTP, and dGTP, 4 μM dTTP, 0.5 μM DIG-11-dUTP, in a total volume of 30 μL. Two pmol of biotinylated primer-template dissolved in 30 μL PBS were immobilized on streptavidin-coated wells. The unbound primer template was removed, and the wells were washed twice with 50 μL of PBS and loaded with 20 μL reaction buffer (20 mM Tris-Cl pH7.5). Then 100 nL of each compound or natural extract dissolved in DMSO were transferred from the library plates by an Epson transfer robot (Epson Robots, Carson, Calif.) fitted with a 384-pin array. DNA synthesis was initiated by loading 10 μL of a 3× reaction mixture. After brief centrifugation, plates were incubated at 37° C. for 30 mM The DNA synthesis reaction was stopped with 30 μL of a solution containing 50 mM EDTA and 2% SDS in 10 mM Tris pH 8. Incorporation of DIG-11-dUTP in the newly synthesized DNA strand was detected with peroxidase-conjugated anti-digoxigenin antibody (anti-DIG-POD). Wells were flow-washed with 400 μL of PBS containing 0.1% Tween-20 at the lowest dispensing speed and loaded with 4.5 mU of anti-DIG-POD in 30 μL of PBS/blocking solution. After gently rocking at room temperature for 1 h, the antibody solution was removed and wells were flow-washed as above. Then 30 μL of 2,2′-azino-bis(3-ethylbenzthiazoline)-sulfonate (ABTS) peroxi-dase substrate dissolved in citrate buffer was added and plates were gently rocked at room temperature for 1 h. Color development was stopped with 1.0 μL of 4% SDS and absorbance at 405 nm was measured. Readings from each well were divided by the plate median, and the percent inhibition was determined relative to the values of uninhibited reaction controls.

Cytoplasmic Extracts of Vaccinia-Infected BS-C-1 Cells

Confluent BS-C-1 cells, infected with vaccinia virus WR at an MOI of 15 in the presence of 10 mM hydroxyurea, were harvested 6 h post infection. Hydroxyurea inhibits viral DNA replication and transcription of intermediate and late viral mRNA's, allowing only the expression of early gene products and not the abundant late viral genes. Processive DNA synthesis is an early activity of the vaccinia virus and thus is not affected by hydroxyurea. Infected cells were carefully scraped off the plates, washed once with hypotonic buffer (1.5 mM MgCl$_2$, 10 mM KCl, 10 mM Hepes pH 7.5), resuspended in cold hypotonic buffer, incubated on ice for 10 min, and lysed by gentle dounce homogenization. Nuclei were removed by centrifugation at 1000 g for 10 min. The cytoplasmic extracts were filtered twice through 0.2 μm and shown to be free of infectious particles as determined by plaque assay. Glycerol was added to 20% final concentration, and aliquots were stored at −80° C.

Screened Libraries

The 1520 chemical compounds with known biological activities used for assay validation were from two collections: BIOMOL ICCB Known Bioactives 1 (480 compounds) and NINDS Custom Collection (1040 compounds). A total of 45832 synthetic compounds, representing 11 independent libraries (ChemDiv 3 (16544 compounds), MixCommercial 5 (268 compounds), Maybridge 4 (4576 compounds), Acti-Mol TimTec 1 (8518 compounds), Bionet 2 (1700 compounds), Enamine 1 (6004 compounds), I.F. Laboratory 1 (6543 compounds), I.F. Laboratory 2 (292 compounds), Maybridge 2 (2704 compounds), MixCommercial 4 (331 compounds), and Peakdale 2 (352 compounds)) were tested in duplicate at a single concentration of 16.7 μg/mL, which is equivalent to a molar concentration of 33-167 μM, depending on the molecular weight of each individual compound. Natural extracts with inhibitory activity were identified by screening the Stan' Foundation Extracts 2 library (1000 extracts from plants used in traditional Chinese medicine), and two collections of partially purified extracts from endophytic fungi: ICBG Fungal Extracts 1 (851 extracts) and ICBG Fungal Extracts 2 (460 extracts). The natural extracts, resuspended in DMSO at 15 mg/mL, were also tested in duplicate at 50 μg/mL final working concentration. The chemical libraries were supplied by the National Screening Laboratory for the Regional Centers of Excellence in Biodefense and Emerging Infectious Disease (NSRB) at the Harvard Institute of Chemistry and Cell Biology (ICCB, Harvard Medical School), where the robotic HTS was performed.

DNA Synthesis Assay

Milligram quantities of the HTS hit compounds for follow-up studies were purchased from various vendors and suspended in DMSO at a final concentration of 20 mM. Each hit compound was retested over a range of concentrations for its ability to inhibit vaccinia virus DNA synthesis. Assays were performed in 96-well plates in conditions similar to those for the HTS. Each compound was tested in triplicate in 2-fold serial dilutions, and the IC50 was calculated with the Prism software (GraphPad Software, Inc.) for linear regression.

Viral Plaque Reduction Assay

BS-C-1 cells were maintained in Dulbecco's modified Eagle medium (DMEM) to containing 10% fetal bovine serum (FBS), 50 mg/L gentamicin sulfate (Gibco BRL Life Technologies, Gaithersburg, Md.), and grown at 37° C. in a humidified atmosphere with 5% CO2. For the plaque reduction assay, 6×10$^4$ cells/well were seeded in 48-well plates and allowed to attach overnight. Cells were infected with 50 plaque forming units (pfu)/well of vaccinia virus WR in the presence of the HTS hit compounds at various concentrations. After 20 h, cells were fixed with 5% formaldehyde in PBS and stained with 0.2% crystal violet dissolved in 50% ethanol. Wells were washed, dried, and plaques were counted under the microscope. The EC50 values were estimated as the concentration of compound that caused a reduction in the number of plaques by 50%.

Viral Cell Protection Assay

The cell protection assay was performed using similar conditions to the plaque reduction assay. BS-C-1 cells were seeded in 96-well plates at $1.5 \times 10^4$ cells/well and grown overnight. The cells were infected with 2000 pfu/well of vaccinia virus WR in the presence of inhibitors. After incubating at 37° C. for various times (20, 48, and 72 h), cells were fixed with formaldehyde and stained with crystal violet. The excess dye was washed away, and the cellular mass fixed on the bottom of the wells was allowed to dry overnight. Absorbance at 570 nm was measured. Each compound was tested in triplicate in 2-fold serial dilutions, and EC50 values were calculated using the Prism software for linear regression.

DNA Trap Assay

To investigate if the hit compounds retain their antiviral potency in the presence of exogenous DNA, the cell protection assay was performed with 400 µg/mL of type DI DNA, sodium salt, from salmon testes (Sigma, Saint Louis, Mo.) added in the growth medium. The final concentration of compound-derived DMSO was 1% (v/v) in all cell-based assays. For the control wells that contained no compound, an appropriate volume of DMSO was added to achieve a final concentration of 1%.

Cytotoxicity Assay

Compound cytotoxicity was measured with the Cell Proliferation Reagent WST-1 (Roche Applied Science, Indianapolis, Ind.) following the manufacturer's protocol. BS-C-1 cells were seeded in 96-well plates at 5000 cells/well in 50/µL growth medium without phenol red. Next day, 50 µL/well of growth medium containing the tested compounds were added and cultures were grown for 20 h at 37° C. Then 10 µL of WST-1 reagent were added to each well, plates were incubated at 37° C. for 30 min, and absorbance at 450 nm was measured. Each to compound was tested in triplicate in 2-fold serial dilutions, and TC50 values were calculated using the Prism software for linear regression. To measure the compound cytotoxicity over longer incubation periods, the number of BS-C-1 cells seeded was adjusted: 1000 cells/well for 3-day cytotoxicity and 200 cells/well for 5-day cytotoxicity. This ensured that cells did not grow past confluency by the end of the experiment and that the read-out signal remained in the linear range.

Results

Identification of Small Chemical Inhibitors of Vaccinia Virus DNA Synthesis with a Rapid Plate Assay Designed for High-Throughput Screening.

Inventor of the instant application has developed a rapid plate assay to identify inhibitors of vaccinia virus DNA synthesis that target the viral DNA polymerase and its associated factors required for processivity. Briefly, a 5'-biotinylated DNA template annealed to an oligonucleotide primer at its 3'-end is immobilized onto streptavidin-coated wells. In the presence of the viral polymerase and its associated factors, dNTP's and digoxigenin-labeled 2'-deoxy-uridine-5'-triphos-phate (DIG-11-dUTP) are incorporated into the newly synthesized DNA strand. DNA synthesis activity is measured by the detection of digoxigenin using an enzyme-linked antibody that generates a colorimetric reaction.

Replication of poxviruses occurs solely within the cytoplasm. Cytoplasmic extracts from infected BS-C-1 cells were used as the source of vaccinia proteins for the rapid plate assay. These cytoplasmic extracts were confirmed to be completely free of nuclear proteins by Western blot with antibody specific for the nuclear marker retinoblastoma protein Rb1 (FIG. 7A). Moreover, cytoplasmic extracts of uninfected cells had little to no DNA synthesis activity in the rapid plate assay, indicating that the DNA synthesis activity of infected cell extracts was exclusively due to vaccinia cytoplasmic proteins and not to nuclear enzymes involved in cellular DNA synthesis (FIG. 7B).

Before proceeding with the HTS, the rapid plate assay was adapted for use with the Epson compound transfer robot (Epson Robots, Carson, Calif.). DNA synthesis reactions were optimized without inhibitors in streptavidin-coated 384-well plates. This robotic procedure exhibited plate uniformity and no signal variability when tested in multiple plates on different days. No drift or edge effects were observed, and the calculated values for signal-to-background, signal-to-noise, coefficient of variation, and screening window coefficient (Z'-factor) validated the assay as suitable for HTS. The robotic plate assay was reproducible, and the Z'-factor had an excellent value of 0.95.

Next, the optimized assay was validated by testing 1520 chemical compounds with known pharmacological activities. These known bioactive compounds are compiled in two libraries and include more than half of the drugs currently approved by the Food and Drug Administration. Out of the 58 compounds that blocked the colorimetric reaction of the rapid plate assay, 39 are known to bind DNA or inhibit DNA or RNA polymerases, which confirmed that the assay was indeed capable of detecting inhibitors of DNA synthesis. Interestingly, with respect to the remaining 19 known compounds, this is the first report to reveal that they are capable of inhibiting DNA synthesis.

The optimized robotic plate assay was then used to identify novel vaccinia DNA synthesis inhibitors by performing a HTS of 45832 small synthetic compounds (MW<500) and 2311 partially purified natural extracts. In this primary screen, the inventor identified 383 natural extracts and 446 synthetic compounds that inhibited vaccinia virus DNA synthesis, representing a hit rate of 1.6%. An extensive survey of the current literature showed that the majority of these hit compounds were never reported to function as inhibitors of DNA or RNA synthesis. Of the total 829 hit compounds, 178 were ranked as strong (greater than 70% inhibition), 271 were ranked as intermediate (50-70% inhibition), and 380 were ranked as weak (30-50% inhibition) based on the colorimetric intensity of the read-out signal relative to the control signal obtained with no inhibitor (DMSO alone). Interestingly, the percentage of natural extracts that inhibited DNA synthesis was greater than that of the synthetic compounds. Likely, the DNA synthesis reaction is more vulnerable to the multitude of chemical entities present in natural extracts than the singly purified compounds from synthetic libraries. It is noted that the group of synthetic compounds with known biological activities also had a greater hit rate than the synthetic compounds from combinatorial libraries. This is not surprising because many of these known compounds have been shown to modulate activities that utilize DNA (e.g., topoisomerization).

At this point, the inventor of the instant application decided to pursue only the synthetic hit compounds because they have defined structures and are available as purified chemicals. These synthetic hit compounds represent a wide range of structures, which the inventor was able to classify into 59 different chemical families. All of the strong and most of the intermediate inhibitors from the combinatorial synthetic libraries were confirmed to block vaccinia DNA synthesis upon manual retesting in the 96-well rapid plate assay. Follow-up studies were conducted on 93 of the synthetic inhibitors from which all of the structural families are represented. These compounds were evaluated for potency in blocking vaccinia DNA synthesis in vitro, protecting cultured cells from infection with vaccinia virus, as well as cellular toxicity.

Potency of Hit Compounds in Blocking Vaccinia Virus DNA Synthesis In Vitro

The inhibitory concentrations (IC50) for each of the 93 synthetic compounds were determined. The assay was performed in 96-well plates using conditions similar to those used for the primary HTS. Each compound, dissolved in DMSO, was tested in triplicate over a range of concentrations for inhibition of DNA synthesis catalyzed by vaccinia proteins. The percentage inhibition values were fitted on sigmoidal dose-response curves from which the IC50 was determined. Three representative dose-response curves are presented in FIG. 14A. The $IC_{50}$ values for 89 compounds ranged from 0.5 to 400 μM, while four compounds showed less than 50% inhibition at concentrations of 400 μM or higher (Tables 6 and 7).

Potency of Hit Compounds in Blocking Vaccinia Virus Infection In Vitro

The 93 DNA synthesis inhibitors were first tested in a plaque reduction assay to determine if they could prevent the formation of vaccinia virus plaques on BS-C-1 cell monolayers. For the plaque reduction assay, cells were infected at a low multiplicity of infection (moi) to generate approximately 50 vaccinia virus plaques in each well of a 48-well plate. Each compound was tested in triplicate over a range of concentrations, and the results were used to estimate the EC50, the effective concentration of compound required to reduce the number of viral plaques by 50%. The EC50 values for 75 compounds ranged from 5 to 200 μM, while 18 compounds had no effect on the number of plaques (Tables 6 and 7).

TABLE 6

Summary of Activities of 16 Synthetic Hit Compounds

| compd[a] | DNA synth $IC_{50}$ (μM) | cell prot $EC_{50}$ (μM) | plaque red $EC_{50}$ (μM) | tox 20 h $TC_{50}$ (μM) | tox 72 h $TC_{50}$ (μM) | tox 120 h $TC_{50}$ (μM) | selectivity index[b] | trapped by dsDNA |
|---|---|---|---|---|---|---|---|---|
| 1 | 108 | 9.6 | 10 | 127 | | 20 | 13.2 | no |
| 2 | 374 | 30 | 25 | 159 | | | 5.3 | no |
| 3 | 131 | 50 | 50 | >200 | 36 | 3 | >4.0 | no |
| 4 | 12 | 50 | 15 | 157 | | 40 | 3.1 | no |
| 5 | 129 | 42 | 15 | 155 | | 5 | 2.6 | no |
| 6 | 30 | 95 | 75 | >200 | 50 | 20 | >2.1 | no |
| 7 | 26 | 100 | 75 | >200 | 38 | 20 | >2 | no |
| 8 | 52 | 100 | 75 | >100 | >100 | >100 | >2 | no |
| 9 | 26 | 104 | 75 | >200 | 40 | 20 | >1.9 | no |
| 10 | 188 | 90 | 25 | 166 | | | 1.8 | no |
| 11 | 43 | 130 | 75 | >200 | 174 | 120 | >1.5 | no |
| 12 | 32 | 80 | 75 | >100 | >100 | 50 | >1.2 | no |
| 13 | 46 | 100 | 50 | >100 | 13 | 30 | >1 | no |
| 14 | 75 | 188 | 150 | >200 | >200 | 50 | >1 | no |
| 15 | 111 | 236 | 100 | >200 | >200 | 75 | >1 | no |
| 16 | 239 | 100 | 50 | >100 | >100 | 50 | >1 | no |
| CDV | | 132 | 50 | >500 | >500 | 300 | >3.8 | no |

[a]Refer to Chart 1 for the structures of compound 1-16.
[b]The selectivity index was obtained as the ration between $TC_{50}$ in the 20 h cyotoxicity assay and $EC_{50}$ in the 20 h cell protection assay.

TABLE 7

Structures and IC50 Values for 19 Synthetic Compounds that are Strong Inhibitors of Vaccinia DNA Synthesis in Vitro

| Library[b] | Compound Structure | DNA Synthesis $IC_{50}$ (μM) |
|---|---|---|
| 1 | 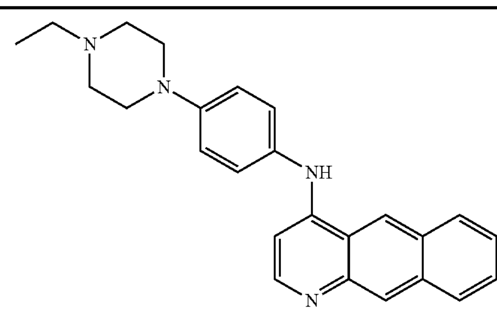 | 0.5 |
| 5 | 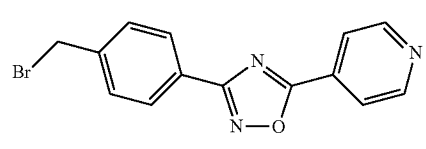 [SMILES: BrCc1ccc(-c2noc(-c3ccncc3)n2)cc1] | 1.3 |

TABLE 7-continued

Structures and IC50 Values for 19 Synthetic Compounds that are Strong Inhibitors of Vaccinia DNA Synthesis in Vitro

| Library[b] | Compound Structure | DNA Synthesis IC$_{50}$ (μM) |
|---|---|---|
| 1 | | 3.0 |
| 1 | | 3.5 |
| 3 | 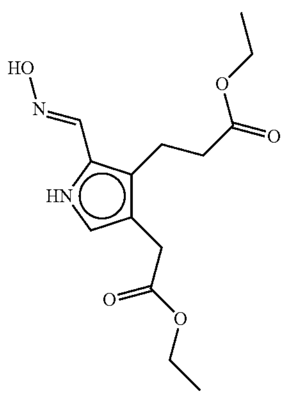 | 3.8 |
| 1 | | 4.0 |
| 1 | | 4.1 |

TABLE 7-continued

Structures and IC50 Values for 19 Synthetic Compounds that are Strong Inhibitors of Vaccinia DNA Synthesis in Vitro

| Library[b] | Compound Structure | DNA Synthesis $IC_{50}$ (μM) |
|---|---|---|
| 4 | | 5.0 |
| 4 | | 5.3 |
| 1 | | 5.4 |
| 1 | | 5.9 |
| 1 | | 6.0 |

TABLE 7-continued

Structures and IC50 Values for 19 Synthetic Compounds that are Strong Inhibitors of Vaccinia DNA Synthesis in Vitro

| Library[b] | Compound Structure | DNA Synthesis IC$_{50}$ (μM) |
|---|---|---|
| 3 | (structure) | 6.3 |
| 1 | (structure) | 6.7 |
| 1 | (structure) | 7.3 |
| 1 | (structure) | 7.4 |
| 4 | (structure) | 7.4 |

TABLE 7-continued

Structures and IC50 Values for 19 Synthetic Compounds that are Strong Inhibitors of Vaccinia DNA Synthesis in Vitro

| Library[b] | Compound Structure | DNA Synthesis IC$_{50}$ (μM) |
|---|---|---|
| 1 | (structure) | 10 |
| 1 | (structure) | 10 |

[a] These compounds do not have favorable antiviral activity in cell-based assays because they are either highly toxic or failed to block viral infection.
[b] The synthetic compounds belong to the following libraries: ChemDiv 3 (library 1); Maybridge 4 (library 3); ActiMol TimTec (library 4); and Bionet 2 (library 5).

CHART 1

STRUCTURES OF THE 16 MOST PROMISING SYNTHETIC HIT COMPOUNDS THAT INHIBIT VACCINIA VIRUS INFECTION[a]

1

2

3

CHART 1-continued

STRUCTURES OF THE 16 MOST PROMISING SYNTHETIC HIT COMPOUNDS THAT INHIBIT VACCINIA VIRUS INFECTION[a]

4

5

CHART 1-continued

STRUCTURES OF THE 16 MOST PROMISING SYNTHETIC HIT COMPOUNDS THAT INHIBIT VACCINIA VIRUS INFECTION[a]

[a]COMPOUNDS 7, 11, 15, AND 15 BELONG TO CHEMDIV 3 LIBRARY; COMPOUNDS 4, 5, 6, 8, AND 9 BELONG TO MAYBRIDGE 4 LIBRARY; COMPOUNDS 12 AND 16 BELONG TO ACTIMOL TIMTEC LIBRARY; COMPOUND 3 BELONGS TO ENAMINE 1 LIBRARY; COMPOUNDS 1, 2, 10, AND 13 BELONG TO I.F. LAB 1 LIBRARY.

Next, the 93 compounds were tested in a cell protection assay. This assay was performed with amounts of virus capable of lysing every cell in the culture during the 20 h incubation period. Compounds with antiviral properties protect the cell monolayer from infection, as determined by the cellular mass, stained for absorbance at 570 nm. Each compound was tested in triplicate over a range of concentrations up to 200 µM in 2-fold serial dilution increments. Dose-dependent plots were generated by fitting the results on four-parameter sigmoidal response curves. These plots were used to calculate for each compound the concentration at which 50% antiviral protection is obtained relative to the unprotected DMSO control (FIG. 14B). Twenty-nine of the 75 compounds that were active in the plaque assay also protected cells from viral infection with EC50 values as low as 9.6 µM (Table 6).

While both the plaque reduction and the cell protection assays measure the antiviral activity of compounds, they differ dramatically by the amount of virus used to infect the cell to monolayer. Nevertheless, as seen in Table 6, there is an overall concordance between the EC50 values obtained with these two assays, confirming the efficacy of these hit compounds in blocking viral infection.

Cellular Toxicity of Hit Compounds

The cell protection assay presented above indirectly measures cytotoxicity in that compounds that protect against viral infection must, a priori, perform this function without disrupting the cells. However, to directly assess the cytotoxicity of each of the 93 compounds, the inventor of the instant application employed a cytotoxicity assay that measures the metabolic activity of cells exposed to chemicals in the absence of virus. After culturing cells in the presence of inhibitors, cell viability was determined by spectrophotometrically measuring the reduction of a water-soluble tetrazolium salt to a dark-red formazan, which is catalyzed by a mitochondrial activity. The percent cytotoxicity relative to the DMSO control was fitted onto four-parameter sigmoidal dose-response curves and the 50% toxic concentration values (TC50) were determined. After 20 h, 15 compounds had negligible cytotoxicity even at the highest working concentration of 200 µM. Not surprisingly, longer incubation periods of 72 and 120 h led to increased cytotoxicity (Table 7).

On the basis of the results of cell culture assays, the 93 compounds fell into 3 groups: group I consisted of 18 compounds that had no effect on cells (Table 7); group II consisted of 46 compounds that inhibited viral infection but were cytotoxic at similar concentrations (Table 7); group III consisted of 29 compounds that inhibited viral infection at concentrations lower than the cytotoxic concentration (Chart 1, Table 6).

Of note, the 18 synthetic compounds from group I did not have any effect in cell-based assays when tested at concentrations up to 200 µM: they did not inhibit viral plaque formation, they did not protect cells from viral infection, and they did not show any cytotoxicity. All of these 18 compounds had tested positive in the rapid plate assay, some of them being very potent inhibitors of vaccinia DNA synthesis in vitro, with IC50 values as low as 1.3 µM (Table 7). This lack of antiviral activity and cytotoxicity is most probably due to the inability of these compounds to permeate the cell membrane. Chemical modifications that increase lypophilicity and cell permeability may confer antiviral activity to these in vitro DNA synthesis inhibitors and convert them into attractive lead compounds.

Selectivity Index of Hit Compounds

The selectivity index (SI) for each compound was calculated as the ratio between TC50 in the 20 h cytotoxicity assay and EC50 in the cell protection assay. Six compounds had a SI of 4 or higher, with the most effective compound having a SI of 13, reflecting the ability to block vaccinia virus infection at concentrations significantly lower than those producing cytotoxicity (Table 6). Of note, the SI for many compounds is a conservative estimate because 50% cytotoxicity was not attained at the highest tested concentration of 200 µM. (e.g., compound 3 in Table 6). As reference for antiviral activity, the inventor of the instant application tested the well-known antipoxvirus drug CDV, which functions as a chain terminator to inhibit viral DNA synthesis. CDV had a SI of greater than 4, which is in accord with the values previously reported. The compounds of the invention have potencies comparable to CDV, indicating their significance as potential poxvirus therapeutics.

Sixteen Hit Compounds Retain their Antiviral Activity in the Presence of a DNA Trap.

The compounds identified in our primary HTS were selected by their ability to block vaccinia virus DNA synthesis. Although many hit compounds are likely inhibit DNA synthesis by interfering with a specific mechanistic step (e.g., the catalytic incorporation of dNTP's by DNA polymerase), the inventor was concerned that some hit compounds bind to DNA (e.g., by intercalation), in which case they would nonspecifically inhibit DNA polymerases from incorporating nucleotides. To eliminate such nonspecific inhibitors, their antiviral activities were tested in the presence of large amounts of genomic double-stranded DNA added to the media of vaccinia-infected cells Because cells do not take up exogenous DNA under normal culturing conditions, this DNA serves to trap nonspecific DNA binding compounds and disable their cellular uptake. Compounds that were affected by the exogenous DNA were identified by the loss of antiviral activity. As shown in Table 6, a total of 16 compounds retained their antiviral activity in the presence of the extracellular DNA trap, indicating that these compounds were relevant inhibitors that block a mechanistic step in DNA synthesis.

When tested in 20 h assays, three relevant hit compounds had a SI of 4 or higher, with the most effective compound having a SI of 13 (Table 6). These 16 compounds were tested for cell protection and cytotoxicity over longer times (48 h and 72 h). At these longer times, the compounds showed diminishing antiviral activity and increasing cytotoxicity as compared to the overnight assays. The antiviral activities of four compounds were high enough to allow calculation of EC50 values, but 12 compounds showed less than 50% protection in the 72 h assays. When calculable, the SI for each compound was lower in the 72 h assay than in the overnight assays. For example, compound I has an SI of 13.2 over 20 h, and an SI of 3.2 over 72 h. The solubility of the 16 compounds was verified in cell growth medium over the range of concentrations used in the activity assays. Light scattering measurements indicated that 11 compounds were completely soluble, while five compounds (8, 10, 12, 13, and 16) were just slightly insoluble at the $EC_{50}$.

The inventor of the instant application has discovered 16 inhibitors of vaccinia DNA synthesis that have antiviral activity. These 16 inhibitors were identified by the HTS of 49663 compounds using an in vitro DNA synthesis rapid plate assay. All of the inhibitors effectively block viral infection with minimal toxicity to the cells and could not be trapped outside the cells by exogenous DNA, indicating that their antiviral activity is mediated by the disruption of an essential step in the mechanism of viral DNA synthesis. Of particular interest, three of the inhibitors had selectivity indexes that approximate that of CDV, the well-known poxvirus DNA synthesis inhibitor. Because these new inhibitors are not nucleoside analogues, they are expected to block vaccinia DNA synthesis through a mechanism that is distinct from that of CDV, a nucleoside analogue. Further development of these 16 synthetic compounds could lead to useful pox antiviral compounds that will complement the inhibitory activity of CDV and thus reduce the emergence of drug resistant mutants. On the basis of the high sequence similarity between the proteins of vaccinia and variola viruses that are responsible for DNA synthesis, these new inhibitors can be equally effective against smallpox. Future enzymatic and virological studies will identify the specific DNA synthesis proteins targeted by these poxvirus inhibitors.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of inhibiting, treating, or abrogating a poxvirus infection in a subject comprising the step of administering to said subject a compound of formula XLIV:

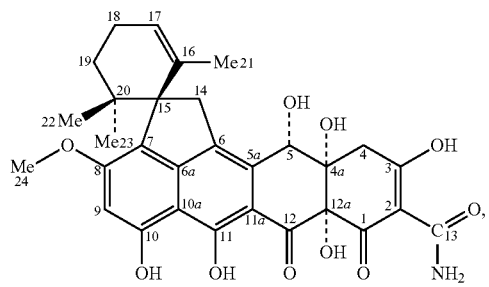

whereby said compound reduces, inhibits, or abrogates activity of a DNA polymerase of said poxvirus, thereby inhibiting, treating, or abrogating a poxvirus infection in the subject.

2. The method of claim 1, wherein said step of inhibiting replication of a poxvirus comprises inhibiting DNA synthesis.

3. The method of claim 1, wherein said poxvirus is a vaccinia virus or a variola virus.

4. The method of claim 1, wherein said DNA polymerase is an E9 DNA polymerase or a homologue thereof from a different species.

5. The method of claim 1, whereby said compound reduces, inhibits, or abrogates interaction of said DNA polymerase with a processivity factor, thereby affecting activity of said DNA polymerase.

6. The method of claim 5, wherein said processivity factor is an A20 or D4R processivity factor or a homologue thereof from a different species.

7. A method of inhibiting replication of a poxvirus, comprising a step of contacting said poxvirus with a compound of formula XLIV:

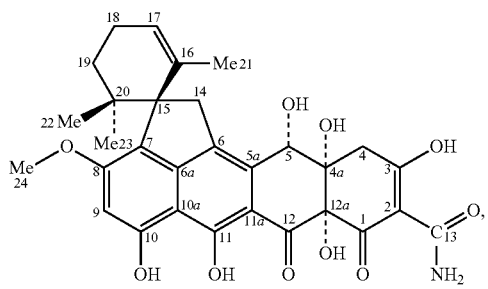

whereby said compound reduces, inhibits, or abrogates activity of a DNA polymerase of said poxvirus, thereby inhibiting replication of the poxvirus.

8. The method of claim 7, wherein said inhibiting replication of a poxvirus comprises the step of inhibiting DNA synthesis of said poxvirus.

9. The method of claim 7, wherein said poxvirus is a vaccinia virus or a variola virus.

10. The method of claim 7, wherein said DNA polymerase is an E9 DNA polymerase or a homologue thereof from a different species.

11. The method of claim 7, whereby said compound reduces, inhibits, or abrogates interaction of said DNA polymerase with a processivity factor, thereby affecting activity of said DNA polymerase.

12. The method of claim 11, wherein said processivity factor is an A20 or D4R processivity factor or a homologue thereof from a different species.

* * * * *

SEQUENCE LISTING

<160> NUMBER OF SEQ IDS NOS: 10

<210> SEQ ID NO 1
<211> LENGTH: 20
<212> TYPE: DNA
<213> ORGANISM: POX VIRUS

<400> SEQUENCE: 1
gccaatgaat gaccgctgac                                              20

<210> SEQ ID NO 2
<211> LENGTH: 100
<212> TYPE: DNA
<213> ORGANISM: POX VIRUS

<400> SEQUENCE: 2
gcacttattg cattcgctag tccaccttgg atctcaggct attcgtagcg acctacgcgt   60
acgttagctt cggtcatccc gtcagcggtc attcattggc                        100

<210> SEQ ID NO 3
<211> LENGTH: 25
<212> TYPE: DNA
<213> ORGANISM: POX VIRUS

<400> SEQUENCE: 3
ggacagttta aaaattgcgc gctcc                                        25

<210> SEQ ID NO 4
<211> LENGTH: 34
<212> TYPE: DNA
<213> ORGANISM: POX VIRUS

<400> SEQUENCE: 4
cgtctagatc tattcctatt tcttcagcga tagc                              34

<210> SEQ ID NO 5
<211> LENGTH: 24
<212> TYPE: DNA
<213> ORGANISM: POX VIRUS

<400> SEQUENCE: 5
cttcggatcc aaatgctgtc tgcg                                         24

<210> SEQ ID NO 6
<211> LENGTH: 26
<212> TYPE: DNA
<213> ORGANISM: POX VIRUS

<400> SEQUENCE: 6
cgccgttgca acttagtgtc atggtg                                       26

<210> SEQ ID NO 7
<211> LENGTH: 25
<212> TYPE: DNA
<213> ORGANISM: POX VIRUS

<400> SEQUENCE: 7
ggaatcgaag gagctactgc tgcac                                        25

<210> SEQ ID NO 8
<211> LENGTH: 26
<212> TYPE: DNA
<213> ORGANISM: POX VIRUS

```
<400> SEQUENCE: 8
cttatccgcc tccgttgtca taaacc                                          26

<210> SEQ ID NO 9
<211> LENGTH: 22
<212> TYPE: DNA
<213> ORGANISM: POX VIRUS

<400> SEQUENCE: 9
ccatggtgaa ggtgaagact gc                                              22

<210> SEQ ID NO 10
<211> LENGTH: 20
<212> TYPE: DNA
<213> ORGANISM: POX VIRUS

<400> SEQUENCE: 10
cagccttgac agtgccatgg                                                 20
```